United States Patent
Wang et al.

(10) Patent No.: US 7,470,798 B2
(45) Date of Patent: *Dec. 30, 2008

(54) 7,8-BICYCLOALKYL-CHROMAN DERIVATIVES

(75) Inventors: Bing Wang, Cupertino, CA (US); Gail Walkinshaw, Mountain View, CA (US); Jian Chen, Sunnyvale, CA (US); Xianming Jin, Fremont, CA (US); Jiangao Song, Cupertino, CA (US); Wei Zhang, Santa Clara, CA (US)

(73) Assignee: Edison Pharmaceuticals, Inc., San Jose, CA (US)

( * ) Notice: Subject to any disclaimer, the term of this patent is extended or adjusted under 35 U.S.C. 154(b) by 575 days.

This patent is subject to a terminal disclaimer.

(21) Appl. No.: 10/941,121

(22) Filed: Sep. 15, 2004

(65) Prior Publication Data

US 2005/0065149 A1  Mar. 24, 2005

Related U.S. Application Data

(60) Provisional application No. 60/541,737, filed on Feb. 4, 2004, provisional application No. 60/504,391, filed on Sep. 19, 2003.

(51) Int. Cl.
*C07D 309/00* (2006.01)
(52) U.S. Cl. .................................. 549/358; 549/358
(58) Field of Classification Search ................. 549/358
See application file for complete search history.

(56) References Cited

U.S. PATENT DOCUMENTS

| | | | |
|---|---|---|---|
| 3,154,565 A | 10/1964 | Linn et al. |
| 3,160,638 A | 12/1964 | Folkers et al. |
| 3,574,627 A | 4/1971 | Stern et al. |
| 3,801,603 A | 4/1974 | Hartmann et al. |
| 4,360,532 A | 11/1982 | Sundeen |
| 4,452,801 A | 6/1984 | Sundeen |
| 4,511,685 A | 4/1985 | Nissen et al. |
| 4,515,975 A | 5/1985 | Vogel et al. |
| 4,523,024 A | 6/1985 | Shiono et al. |
| 4,645,845 A | 2/1987 | Gehrken et al. |
| 4,694,090 A | 9/1987 | Shiono et al. |
| 4,716,238 A | 12/1987 | Timar et al. |
| 4,728,650 A | 3/1988 | Eziri |
| 4,780,469 A | 10/1988 | Toda et al. |
| 4,814,346 A | 3/1989 | Albert |
| 4,877,810 A | 10/1989 | Mickle et al. |
| 4,950,684 A | 8/1990 | Koszyk et al. |
| 5,015,661 A | 5/1991 | Walser |
| 5,055,598 A | 10/1991 | Ohuchida et al. |
| 5,082,849 A | 1/1992 | Haung et al. |
| 5,093,353 A | 3/1992 | Koszyk et al. |
| 5,099,012 A | 3/1992 | Wu et al. |
| 5,132,310 A | 7/1992 | Walser |
| 5,155,130 A | 10/1992 | Stanton et al. |
| 5,260,294 A | 11/1993 | Walser |
| 5,290,797 A | 3/1994 | Le Baut et al. |
| 5,326,771 A | 7/1994 | Heine |
| 5,350,751 A | 9/1994 | Wagner et al. |
| 5,385,931 A | 1/1995 | Bigg et al. |
| 5,395,834 A | 3/1995 | Le Baut et al. |
| 5,424,321 A | 6/1995 | Hellberg et al. |
| 5,484,810 A | 1/1996 | Grisar et al. |
| 5,500,444 A | 3/1996 | Grisar et al. |
| 5,534,536 A | 7/1996 | Ohuchida et al. |
| 5,541,199 A | 7/1996 | Mewshaw |
| 5,607,966 A | 3/1997 | Hellberg et al. |
| 5,646,149 A | 7/1997 | Hellberg et al. |
| 5,663,294 A | 9/1997 | Colman et al. |
| 5,670,667 A | 9/1997 | Mewshaw |
| 5,672,710 A | 9/1997 | Beard et al. |
| 5,684,039 A | 11/1997 | Mewshaw |
| 5,719,180 A | 2/1998 | Shudo |
| 5,747,528 A | 5/1998 | Trivedi |
| 5,750,544 A | 5/1998 | Ohuchida et al. |
| 5,756,521 A | 5/1998 | Mewshaw |
| 5,811,438 A | 9/1998 | Hellberg et al. |
| 5,821,130 A | 10/1998 | Baldwin et al. |
| 5,821,264 A | 10/1998 | Lane et al. |
| 5,849,755 A | 12/1998 | Englert et al. |
| 5,874,461 A | 2/1999 | De Chaffoy de Courcelles et al. |
| 5,925,673 A | 7/1999 | Hellberg et al. |

(Continued)

FOREIGN PATENT DOCUMENTS

DE                3842029            6/1990

(Continued)

OTHER PUBLICATIONS

U.S. Appl. No. 10/941,125, filed Sep. 15, 2004, Wang et al.

(Continued)

*Primary Examiner*—Janet L. Andres
*Assistant Examiner*—Raymond Covington
(74) *Attorney, Agent, or Firm*—Morrison & Foerster LLP

(57) ABSTRACT

7,8-Bicyclic-chroman derivatives of Formula I:

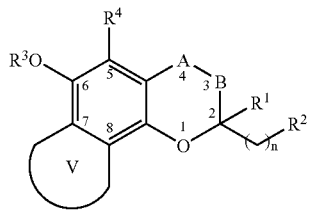

wherein the substituents are defined as in the specification or the pharmaceutically acceptable salts thereof, are disclosed. They are useful for the treatment of inflammatory disorders, neurodegenerative disorders and/or mitochondrial disorders. They are also useful in the manufacture of pharmaceutical formulations for the treatment of such conditions.

28 Claims, No Drawings

U.S. PATENT DOCUMENTS

| | | |
|---|---|---|
| 5,981,530 A | 11/1999 | Ogata et al. |
| 5,981,572 A | 11/1999 | Ellis et al. |
| 5,990,142 A | 11/1999 | Carganico |
| 6,034,256 A | 3/2000 | Carter et al. |
| 6,133,277 A | 10/2000 | Wingerinck et al. |
| 6,150,402 A | 11/2000 | Wechter et al. |
| 6,222,051 B1 | 4/2001 | Lee et al. |
| 6,235,774 B1 | 5/2001 | Fahrig et al. |
| 6,242,479 B1 | 6/2001 | Wechter |
| 6,331,532 B1 | 12/2001 | Murphy et al. |
| 6,331,561 B2 | 12/2001 | Fahrig et al. |
| 6,342,602 B1 | 1/2002 | Teng et al. |
| 6,387,899 B1 | 5/2002 | Berg et al. |
| 6,410,589 B2 | 6/2002 | Wechter |
| 6,417,223 B1 | 7/2002 | Sanders |
| 6,479,497 B1 | 11/2002 | Berg et al. |
| 6,511,966 B2 | 1/2003 | Ghosh et al. |
| 6,518,250 B2 | 2/2003 | Yoshikawa et al. |
| 6,555,575 B2 | 4/2003 | Wechter |
| 6,596,745 B2 | 7/2003 | Gall et al. |
| 6,645,998 B2 | 11/2003 | Sanders |
| 2001/0018530 A1 | 8/2001 | Fahrig et al. |
| 2002/0016359 A1 | 2/2002 | Hellberg et al. |
| 2002/0052342 A1 | 5/2002 | Murphy et al. |
| 2002/0082292 A1 | 6/2002 | Sahoo et al. |
| 2002/0127252 A1 | 9/2002 | Kramer et al. |
| 2003/0069208 A1 | 4/2003 | Murphy et al. |
| 2003/0100603 A1 | 5/2003 | Beinlich et al. |
| 2003/0103895 A1 | 6/2003 | Cyr |
| 2003/0103899 A1 | 6/2003 | Cyr |
| 2003/0176448 A1 | 9/2003 | Ghosh et al. |
| 2003/0233002 A1 | 12/2003 | Kanter et al. |
| 2004/0097433 A1 | 5/2004 | Boddupalli et al. |

FOREIGN PATENT DOCUMENTS

| | | |
|---|---|---|
| EP | 0535283 | 4/1993 |
| JP | 60001177 | 1/1985 |
| JP | 61148173 | 7/1986 |
| JP | 08041008 | 2/1996 |
| JP | 10251247 | 9/1998 |
| WO | WO 87/05020 | 8/1987 |
| WO | WO 96/16957 | 6/1996 |
| WO | WO 01/05781 | 1/2001 |

OTHER PUBLICATIONS

U.S. Appl. No. 10/941,126, filed Sep. 15, 2004, Wang et al.
Skinner, Journal of Medicinal Chemistry 1967, 10(4): 657-661.
Wolf et al., Ann. N.Y. Acad. Sci. 1982, 393: 392-410.
Wolf et al., Klinische Wochenschrift 1981, 59: 463-65.
Christen, Proc. Natl. Acad. Sci. 1997, 94: 3217-3222.
Lang, Heart 2002, 87:316-318.
Dallaker, Chemiker Zeitung 1991, 115(10): 285-9.

7,8-BICYCLOALKYL-CHROMAN DERIVATIVES

CROSS-REFERENCE TO RELATED APPLICATIONS

This U.S. patent application claims priority under 35 U.S.C. 119(e) to U.S. Provisional Applications Ser. No. 60/504,391, filed Sep. 19, 2003, and Ser. No. 60/541,737, filed Feb. 4, 2004 incorporated herein by reference in their entirety.

BACKGROUND INFORMATION

The present invention relates to novel 7,8-bicycloalkyl-chroman derivatives, pharmaceutical formulations containing them, and their uses as therapeutic agents, and syntheses therefor.

Cerebral ischemia or stroke refers to the severe diminution or cessation of blood flow to all or part of the brain. Cerebral ischemia can occur as a result of a number of causes or insults, including, but not limited to cerebrovascular occlusion, thromboembolytic insult, cardiac failure and hemorrhagic accident. It is now known that pharmacologic intervention, if provided within a reasonable interval of the initial insult, can significantly reduce cerebral tissue death following cerebral ischemia.

The use of certain chroman-ylmethylamino derivatives for the treatment of Parkinson's disease and epilepsy has been disclosed in U.S. Pat. Nos. 5,663,294; 5,541,199; 5,670,667; 5,684,039; 5,756,521; 6,235,774; and 6,331,561. The use of chromans for treating mitochondria associated diseases including Alzheimer's disease, diabetes mellitus, Parkinson's disease, neuronal and cardiac ischemia, Huntington's disease, and stroke is disclosed in U.S. Pat. Nos. 6,498,191 and 6,511,966 and U.S. patent application US 2003/0176448. Triphenyl phosphonium tocopherol analogs having cardioprotective or mitochondrially targeted antioxidant properties have been described by Gisar, J M in EP 545,283 and by Murphy, M. in *Annals of the New York Academy of Sciences* (2002), 959, 263-274 and in U.S. Pat. No. 6,331,532, US 2202/00523242 and US 2003/0069208. These applications neither teach nor suggest the 7,8-bicycloalkyl-chromans derivatives described in this invention.

The use of antioxidants targeted to mitochondria shown to be effective at slowing disease progression has been reported by Jauslin, M L in *FASEB Journal*, express article 10.1096/fj.03-0240fje. Therapeutic benefit of administering y-tocopherol derivatives and metabolites as antioxidants and nitrogen oxide scavengers which treat high blood pressure, thromboembolic diseases, cardiovascular disease, cancer, natriuretic disease, formation of neuropathological lesion and reduced immune system response are disclosed in U.S. Pat. Nos. 6,555,575; 6,242,479; 6,150,402; and 6,410,589. The use of certain chroman derivatives in cosmetic and dermatological preparations is disclosed in US 2002/0127252. Beneficial effects of Vitamin E in the progression of a number of major degenerative diseases of the nervous system is examined in Fryer, *Nutritional Neuroscience*, (1998) Vol. 1, 327-351. Reduction of the inflammation marker CRP with 6-hydroxy chromans and with tocopherols has been disclosed in commonly owned US patent applications 60/426,764 and US 2003/0100603, but these applications neither teach nor suggest the use of 7,8-bicycloalkyl-chromans derivatives described in this invention.

The present invention addresses the desire to provide new therapies for conditions that affect millions of people, and particularly for conditions characterized by neuroprotection, neuroinflammation, cognitive disorders, neurodegenerative and/or mitochondrial dysfunction conditions with novel 7,8-bicyloalkyl-chroman derivatives of Formula I. There remains a need for providing protection with agents that are effective even if first administered after a significant time (e.g. about 5 hours) following an ischemic or oxidative insult. The compounds of the present invention address this need.

SUMMARY OF THE INVENTION

The present invention is concerned with novel 7,8-bicyclochroman derivatives which may be useful in the manufacture of pharmaceutical compositions for treating or ameliorating a number of conditions characterized by neurodegeneration, oxidative stress or mitochondrial disorders.

It has surprisingly been found that certain compounds of this invention may limit or prevent damage to organelles, cells, and tissues caused by mitochondrial dysfunction, oxidative stress or neuroinflammation, as demonstrated by providing protection in standard experimental models of mitochondrial dysfunction caused by MPP$^+$ and the MPTP (1-methyl4-phenylpyridinium or 1-methyl4-phenyl-1,2,3,4-tetrahydropyridine) models or of oxidative stress caused by beta amyloid or high glutamate. These compounds have also shown protection in the experimental model using FRDA fibroblasts, and in the MCAO animal model of cerebral ischemia showing potent neuroprotective protection with anti-inflammatory and anti-edema activity. Certain compounds may also show lipoxygenase inhibition.

Certain compounds of the present invention may also be useful in the treatment or amelioration of indications characterized by oxidative stress and/or inflammation, including, but not limited to, diabetes, cardiopulmonary inflammatory disorders, skin inflammation or other skin disorders, premenstrual disease (PMS), chronic heart failure, rheumatoid arthritis, and muscle fatigue. In a first aspect, the present invention concerns the novel compounds represented by Formula I:

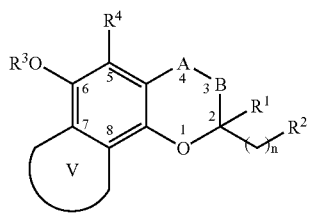

Formula I wherein:
-A-B— is —CH$_2$—(CH$_2$)$_{0-2}$—; —CH=CH—; —CH$_2$—O—; —CH$_2$—S—; or —CH$_2$—N—;
n is 0 to 5;
V is C$_{7-12}$-bicyclo[a.b.c]alkyl; C$_{7-12}$-bicyclo[a.b.c]alkenyl; C$_{7-12}$-heterobicyclo[a.b.c]alkyl; or C$_{7-12}$-heterobicyclo[a.b.c]alkenyl; and a, b, and c are 0 to 6; and wherein the bicyclo ring is optionally substituted with one or more substituents selected from C$_{1-6}$ alkyl, halogen, haloalkyl, carboxy, alkoxycarbonyl, cyano, hydroxy, alkoxy, thiol, and oxo;
R$^1$ is C$_{1-6}$ alkyl;
R$^2$ is C$_{1-20}$ alkyl; optionally substituted C$_{2-20}$ alkenyl; halogen; hydroxy; alkoxy; acyl; —C(O)OR; —S(O)$_2$OR; —NR'R"; —NH—C(=NH$_2$)—NR'R"; —N—SO$_2$R; —NHC(O)NR'R"; —N(OH)C(O)NR'R"; —SO$_2$NR'R";

—C(O)NR'R"; —S(O)$_{0-2}$R'"; —PO(OR)$_2$; triphenylphosphonium; trialkylphosphonium; optionally substituted aryl; optionally substituted heterocyclyl;

R$^3$ is hydrogen; optionally substituted C$_{1-20}$ alkyl; C$_{2-20}$ alkenyl; hydroxyalkyl; acyl; glucoside; phosphoryl; phosphoryloxyalkyl; carboxyalkylcarbonyl; aminoalkylcarbonyl; or alkylketocarbonyl;

R$^4$ is hydrogen; halogen; nitro; cyano; optionally substituted alkyl; aryl, aralkyl, heterocyclyl or heterocyclylalkyl, all optionally substituted with alkyl, hydroxy, alkoxy, nitro, acyl, amino, oxo, or —C(O)OR; optionally substituted alkenyl; hydroxy; alkoxy; nitro; —C(O)OR; —C(O)NR'R"; —NR'R"; —NHC(O)NR'R"; —NR'—SO$_2$—R; —NH—C(=NH$_2$)—NR'R"; —SO$_2$NR'R", or —P(O)(OR)$_2$; or R$^3$ and R$^4$ taken together with the atoms to which they are attached may form a heterocyclic ring;

R is hydrogen; optionally substituted alkyl; optionally substituted aryl; optionally substituted arylalkyl; optionally substituted cycloalkyl; or optionally substituted heterocyclyl;

R' and R" are independently of each other hydrogen; C$_{1-6}$ alkyl; hydroxyalkyl; aminoalkyl; optionally substituted aryl; or optionally substituted benzyl; or R' and R" taken together with the atom to which they are attached may form a 5 to 8 membered aromatic, saturated or unsaturated ring, optionally incorporating one additional atom chosen from N, O, or S and optionally substituted with a substituent selected from the group consisting of C$_{1-6}$ alkyl, halo, cyano, alkylthio, lower alkoxy, phenyl, benzyl and carboxy; and R'" is optionally substituted C$_{1-6}$ alkyl; optionally substituted aryl; or optionally substituted heterocyclyl; or single stereoisomers and mixtures of stereoisomers, or the pharmaceutically acceptable salts thereof.

In one embodiment, R$^3$ is hydrogen. In another embodiment, R$^4$ is hydrogen, C$_{1-6}$ alkyl optionally substituted with halogen, haloalkyl, hydroxy, alkoxy, amino, sulfanyl, carboxy, nitro or cyano; or C$_{2-12}$ alkenyl optionally substituted with halogen, haloalkyl, hydroxy, alkoxy, amino, sulfanyl, carboxy, nitro or cyano.

In another embodiment, V is a bicyclo[2.2.1]heptane ring and the compound is represented by Formula Ia:

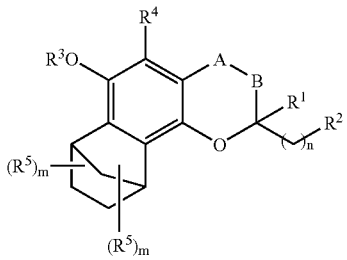

Formula Ia wherein -A-B— is —CH$_2$—CH$_2$— or —CH=CH—; R$^1$, R$^2$, R$^3$, R$^4$, and n are as defined in Formula I; m is in each occurrence independently 0-3; and R$^5$ is selected from optionally substituted C$_{1-6}$-alkyl, halogen, haloalkyl, carboxy, alkoxycarbonyl, cyano, hydroxy, alkoxy, thiol, and oxo. Preferably, V is a bicyclo[2.2.1]heptane ring and R$^2$ is C$_{1-6}$ alkyl; halogen; hydroxy; alkoxy; —C(O)OR; —SO$_2$NR'R"; —C(O)NR'R"; —SR'"; —PO(OR)$_2$; triphenylphosphonium; trialkylphosphonium; phenyl optionally substituted with C$_{1-6}$ alkyl, halogen, haloalkyl, carboxy, alkoxycarbonyl, cyano, hydroxy, alkoxy, thiol, and oxo; or heterocyclyl selected from morpholine, piperidine, piperazine, thiazole, thiazolidine, isothiazole, oxazole, isoxazole, pyrazole, pyrazolidine, pyrazoline, imidazole, imidazolidine, benzothiazole, pyridine, pyrazine, pyrimidine, pyridazine, pyrrole, pyrrolidine, quinoline, quinazoline, purine, carbazole, benzimidazole, pyrimidine, thiophene, benzothiophene, pyran, tetrahydropyran, benzopyran, furan, tetrahydrofuran, indole, indoline, indazole, xanthene, thioxanthene, acridine, and quinuclidine, optionally substituted with C$_{1-6}$ alkyl, halogen, haloalkyl, carboxy, alkoxycarbonyl, cyano, hydroxy, alkoxy, thiol, and oxo.; and more preferably, V is a bicyclo[2.2.1]heptane ring, R$^2$ is —COOR and R is hydrogen or C$_{1-6}$ alkyl. In another embodiment V is a bicyclo[2.2.1]heptane ring, R$^1$ and R$^2$ are C$_{1-6}$ alkyl and m and n are 0.

In another embodiment, V is a bicyclo[2.2.2] octane ring and the compound is represented by Formula Ib:

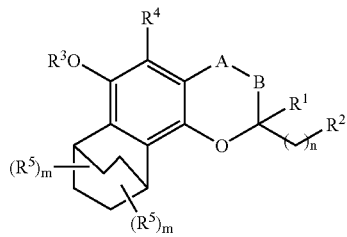

Formula Ib wherein -A-B— is —CH$_2$—CH$_2$— or —CH=CH—; R$^1$, R$^2$, R$^3$, R$^4$, and and n are as defined in Formula I; m is in each occurrence independently 0-3; and R$^5$ is selected from optionally substituted C$_{1-6}$-alkyl, halogen, haloalkyl, carboxy, alkoxycarbonyl, cyano, hydroxy, alkoxy, thiol, and oxo. Preferably V is a bicyclo[2.2.2]octane ring and R$^2$ is C$_{1-6}$ alkyl; halogen; hydroxy; alkoxy; —C(O)OR; —SO$_2$NR'R"; —C(O)NR'R"; —SR'"; —PO(OR)$_2$; triphenylphosphonium; trialkylphosphonium; phenyl optionally substituted with C$_{1-6}$ alkyl, halogen, haloalkyl, carboxy, alkoxycarbonyl, cyano, hydroxy, alkoxy, thiol, and oxo; or heterocyclyl selected from morpholine, piperidine, piperazine, thiazole, thiazolidine, isothiazole, oxazole, isoxazole, pyrazole, pyrazolidine, pyrazoline, imidazole, imidazolidine, benzothiazole, pyridine, pyrazine, pyrimidine, pyridazine, pyrrole, pyrrolidine, quinoline, quinazoline, purine, carbazole, benzimidazole, pyrimidine, thiophene, benzothiophene, pyran, tetrahydropyran, benzopyran, furan, tetrahydrofuran, indole, indoline, indazole, xanthene, thioxanthene, acridine, and quinuclidine, optionally substituted with C$_{1-6}$ alkyl, halogen, haloalkyl, carboxy, alkoxycarbonyl, cyano, hydroxy, alkoxy, thiol, and oxo; and more preferably V is a bicyclo[2.2.2]octane ring, R$^2$ is —COOR, and R is hydrogen or C$_{1-6}$ alkyl. In another embodiment V is a bicyclo[2.2.2] octane ring and R$^1$ and R$^2$ are independently of each other C$_{1-6}$ alkyl and m and n are 0.

In another embodiment, V is a bicyclo[3.2.2]nonane ring and the compound is represented by Formula Ic:

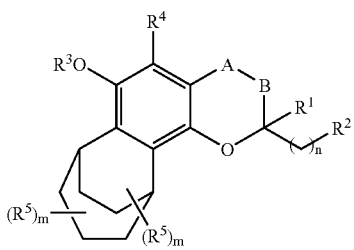

Formula Ic wherein -A-B— is —CH$_2$—CH$_2$— or —CH=CH—; R$^1$, R$^2$, R$^3$, R$^4$, and and n are as defined in Formula I; m is in each occurrence independently 0-3; and R$^5$ is selected from optionally substituted C$_{1-6}$-alkyl, halogen, haloalkyl, carboxy, alkoxycarbonyl, cyano, hydroxy, alkoxy, thiol, and oxo. Preferably V is a bicyclo[3.2.2]nonane ring and R$^2$ is C$_{1-6}$ alkyl; halogen; hydroxy; alkoxy; —C(O)OR; —SO$_2$NR'R''; —C(O)NR'R''; —SR'''; —PO(OR)$_2$; triphenylphosphonium; trialkylphosphonium; phenyl optionally substituted with C$_{1-6}$ alkyl, halogen, haloalkyl, carboxy, alkoxycarbonyl, cyano, hydroxy, alkoxy, thiol, and oxo; or heterocyclyl selected from morpholine, piperidine, piperazine, thiazole, thiazolidine, isothiazole, oxazole, isoxazole, pyrazole, pyrazolidine, pyrazoline, imidazole, imidazolidine, benzothiazole, pyridine, pyrazine, pyrimidine, pyridazine, pyrrole, pyrrolidine, quinoline, quinazoline, purine, carbazole, benzimidazole, pyrimidine, thiophene, benzothiophene, pyran, tetrahydropyran, benzopyran, furan, tetrahydrofuran, indole, indoline, indazole, xanthene, thioxanthene, acridine, and quinuclidine, optionally substituted with C$_{1-6}$ alkyl, halogen, haloalkyl, carboxy, alkoxycarbonyl, cyano, hydroxy, alkoxy, thiol, and oxo.; and more preferably V is a bicyclo[3.2.2]nonane ring, R$^2$ is —COOR, and R is hydrogen or C$_{1-6}$ alkyl. In another embodiment V is a bicyclo[3.2.2]nonane ring, R$^1$ and R$^2$ are independently of each other C$_{1-6}$ alkyl and n is 0.

In another embodiment, -A-B— is —CH$_2$—CH$_2$— and n is 2 or 3, and in a preferred embodiment, -A-B — is —CH$_2$—CH$_2$—; n is 2 or 3 and V is a bicyclo[2.2.1]heptane ring, a bicyclo[2.2.2]octane ring, or a bicyclo[3.2.2]nonane ring. In another embodiment, -A-B— is —CH$_2$=CH$_2$— and n is 2 or 3, and in a preferred embodiment -A-B— is —CH$_2$=CH$_2$— and n is 2 or 3, and V is a bicyclo[2.2.1]heptane ring, a bicyclo[2.2.2]octane ring, or a bicyclo[3.2.2]nonane ring.

In another embodiment -A-B— is —CH$_2$—CH$_2$—; n is 2 or 3; R$^2$ is —C(O)OR, and R is hydrogen or C$_{1-6}$ alkyl. In another embodiment, -A-B— is —CH$_2$=CH$_2$—, n is 2 or 3; R$^2$ is —C(O)OR, and R is hydrogen or C$_{1-6}$ alkyl.

In another embodiment R$^1$ and R$^2$ are independently of each other C$_{1-6}$ alkyl and n is 0, particularly R$^1$ and R$^2$ are independently of each other C$_{1-6}$ alkyl, n is 0, and -A-B— is —CH$_2$—CH$_2$—. In another embodiment, R$^1$ and R$^2$ are independently of each other C$_{1-6}$ alkyl, n is 0, and -A-B— is —CH$_2$=CH$_2$—.

In another embodiment the invention relates to a pharmaceutical composition comprising a compound of Formula I or stereoisomers, mixtures of stereoisomers or pharmaceutically acceptable salts thereof, admixed with a pharmaceutically acceptable excipient, preferably to a pharmaceutical composition comprising one or more compounds selected from the group represented by the structures:

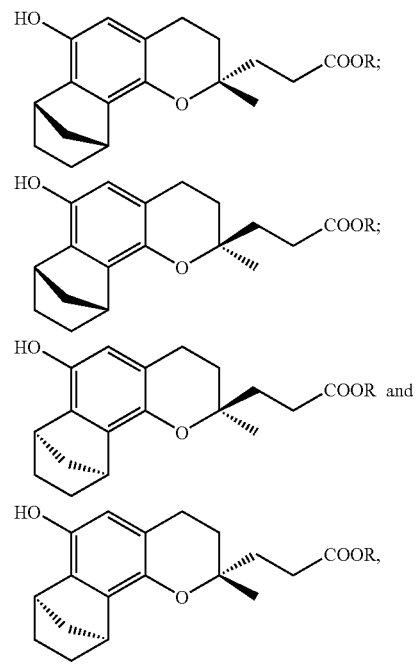

wherein R is hydrogen or C$_{1-4}$ alkyl.

In another aspect, the invention relates to the method of treating or ameliorating a subject suffering from neurodegenerative, oxidative stress and mitochondrial disorders comprising administering to said subject a therapeutically effective amount of a compound of Formula I, or stereoisomers, mixture of stereoisomers or pharmaceutically acceptable salts thereof. In another preferred embodiment the invention relates to methods of treating or ameliorating a subject from a condition selected from stroke, cerebral ischemia, retinal ischemia, post-surgical cognitive dysfunctions, peripheral neuropathy/neuropathic pain, spinal cord injury, head injury and surgical trauma.

In another embodiment, the invention relates to a method of treating or ameliorating a subject suffering from mitochondrial disorders such as but not limited to epilepsy, Parkinsonism or Parkinson's disease, Alzheimer's disease, amyotrophic lateral sclerosis (ALS) and other motor neuron diseases, macular degeneration, mitochondrial myopathy, encephalopathy, lactacidosis, stroke (MELAS), myoclonic epilepsy with ragged red fibers (MERFF), Friedreich's ataxia and cerebellar ataxias in a mammal by administering to a mammal in need of such treatment a therapeutically effective amount of a compound of Formula I, or stereoisomers, mixture of stereoisomers or pharmaceutically acceptable salts thereof.

In another preferred embodiment the invention relates to methods of treating or ameliorating a subject suffering from an oxidative stress disorder with inflammatory or autoimmune components, especially treating a subject suffering from disorders including but not limited to diabetes, renal disease, premenstrual syndrome, asthma, chronic obstructive pulmonary disease (COPD), rheumatoid arthritis, osteoarthritis, muscle fatigue, irritable bowel syndrome, inflammatory bowel disease (IBD), premenstrual syndrome (PMS), and intermittent claudication. In another preferred embodiment the invention relates to methods of treating or ameliorating a subject suffering from dermatological conditions characterized by oxidative stress, including, but not limited to age-related skin damage; damage resulting from insults to the skin such as harmful ultraviolet (UV) radiation, pollution, stress and fatigue; contact dermatitis; skin irritation; skin pigmentation; psoriasis; or acne.

In another embodiment the invention relates to a method of inhibiting a lipoxygenase enzyme in a subject in need of such inhibition which comprises administering to said subject a therapeutically effective amount of a compound of Formula I, including stereoisomers, mixture of stereoisomers and pharmaceutically acceptable salts thereof, particularly the said method comprises administering a compound of Formula I to a mammal suffering from asthma, chronic obstructive disease, arthritis, rheumatoid arthritis, osteoarthritis, allergic rhinitis, psoriasis, a diabetic condition or cardiovascular disease.

Particularly preferred are those methods of treatment or amelioration and uses in the manufacture of pharmaceutical compositions therefor, wherein the compound of Formula I is selected from the preferred compounds or stereoisomers, mixture of stereoisomers or pharmaceutically acceptable salts thereof, and especially from the compounds selected from:

3-(6-Hydroxy-2-methyl-3,4,7,8,9,10-hexahydro-7,10-methano-2H-benzo[h]chromen-2-yl)-propionic acid methyl ester;
3-(6-Hydroxy-2-methyl-3,4,7,8,9,10-hexahydro-7,10-methano-2H-benzo[h]chromen-2-yl)-propionic acid;
3-(6-Hydroxy-2-methyl-3,4,7,8,9,10-hexahydro-7,10-propano-2H-benzo[h]chromen-2-yl)-propionic acid methyl ester;
2-Methyl-2-[3-(thiazol-2-ylsulfanyl)-propyl]-3,4,7,8,9,10-hexahydro-7,10-methano-2H-benzo[h]chromen-6-ol;
[3-(6-Hydroxy-2-methyl-3,4,7,8,9,10-hexahydro-7,10-methano-2H-benzo[h]chromen-2-yl)-propyl]-phosphonic acid dimethyl ester;
[3-(6-Hydroxy-2-methyl-3,4,7,8,9,10-hexahydro-7,10-methano-2H-benzo[h]chromen-2-yl)-propyl]-phosphonic acid;
3-(6-Hydroxy-2-methyl-3,4,7,8,9,10-hexahydro-7,10-methano-2H-benzo[h]chromen-2-yl)-propionic acid methyl ester;
4-(6-Hydroxy-2-methyl-3,4,7,8,9,10-hexahydro-7,10-methano-2H-benzo[h]chromen-2-yl)-butane-1-sulfonic acid dimethylamide;
2-(3-Hydroxy-propyl)-2-methyl-3,4,7,8,9,10-hexahydro-7,10-methano-2H-benzo[h]chromen-6-ol;
3-(6-Hydroxy-2-methyl-3,4,7,8,9,10-hexahydro-7,10-methano-2H-benzo[h]chromen-2-yl)-propionic acid methyl ester;
3-(6-Hydroxy-2-methyl-3,4,7,8,9,10-hexahydro-7,10-methano-2H-benzo[h]chromen-2-yl)-propionic acid;
3-[7-(2-Methoxycarbonyl-ethyl)-2,7-dimethyl-2,7,9,10,11,12-hexahydro-1,8-dioxa-0-12-methano-triphenylen-2-yl]-propionic acid methyl ester;
3-[6-Hydroxy-2-methyl-5-(3-methyl-but-2-enyl)-3,4,7,8,9,10-hexahydro-7,10-methano-2H-benzo[h]chromen-2-yl]-propionic acid;
2-(3-Hydroxy-propyl)-2-methyl-3,4,7,8,9,10-hexahydro-7,10-propano-2H-benzo[h]chromen-6-ol;
3-(6-Hydroxy-2-methyl-3,4,7,8,9,10-hexahydro-7,10-propano-2H-benzo[h]chromen-2-yl)-propionic acid;
3-(6-Hydroxy-2-methyl-3,4,7,8,9,10-hexahydro-7,10-methano-2H-benzo[h]chromen-2-yl)-1-morpholin4-yl-propan-1-one;
3-(6-Hydroxy-2-methyl-3,4,7,8,9,10-hexahydro-7,10-methano-2H-benzo[h]chromen-2-yl)-1-morpholin-4-yl-propan-1-one;
2-Methyl-2-(3-piperidin-1-yl-propyl)-3,4,7,8,9,10-hexahydro-7,10-methano-2H-benzo[h]chromen-6-ol;
2-(3-Chloro-propyl)-2-methyl-3,4,7,8,9,10-hexahydro-7,10-methano-2H-benzo[h]chromen-6-ol;
1-{3-[3-(6-Hydroxy-2-methyl-3,4,7,8,9,10-hexahydro-7,10-methano-2H-benzo[h]chromen-2yl)-propylsulfanyl]-2-methyl-propionyl}-pyrrolidine-2-carboxylic acid;
2-[3-(Benzothiazol-2-ylsulfanyl)-propyl]-2-methyl-3,4,7,8,9,10-hexahydro-7,10-methano-2H-benzo[h]chromen-6-ol;
2-[3-(2-Hydroxy-ethylamino)-propyl]-2-methyl-3,4,7,8,9,10-hexahydro-7,10-methano-2H-benzo[h]chromen-6-ol;
2-[3-(2-Dimethylamino-ethylamino)-propyl]-2-methyl-3,4,7,8,9,10-hexahydro-7,10-methano-2H-benzo[h]chromen-6-ol;
2,6:9,12-Dimethano-9,10,11,12-tetrahydro-2-methylnaphtho[1,2-b]oxocan-8-ol;
2-(2-Chloro-ethyl)-2-methyl-3,4,7,8,9,10-hexahydro-7,10-methano-2H-benzo[h]chromen-6-ol;
2-Methyl-2-[3-(pyridine4-ylsulfanyl)-propyl]-3,4,7,8,9,10-hexahydro-7,10-methano-2H-benzo[h]chromen-6-ol;
2-(3-Isobutylsulfanyl-propyl)-2-methyl-3,4,7,8,9,10-hexahydro-7,10-methano-2H-benzo[h]chromen-6-ol;
2-Methyl-2-thiophen-2-yl-3,4,7,8,9,10-hexahydro-7,10-methano-2H-benzo[h]chromen-6-ol;
2-Methyl-2-thiazol-2-yl-3,4,7,8,9,10-hexahydro-7,10-methano-2H-benzo[h]chromen-6-ol;
3-(6-Hydroxy-2-methyl-3,4,7,8,9,10-hexahydro-7,10-ethano-2H-benzo[h]chromen-2-yl)-propionic acid;
3-(6-Hydroxy-2-methyl-3,4,7,8,9,10-hexahydro-7,10-ethano-2H-benzo[h]chromen-2-yl)-propionic acid methyl ester;
2-(3-Chloro-propyl)-2-methyl-3,4,7,8,9,10-hexahydro-7,10-ethano-2H-benzo[h]chromen-6-ol;
2-(3-Chloro-propyl)-2,5-dimethyl-3,4,7,8,9,10-hexahydro-7,10-ethano-2H-benzo[h]chromen-6-ol;
2-[3-(Benzothiazol-2-ylsulfanyl)-propyl]-2-methyl-3,4,7,8,9,10-hexahydro-7,10-ethano-2H-benzo[h]chromen-6-ol;
3-(6-Hydroxy-2-methyl-3,4,7,8,9,10-hexahydro-7,10-methano-2H-benzo[h]chromen-2-yl)-propionic acid, sodium salt;
3-[6-Hydroxy-2-methyl-5-(3-methyl-but-2-enyl)-3,4,7,8,9,10-hexahydro-7,10-ethano-2H -benzo[h]chromen-2-yl]-propionic acid;
Sodium salt of 3-(6-Hydroxy-2-methyl-3,4,7,8,9,10-hexahydro-7,10-ethano-2H-benzo[h]chromen-2-yl)-propionic acid;
3-(6-Hydroxy-2-methyl-3,4,7,8,9,10-hexahydro-7,10-ethano-2H-benzo[h]chromen-2-yl)-propionic acid benzyl ester;
3-(5-Bromo-6-hydroxy-2-methyl-3,4,7,8,9,10-hexahydro-7,10-ethano-2H-benzo[h]chromen-2-yl)-propionic acid;
5-Bromo-2-methyl-2-(3-piperidin-1-yl-propyl)-3,4,7,8,9,10-hexahydro-7,10-ethano-2H-benzo[h]chromen-6-ol;
5-Methoxy-2,2-dimethyl-3,4,7,8,9,10-hexahydro-7,10-methano-2H-benzo[h]chromen-6-ol;
3-(6-Hydroxy-2-methyl-3,4,7,8,9,10-hexahydro-7,10-ethano-2H-benzo[h]chromen-2-yl)-1-piperidin-1-yl-propan-1-one;
N-(2-Dimethylamino-ethyl)-3-(6-hydroxy-2-methyl-3,4,7,8,9,10-hexahydro-7,10-ethano-2H-benzo[h]chromen-2-yl)-propionamide;
2-Methyl-2-(3-piperidin-1-yl-propyl)-3,4,7,8,9,10-hexahydro-7,10-ethano-2H-benzo[h]chromen-6-ol;

3-(6-Hydroxy-2-methyl-3,4,7,8,9,10-hexahydro-7,10-ethano-2H-benzo[h]chromen-2-yl)-1-morpholin-4-yl-propan-1-one;

2-[3-(2-Dimethylamino-ethylamino)-propyl]-2-methyl-3,4,7,8,9,10-hexahydro-7,10-ethano-2H -benzo[h]chromen-6-ol;

2-Methyl-2-[3-(pyridine-4-sulfonyl)-propyl]-3,4,7,8,9,10-hexahydro-7,10-methano-2H -benzo[h]chromen-6-ol;

2,2,-Dimethyl-3,4,7,8,9,10-hexahydro-7,10-methano-2H-benzo[h]chromen-6-ol;

2,2-Dimethyl-3,4,7,8,9,10-hexahydro-7,10-methano-2H-benzo[h]chromen-6-ol;

2,2-Dimethyl-5-(3-methyl-but-2-enyl)-3,4,7,8,9,10-hexahydro-7,10-methano-2H-benzo[h]chromen-6-ol;

Acetic acid 2,2-dimethyl-5-(3-methyl-but-2-enyl)-3,4,7,8,9,10-hexahydro-7,10-methano-2H-benzo[h]chromen-6-yl ester;

2,2-Dimethyl-5-(3-methyl-butyl)-3,4,7,8,9,10-hexahydro7,10-methano-2H-benzo[h]chromen-6-ol;

5-Bromo-2,2-dimethyl-3,4,7,8,9,10-hexahydro7,10-methano-2H-benzo[h]chromen-6-ol;

Acetic acid 2,2-dimethyl-5-(3-methyl-butyl)-3,4,7,8,9,10-hexahydro-7,10-methano-2H-benzo[h]chromen-6-yl ester;

2,2-Dimethyl-3,4,7,10-tetrahydro-7,10-methano-2H-benzo[h]chromen-6-ol;

2,2-Dimethyl-3,4,7,8,9,10-hexahydro-7,10-ethano-2H-benzo[h]chromen-6-ol;

2,2-Dimethyl-5-(3-methyl-but-2-enyl)-7,8,9,10-tetrahydro-7,10-methano-2H-benzo[h]chromen-6-ol;

2,2-Dimethyl-5-(3-methyl-but-2-enyl)-3,4,7,10-tetrahydro--7,10-ethano-2H-benzo[h]chromen-6-ol;

2,2,7,7-Tetramethyl-9-12-ethano-2,3,4,5,6,7,9,10,11,12-decahydro-1,8-dioxa-triphenylene;

2-(3-Chloro-propyl)-2-methyl-3,4,7,8,9,10-hexahydro-7,10-ethano-2H-benzo[h]chromen-6-ol;

Acetic acid 2,2-dimethyl-3,4,7,8,9,10-hexahydro-7,10-ethano-2H -benzo[h]chromen-6-yl ester;

Phosphoric acid mono-(2,2-dimethyl-3,4,7,8,9,10-hexahydro-7,10-methano-2H-benzo[h]chromen-6-yl)ester, disodium salt;

2,2-Dimethyl-7,8,9,10-tetrahydro-7,10-ethano-2H-benzo[h]chromen-6-ol;

Phosphoric acid mono-(2,2-dimethyl-3,4,7,8,9,10-hexahydro-7,10-ethano 2H-benzo[h]chromen-6-yl)ester, disodium salt;

2,2-Dimethyl-5-(3-methyl-butyl)-3,4,7,8,9,10-hexahydro-7,10-ethano 2H -benzo[h]chromen-6-ol;

2,2,5-Trimethyl-3,4,7,8,9,10-hexahydro-7,10-ethano 2H -benzo[h]chromen-6-ol;

6-Hydroxy-2,2-dimethyl-3,4,7,8,9,10-hexahydro-7,10-methano-2H-benzo[h]chromene-5-carbonitrile;

2,2-Dimethyl-5-(3-methyl-but-2-enyl)-3,4,7,8,9,10-hexahydro-7,10-ethano-2H-benzo[h]chromen-6-ol;

5-Hydroxymethyl-2,2-dimethyl-3,4,7,8,9,10-hexahydro-7,10-methano-2H-benzo[h]chromen-6-ol;

5-Bromo-2,2-dimethyl-3,4,7,8,9,10-hexahydro-7,10-ethano-2H-benzo[h]chromen-6-ol;

2,2-Dimethyl-5-[2-(tetrahydro-pyran-4-ylidene)-ethyl]-3,4,7,8,9,10-hexahydro-7,10-ethano-2H-benzo[h]chromen-6-ol;

5-(2-Cyclohexylidene-ethyl)-2,2-dimethyl-3,4,7,8,9,10-hexahydro-7,10-ethano-2H-benzo[h]chromen-6-ol;

1-(6-Hydroxy-2,2-dimethyl-3,4,7,8,9,10-hexahydro-7,10-ethano-2H-benzo[h]chromen-5-yl)-ethanone;

4-(6-Acetoxy-2,2-dimethyl-3,4,7,8,9,10-hexahydro-2H-benzo[h]chromen-5-yl)4-oxo-butyric acid;

2,2-Dimethyl-5-nitro-3,4,7,8,9,10-hexahydro-7,10-methano-2H-benzo[h]chromen-6-ol;

Acetic acid 2,2-dimethyl-5-(3-methyl-but-2-enyl)-7,8,9,10-tetrahydro-7,10-methano-2H-benzo[h]chromen-6-yl ester;

5-(6-Hydroxy-2,2-dimethyl-3,4,7,8,9,10-hexahydro-7,10-methano-2H-benzo[h]chromen-5-ylmethylene)-thiazolidine-2,4-dione;

5-Hydroxy-3-(6-hydroxy-2,2-dimethyl-3,4,7,8,9,10-hexahydro-7,10-methano-2H-benzo[h]chromen-5-ylmethylene)-3H-benzofuran-2-one;

Phosphoric acid dibenzyl ester 2,2-dimethyl-3,4,7,8,9,10-hexahydro-7,10-methano-2H-benzo[h]chromen-6-yl ester;

Phosphoric acid dibenzyl ester 2,2-dimethyl-3,4,7,8,9,10-hexahydro-7,10-ethano-2H-benzo[h]chromen-6-yl ester;

10-Methoxy-2,2-dimethyl-3,4,7,8,9,10-hexahydro-7,10-ethano-2H-benzo[h]chromen-6-ol;

1-(6-Hydroxy-2,2-dimethyl-3,4,7,8,9,10-hexahydro-7,10-ethano-2H-benzo[h]chromen-5-yl)-ethanone;

4-[4-(6-Hydroxy-2,2-dimethyl-3,4,7,8,9,10-hexahydro-7,10-methano-2H-benzo[h]chromen-5-ylmethylene)-3-methyl-5-oxo4,5-dihydro-pyrazol-1-yl]-benzoic acid;

4-(6-Hydroxy-2,2-dimethyl-3,4,7,8,9,10-hexahydro-7,10-methano-2H-benzo[h]chromen-5-ylmethylene)-2-methyl-5-propyl-2,4-dihydro-pyrazol-3-one;

(6-Hydroxy-2,2-dimethyl-3,4,7,8,9,10-hexahydro-7,10-methano-2H-benzo[h]chromen-5-ylmethyl)-1-hydroxyurea;

5-(1-Hydroxy-ethyl)-2,2-dimethyl-3,4,7,8,9,10-hexahydro-7,10-methano-2H-benzo[h]chromen-6-ol; and Dimethylamino-acetic acid 2,2-dimethyl-3,4,7,8,9,10-hexahydro-7,10-ethano-2H-benzo[h]chromen-6-yl ester.

In some embodiments the methods of treatment and uses in the manufacture of pharmaceutical compositions therefor, comprise a compound of Formula I selected from the following compounds in Table 1.

TABLE 1

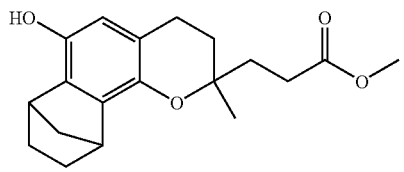

3-(6-Hydroxy-2-methyl-3,4,7,8,9,10-hexahydro-7,10-methano-2H-benzo[h]chromen-2-yl)-propionic acid methyl ester;

TABLE 1-continued

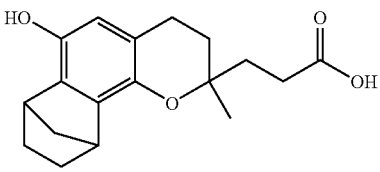
3-(6-Hydroxy-2-methyl-3,4,7,8,9,10-hexahydro-7,10-methano-2H-benzo[h]chroman-2-yl)-propionic acid;

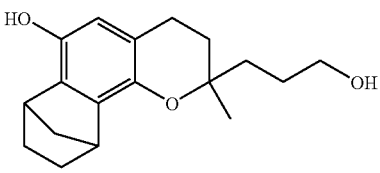
2-(3-Hydroxy-propyl)-2-methyl-3,4,7,8,9,10-hexahydro-7,10-methano-2H-benzo[h]chromen-6-ol;

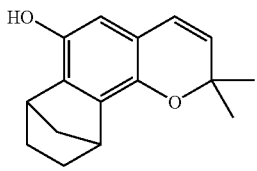
2,2,-Dimethyl-3,4,7,8,9,10-hexahydro-7,10-methano-2H-benzo[h]chromen-6-ol;

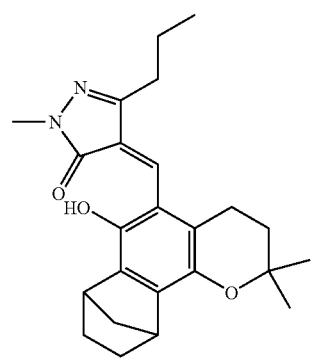
4-(6-Hydroxy-2,2-dimethyl-3,4,7,8,9,10-hexahydro-7,10-methano-2H-benzo[h]chromen-5-ylmethylene)-2-methyl-5-propyl-2,4-dihydro-pyrazol-3-one;

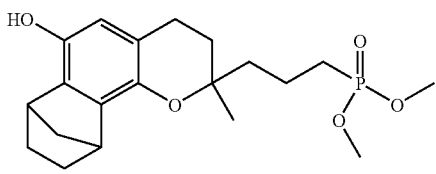
[3-(6-Hydroxy-2-methyl-3,4,7,8,9,10-hexahydro-7,10-methano-2H-benzo[h]chromen-2-yl)-propyl]-phosphonic acid dimethyl ester;

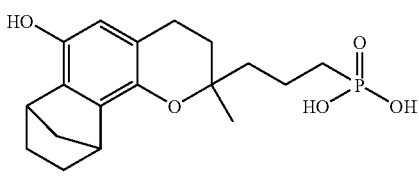
[3-(6-Hydroxy-2-methyl-3,4,7,8,9,10-hexahydro-7,10-methano-2H-benzo[h]chromen-2-yl)-propyl]-phosphonic acid;

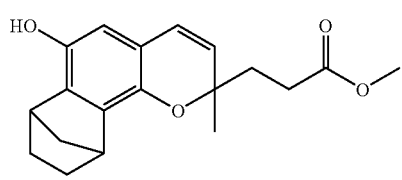
3-(6-Hydroxy-2-methyl-3,4,7,8,9,10-hexahydro-7,10-methano-2H-benzo[h]chromen-2-yl)-propionic acid methyl ester;

TABLE 1-continued

| Structure | Name |
|---|---|
| (structure) | 2-Methyl-2-thiazol-2-yl-3,4,7,8,9,10-hexahydro-7,10-methano-2H-benzo[h]chromen-6-ol; |
| (structure with S(O)$_2$N(CH$_3$)$_2$) | 4-(6-Hydroxy-2-methyl-3,4,7,8,9,10-hexahydro-7,10-methano-2H-benzo[h]chromen-2-yl)-butane-1-sulfonic acid dimethylamide; |
| (structure) | 2-Methyl-2-[3-(thia-zol-2-ylsulfanyl)-propyl]-3,4,7,8,9,10-hexahydro-7,10-meth-ano-2H-benzo[h]chromen-6-ol; |
| (structure) | 2-Methyl-2-thiazol-2-yl-3,4,7,8,9,10-hexahydro-7,10-methano-2H-benzo[h]chrome-6-ol; |
| (structure) | 3-(6-Hydroxy-2-methyl-3,4,7,8,9,10-hexahydro-7,10-propano-2H-benzo[h]chromen-2-yl)-propionic acid methyl ester; |
| (structure) | 2-(3-Chloro-ethyl-2-methyl-3,4,7,8,9,10-hexahydro-7,10-methano-2H-benzo[h]chromen-6-ol; |
| (structure) | 2-(3-Chloro-propyl)-2-methyl-3,4,7,8,9,10-hexahydro-7,10-methano-2H-benzo[h]chromen-6-ol; |
| (structure) | 2-(3-Chloro-propyl)-2-methyl-3,4,7,8,9,10-hexahydro-7,10-ethano-2H-benzo[h]chromen-6-ol; |

TABLE 1-continued

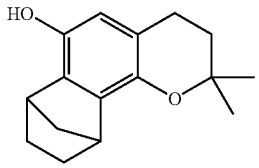

2,2-Dimethyl-3,4,7,8,9,10-hexahydro-7,10-methano-2H-benzo[h]chromen-6-ol; and

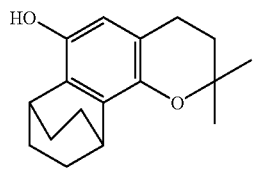

2,2-Dimethyl-3,4,7,8,9,10-hexahydro-7,10-ethano-2H-benzo[h]chromen-6-ol.

Particularly preferred are those methods of treatment and uses in the manufacture of pharmaceutical compositions therefor, wherein the compound is selected from the preferred compounds.

Another aspect of this invention is the processes for preparing compounds of Formula I, and is set forth in "Description of the Invention".

Certain embodiments of the invention provide novel and preferred combinations of substituent groups pendant from the formulae of the different inventions

DETAILED DESCRIPTION OF THE INVENTION

Definitions

As used in the present specification, the following words and phrases are generally intended to have the meanings as set forth below, except to the extent that the context in which they are used indicates otherwise.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined below.

It will be understood by those skilled in the art with respect to any group containing one or more substituents that such groups are not intended to introduce any substitution or substitution patterns that are sterically impractical and/or physically non-feasible.

The term "acyl" refers to the groups —C(O)—H, —C(O)-(optionally substituted alkyl), —C(O)-(optionally substituted cycloalkyl), —C(O)-(optionally substituted alkenyl), —C(O)-(optionally substituted cycloalkenyl), —C(O)-(optionally substituted aryl), and —C(O)-(optionally substituted heterocyclyl). This term is exemplified with groups as formyl, acetyl, 4-oxo4-yl-butiric acid.

The term "alkenyl" refers to a monoradical branched or unbranched, unsaturated or polyunsaturated hydrocarbon chain, having from about 2 to 20 carbon atoms, more preferably about 2 to 10 carbon atoms. This term is exemplified by groups such as ethenyl, but-2-enyl, 3-methyl-but-2-enyl (also referred to as "prenyl", octa-2,6-dienyl, 3,7-dimethyl-octa-2,6-dienyl (also referred to as "geranyl"), and the like.

The term "substituted alkenyl" refers to refers to an alkenyl group in which 1 or more (up to about 5, preferably up to about 3) hydrogen atoms is replaced by a substituent independently selected from the group: =O, =S, acyl, acyloxy, optionally substituted alkoxy, optionally substituted amino (wherein the amino group may be a cyclic amine), azido, carboxyl, (optionally substituted alkoxy)carbonyl, (optionally substituted amino)carbonyl, cyano, optionally substituted cycloalkyl, optionally substituted cycloalkenyl, optionally substituted heteroaryl, halogen, hydroxyl, nitro, sulfamoyl, sulfanyl, sulfinyl, sulfonyl, and sulfonic acid. Preferred examples of substituted alkenyl are 5-vinyl-thiazolidine-2,4-dione, 3-vinyl-3-H-benzofuran-2-one, 3-methyl-4-vinyl-5-oxo4,5-dihydropyrazol-1yl-benzoic acid, tetrahydropyran-4-ylidene-ethyl, 2-methyl4-vinyl-5-propyl-2,4-dihydro-pyrazol-3-one and cyclohexylidene-ethyl.

The term "acyloxy" refers to the moiety —O-acyl, including, for example, —O—C(O)-alkyl.

The term "alkoxy" refers to the groups —O-alkyl, —O-alkenyl, -0-cycloalkyl, -0-cycloalkenyl, and —O-alkynyl. Preferred alkoxy groups are —O-alkyl and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "substituted alkoxy" refers to the groups -O-(substituted alkyl), —O-(substituted alkenyl), —O-(substituted cycloalkyl), —O-(substituted cycloalkenyl), —O-(substituted alkynyl) and -O-(optionally substituted alkylene)-alkoxy.

The term "alkyl" refers to a monoradical branched or unbranched saturated hydrocarbon chain preferably having from about 1 to 20 carbon atoms, more preferably about 1 to 10 carbon atoms, and even more preferably about 1 to 6 carbon atoms. The term "alkyl" also means a combination of linear or branched and cyclic saturated hydrocarbon radical consisting solely of carbon and hydrogen atoms. This term is exemplified by groups such as methyl, ethyl, n-propyl, iso-propyl, n-butyl, iso-butyl, n-hexyl, n-decyl, tetradecyl, and the like. The term "lower alkyl refers to a monoradical branched or unbranched saturated hydrocarbon chain of 1 to 6 atoms.

The term "substituted alkyl" refers to an alkyl group in which 1 or more (up to about 5, preferably up to about 3) hydrogen atoms is replaced by a substituent independently selected from the group: =O, =S, acyl, acyloxy, optionally substituted alkoxy, optionally substituted amino (wherein the amino group may be a cyclic amine), azido, carboxyl, (optionally substituted alkoxy)carbonyl, (optionally substituted amino)carbonyl, cyano, optionally substituted cycloalkyl, optionally substituted cycloalkenyl, halogen, hydroxyl, nitro, sulfamoyl, sulfanyl, sulfinyl, sulfonyl, and sulfonic acid. One of the preferred optional substituents for alkyl is hydroxy, exemplified by hydroxyalkyl groups, such as 2-hydroxyethyl, 3-hydroxypropyl, 3-hydroxybutyl, 4-hydroxybutyl, and the like; dihydroxyalkyl groups (glycols), such as 2,3-dihydroxypropyl, 3,4-dihydroxybutyl, 2,4-dihydroxybutyl, and the like; aminoalkyl groups such as dimethyl aminoalkyl, piperidinylalkyl, morpholinylalkyl, and those compounds known as polyethylene glycols, polypropylene glycols and polybutylene glycols, and the like. Another preferred optional substituent for alkyl is sulfanyl exemplified by allylsulfanyl, carboxypropylsulfanyl, 2-methyl-propionyl-pyrrolidine-2-carboxylic acid, 5-methyl-1-H-benzimidazol-2-yl-sulfanyl, sulfoxyethylsulfanyl, 4,6-dimethyl-pyrimidin-2-ylsulfanyl, 4 carboxy-benzyl-sulfanyl, isobutylsulfanyl, and the like. Other preferred optional substituents for alkyl are —N-hydroxyureidyl, —N-hydroxythioureidyl or —N-hydroxyacetamide. Other preferred alkyl substituents are halogen exemplified by chloro and bromo, acyl exemplified by methylcarbonyl, alkoxy, and heterocyclyl exemplified by morpholino and piperidino.

The term "alkylene" refers to a diradical derived from the above-defined monoradical, alkyl. This term is exemplified by groups such as methylene (—CH$_2$—), ethylene (—CH$_2$CH$_2$—), the propylene isomers [e.g., —CH$_2$CH$_2$CH$_2$— and —CH(CH$_3$)CH$_2$—] and the like.

The term "substituted alkylene" refers to a diradical derived from the above-defined monoradical, substituted alkyl. Examples of substituted alkylenes are chloromethylene (—CH(Cl)—), aminoethylene (—CH(NH$_2$)CH$_2$—), methylaminoethylene (—CH(NHMe)CH$_2$—), 2-carboxypropylene isomers (—CH$_2$CH(CO$_2$H)CH$_2$—), ethoxyethylene (—CH$_2$CH$_2$O—CH$_2$CH$_2$—), ethyl(N-methyl)aminoethylene (—CH$_2$CH$_2$N(CH$_3$)CH$_2$CH$_2$—), 1-ethoxy-2-(2-ethoxyethoxy)ethylene (—CH$_2$CH$_2$O—CH$_2$CH$_2$—OCH$_2$CH$_2$—OCH$_2$CH$_2$—), and the like.

The term "Alzheimer's disease" ("AD") refers to a progressive disease of the human central nervous system. It is manifested by dementia in the elderly, by disorientation, loss of memory, difficulty with language, calculation, or visual-spatial skills, and by psychiatric manifestations. It is associated with degenerating neurons in several regions of the brain.

The term "amino" refers to the group —NH$_2$ as well as to the groups —NHR or —NRR where each R is independently selected from the group: optionally substituted alkyl, optionally substituted cycloalkyl, optionally substituted alkenyl, optionally substituted cycloalkenyl, optionally substituted alkynyl, optionally substituted aryl, optionally substituted heterocyclyl, acyl, optionally substituted alkoxy, carboxy and alkoxycarbonyl, and where —NRR may be a cyclic amine.

The term "amyotrophic lateral sclerosis" (ALS) is the name given to a complex of disorders that compromise upper and lower motor neurons. Patients may present with progressive spinal muscular atrophy, progressive bulbar palsy, primary lateral sclerosis, or a combination of these conditions. The term ALS includes all types of ALS and other motor neuron diseases of similar clinical presentation. Amyotrophic lateral sclerosis ("ALS"), is also known as Lou Gehrig's disease or Charcot syndrome. (htti://www.lougehrigsdisease.net).

The term "aromatic" refers to a cyclic or polycyclic moiety having a conjugated unsaturated (4n+2) π electron system (where n is a positive integer), sometimes referred to as a delocalized π electron system.

The term "aryl" refers to an aromatic cyclic hydrocarbon group of from 6 to 20 carbon atoms having a single ring (e.g., phenyl) or multiple condensed (fused) rings (e.g., naphthyl or anthryl). Preferred aryls include phenyl, naphthyl and the like.

The term "substituted aryl" refers to an aryl group as defined above, which unless otherwise constrained by the definition for the aryl substituent, is substituted with from 1 to 5 substituents, and preferably 1 to 3 substituents, independently selected from the group consisting of: hydroxy, thiol, acyl, acyloxy, optionally substituted alkenyl, optionally substituted alkoxy, optionally substituted alkyl (such as tri-halomethyl), optionally substituted alkynyl, optionally substituted amino, optionally substituted aryl, optionally substituted aryloxy, azido, carboxyl, (optionally substituted alkoxy)carbonyl, (optionally substituted amino)carbonyl, cyano, optionally substituted cycloalkyl, optionally substituted cycloalkenyl, halogen, optionally substituted heterocyclyl, optionally substituted heterocyclooxy, hydroxyl, nitro, sulfanyl, sulfinyl, sulfanyl, and sulfonic acid. Preferred aryl substituents include alkyl, alkenyl, alkoxy, halo, cyano, nitro, haloalkyl, carboxy, amino, amido, sulfonamido, and sulfinyl.

The term "carboxy" or "carboxyl" refers to the moiety "-C(O)OH", which is also illustrated as "—COOH".

The term "cognitive disorders" refers to disorders generally characterized by symptoms of forgetfulness, confusion, memory loss, impairment in attention and memory, behavioral and relation disorders, abulia, lack of interest, affective disturbances, and/or, in some cases poor personal care. These symptoms may arise as a result of the general aging process and/or from organic brain disease, cerebrovascular disease, head injury, or developmental or genetic defects. Cognitive disorders include Alzheimer's disease, senile dementia, anxiety, HIV-related dementia, diabetic neuropathies; depression; Parkinson's disease; drug dependency; substance abuse; consciousness disorders, sleeping disorders, disorders of the circadian rhythm, mood disorders, epilepsy; Down's syndrome; Huntington's chorea or disease; stress-related somatic disorders; Creutzfeldt-Jacob disease; disorders associated with panic, phobia or stress.

The term "convulsion" is used herein as meaning the violent involuntary contraction or repeated contractions of the voluntary muscles.

The term "cycloalkyl" refers to non-aromatic cyclic hydrocarbon groups of having about 3 to 40 (preferably about 4 to 15) carbon atoms having a single ring or multiple condensed or bridged rings. Such cycloalkyl groups include, by way of example, single ring structures such as cyclopropyl, cyclobutyl, cyclopentyl, cyclooctyl, and the like, or multiple ring structures such as adamantanyl, and the like. The term "cycloalkyl" additionally encompasses spiro systems wherein the cycloalkyl ring has a carbon ring atom in common with another ring.

The term "substituted cycloalkyl" refers to a cycloalkyl group substituted with from 1 to 5 substituents, and preferably 1 to 3 substituents, independently selected from the group consisting of: =O, =S, acyl, acyloxy, optionally substituted alkenyl, optionally substituted alkoxy, optionally substituted alkyl (such as tri-halomethyl), optionally substituted alkynyl, optionally substituted amino, optionally substituted aryl, optionally substituted aryloxy, azido, carboxyl, (optionally substituted alkoxy)carbonyl, (optionally substituted amino)carbonyl, cyano, optionally substituted cycloalkyl, optionally substituted cycloalkenyl, halogen, optionally substituted heterocyclyl, optionally substituted heterocyclooxy, hydroxyl, nitro, sulfanyl, sulfinyl, sulfanyl, and sulfonic acid. A cycloalkyl ring substituted with an alkyl group is also referred as "alkylcycloalkyl".

The term "epilepsy" is used herein in its broadest sense, for example, as inclusive of grand mal, petit mal, and psychic equivalent or psychomotor attacks.

The term "Friedreich's ataxia" as used herein also includes other ataxias, and is also sometimes referred to as hereditary ataxia, familiar ataxia, or Friedreich's tabes. Friedreich's ataxia is an autosomal recessive multi-system degenerative disorder disease that results in progressive damage to the nervous system and causes symptoms ranging from muscle weakness and speech problems to heart disease.

The term "halo" or "halogen" refers to fluoro, chloro, bromo and iodo.

The terms "heterocycle", "heterocyclic", "heterocyclo", and "heterocyclyl" refer to a monovalent, saturated, partially unsaturated or unsaturated (aromatic), carbocyclic radical having one or more rings incorporating one, two, three or four heteroatoms within the ring (chosen from nitrogen, oxygen, and/or sulfur). Preferred heterocycles include morpholine, piperidine, piperazine, thiazole, thiazolidine, isothiazole, oxazole, isoxazole, pyrazole, pyrazolidine, pyrazoline, imidazole, imidazolidine, benzothiazole, pyridine, pyrazine, pyrimidine, pyridazine, pyrrole, pyrrolidine, quinoline, quinazoline, purine, carbazole, benzimidazole, pyrimidine, thiophene, benzothiophene, pyran, tetrahydropyran, benzopyran, furan, tetrahydrofuran, indole, indoline, indazole, xanthene, thioxanthene, acridine, quinuclidine, and the like.

The terms "substituted heterocycle", "substituted heterocyclic", "substituted heterocyclo" and "substituted heterocyclyl" refer to a heterocycle group as defined above, which unless otherwise constrained by the definition for the heterocycle, is substituted with from 1 to 5 substituents, and preferably 1 to 3 substituents, independently selected from the group consisting of: hydroxy, thiol, acyl, acyloxy, optionally substituted alkenyl, optionally substituted alkoxy, optionally substituted alkyl (such as tri-halomethyl), optionally substituted alkynyl, optionally substituted amino, optionally substituted aryl, optionally substituted aryloxy, azido, carboxyl, (optionally substituted alkoxy)carbonyl, (optionally substituted amino)carbonyl, cyano, optionally substituted cycloalkyl, optionally substituted cycloalkenyl, halogen, optionally substituted heterocyclyl, optionally substituted heterocyclooxy, hydroxyl, nitro, sulfanyl, sulfinyl, and sulfonic acid. Preferred substituted heterocycles include pyrrolidine 2-carboxylic acid, thiazolidine-2,4-dione and 3-methyl-5-oxo-4,5-dihydro-1H-pyrazol.

The term "inflammation", "inflammatory conditions", or "inflammation conditions" includes but is not limited to muscle fatigue, osteoarthritis, rheumatoid arthritis, inflammatory bowel syndrome or disorder, skin inflammation, such as atopic dermatitis, contact dermatitis, allergic dermatitis, xerosis, eczema, rosacea, seborrhea, psoriasis, atherosclerosis, thermal and radiation burns, acne, oily skin, wrinkles, excessive cellulite, excessive pore size, intrinsic skin aging, photo aging, photo damage, harmful UV damage, keratinization abnormalities, irritation including retinoid induced irritation, hirsutism, alopecia, dyspigmentation, inflammation due to wounds, scarring or stretch marks, loss of elasticity, skin atrophy and gingivitis.

The term "ischemia" refers to deficiency of blood to an organ or tissue due to functional constriction or actual obstruction of a blood vessel. Cerebral ischemia, also known as stroke, usually results from the interruption or reduction of blood and oxygen to the blood vessels of the brain; more rarely this may be the result of a hemorrhage. Signs of stroke include paralysis, slurred speech, general confusion, impairment of gait, cortical sensory loss over toes, foot and leg, and urinary incontinence, to name just a few. Many types of heart disease including cardiac arrhythmias or diseases due to cardiac structural abnormalities may produce cerebral emboli. Atrial fibrillation from any cause, including rheumatic valvular disease, may result in emboli being produced which can migrate into the arteries of the brain. Emboli formation and migration can occur as a result of atherosclerotic cardiovascular disease and myocardial infarction. Emboli formation is also a definite risk for intracardiac surgery and prosthetic valve replacement. Heart bypass surgery and angioplasty can result in the formation of microemboli which can migrate into the arteries of the brain and cause a series of occlusions in a number of arteries, resulting in mental impairment. Cerebral embolism is also the principal complication in the transplant of artificial hearts. Furthermore, the overall risk of stroke after any type of general surgery is 0.2 to 1 percent. The vegetations of acute and subacute bacterial endocarditis can give rise to emboli which can occlude a major intracranial artery. Populations at risk of ischemia include but are not limited to patients scheduled for coronary arterial bypass graft surgery (CABG), patients at risk for postoperative complications, patients with subarachnoid hemorrhage (SAH), patients with a first or second ischemic stroke, patients with acute ischemic stroke, patients undergoing cardiopulmonary resuscitation (CPR), patients with temporary lobotomy, patients with dominant hemisphere resection, patients receiving prophylactic brain radiation, patients with closed head trauma with neurological loss, patients with microvascular multi-infarct dementia, patients with homozygous and heterozygous MELAS (Mitochondrial myopathy, encephalopathy, lactacidosis, stroke); patients with Myoclonic Epilepsy with Ragged Red Fibers (MERFF); patients with atherosclerotic or progressive supranuclear palsy disease, patients with symptomatic and asymptomatic Huntington's disease, patients with neonatal asphyxia, patients with meningitis or encephalitis, patients with post herpetic neuropathy, patients with intermittent claudication, patients with spinal cord injury, patients with Huntington's disease, Amyotrophic Lateral Sclerosis (ALS) or Friedreich's ataxia, patients with diabetic neuropathy or patients with a disease associated with a hypercoagulable state secondary to systemic disease, carcinoma, vasoconstriction (including reversible cerebral vasoconstriction, e.g. migraine, trauma, idiopathy), or venous conditions (including dehydration, pulmonary embolism, pericranial infection, postpartum and postoperative states and system cancer).

The term "isomers" or "stereoisomers" relates to compounds that have identical molecular formulae but that differ in the arrangement of their atoms in space. Stereoisomers that are not mirror images of one another are termed "diastereoisomers" and stereoisomers that are non-superimposable mirror images are termed "enantiomers", or sometimes optical isomers. A carbon atom bonded to four non-identical substituents is termed a "chiral center". Certain compounds of the present invention have one or more chiral centers and therefore may exist as either individual stereoisomers or as a mixture of stereoisomers. This invention includes all possible stereoisomers as individual stereoisomers or as a mixture of stereoisomers.

A "lipoxygenase-mediated condition" or a "disorder mediated by lipoxygenases" refers to a condition, disorder or disease related to or otherwise associated with a lipoxygenase enzyme or the inhibition thereof, including, by way of example and without limitation, diseases involving apoptosis in cancer cells such as prostatic cancer, gastric cancer, colorectal or esophageal cancer and airways carcinoma; diseases involving hypoxia, or anoxia such as atherosclerosis, myocardial infarction, cardiovascular disease, heart failure (including chronic and congestive heart failure), cerebral ischemia, retinal ischemia, myocardial ischemia, post surgical cognitive dysfunction and other ischemias; diseases involving inflammation, including diabetes, arterial inflammation, inflammatory bowel disease, renal disease, pre-menstrual syndrome, asthma, allergic rhinitis, gout; cardiopulmonary inflammation, rheumatoid arthritis, osteoarthritis, muscle fatigue and disorders of the skin such as acne; disorders of the airways such as asthma, chronic bronchitis, human airway carcinomas, mucus hypersecretion, chronic obstructive pulmonary disease (COPD) and adult respiratory distress syndrome; diseases involving neurodegeneration and neuroinflammation including Alzheimer's, dementia and Parkinson's disease; peripheral neuropathy including spinal chord injury, head injury and surgical trauma, and allograft tissue and organ transplant rejection; diseases involving the autoimmune system such as psoriasis, eczema, rheumatoid arthritis, and diabetes; and disorders involving the bone loss or bone formation.

The term "macular degeneration" includes an ophthalmic (eye) condition characterized by progressive destruction and dysfunction of the central retina (macula), and includes diseases that are all characterized by a progressive loss of central vision. This term comprises age-related macular degeneration (AMD). Age-related macular degeneration (AMD) is a collection of clinically recognizable ocular findings including drusen, retinal pigment epithelial (RPE) disturbance, pigment clumping and/or dropout, RPE detachment, geographic atrophy, subretinal neovascularization and disciform scar. Not all these manifestations are needed for AMD to be considered present.

The term "mitochondrial diseases or disorders" of which hundreds of varieties have been identified—can cause a complex variety of symptoms. These include muscle weakness, muscle cramps, seizures, food reflux, learning disabilities, deafness, short stature, paralysis of eye muscles, diabetes, cardiac problems and stroke-like episodes, to name a few. The symptoms can range in severity from life-threatening to almost unnoticeable, sometimes taking both extremes in members of the same family. Because some people have specific subsets of these symptoms, clinical researchers have grouped those that occur together into "syndromes," producing a bewildering array of descriptive acronyms such as MELAS (mitochondrial encephalomyopathy with lactic acidosis and stroke-like episodes) or MERFF (myoclonus epilepsy with ragged red fibers). This term also includes disorders such as Kearns-Sayre syndrome (KSS), Leigh's syndrome, maternally inherited Leigh's syndrome (MILS), myogastrointestinal encephalomyopathy (MNGIE), Neuropathy, ataxia and retinitis pigmentosa (NARP), Progressive external ophthalmoplegia (PEO), and Pearson syndrome.

Mitochondrial myopathy, encephalopathy, lactacidosis, stroke ("MELAS") is a progressive neurodegenerative disorder. The typical presentation of patients with MELAS syndrome includes features that comprise the name of the disorder such as mitochondrial encephalomyopathy, lactic acidosis, and stroke like episodes. Other features, such as diabetes mellitus and hearing loss, clearly are part of the disorder. MELAS is characterized by stroke-like episodes and a mitochondrial myopathy.

The term "neurodegenerative disorders" refers to disorders characterized by a loss of neurons and may or may not include a neuroinflammatory process. Neurodegenerative disorders include stroke, head trauma, cerebral hypoxia, spinal cord injury, senile dementia, Alzheimer's disease, amyotrophic lateral sclerosis (ALS) and other motor neuron diseases, cerebral amyloid angiopathy, HIV-related dementia, Parkinson's disease, Huntington's disease, prion diseases, myasthenia gravis, Down's syndrome, Creutzfeldt-Jakob disease, Friedreich's ataxia, Fergusson and Critchley's ataxia and other ataxias, Leber's hereditary optic neuropathy diabetic neuropathy, neuropathic pain, encephalitis, meningitis, and Duchenne's muscular dystrophy.

The term "neuroinflammation" or "neuroinflammatory diseases, disorders or conditions" refers to diseases, disorders or conditions characterized by large numbers of reactive microglia in postmortem brain samples, indicative of an active inflammatory process (McGeer E. G. and McGeer P. L., "Neurodegeneration and the immune system". Caine D. B., ed. Neurodegenerative Diseases, 1994:277-300). Neuroinflammation refers to inflammation which occurs in response to brain injury or autoimmune disorders, and has been shown to cause destruction of healthy neuronal and/or cerebral tissue. Neuroinflammation relates to mechanisms implicated in a broad range of acute and chronic neurodegenerative disorders, including stroke, head trauma, cerebral amyloid angiopathy, HIV-related dementia, Huntington's disease, prion diseases, meningitis, myelin degradation, epilepsy, Down's syndrome, post-ischemic brain injury, encephalopathy, Parkinson's disease, senile dementia, Alzheimer's disease, amyotrophic lateral sclerosis, multiple sclerosis and certain disorders involving the peripheral nervous system, such as myasthenia gravis and Duchenne's muscular dystrophy.

The terms "Parkinson's", "Parkinsonism" and "Parkinsonian syndrome" ("PD") as used herein include not only Parkinson's disease but also drug-induced Parkinsonism and post-encephalitic Parkinsonism. Parkinson's disease is also known as paralysis agitans or shaking palsy. It is characterized by tremor, muscular rigidity and loss of postural reflexes. The disease usually progresses slowly with intervals of 10 to 20 years elapsing before the symptoms cause incapacity. Due to their mimicry of effects of Parkinson's disease, treatment of animals with methamphetamine or MPTP has been used to generate models for Parkinson's disease. These animal models have been used to evaluate the efficacy of various therapies for Parkinson's disease.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "pharmaceutically acceptable salt" refers to salts which retain the biological effectiveness and properties of the compounds of this invention and which are not biologically or otherwise undesirable. In some cases, the compounds of this invention are capable of forming acid and/or base salts by virtue of the presence of amino and/or carboxyl groups or groups similar thereto. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl)amines, alkenyl amines, dialkenyl amines, trialkenyl amines, substituted alkenyl amines, di(substituted alkenyl)amines, tri(substituted alkenyl) amines, cycloalkyl amines, di(cycloalkyl)amines, tri(cycloalkyl)amines, substituted cycloalkyl amines, disubstituted cycloalkyl amine, trisubstituted cycloalkyl amines, cycloalkenyl amines, di(cycloalkenyl)amines, tri(cycloalkenyl) amines, substituted cycloalkenyl amines, disubstituted cycloalkenyl amine, trisubstituted cycloalkenyl amines, aryl amines, diaryl amines, triaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heterocyclic, and the like. Also included are amines where the two or three substituents, together with the amino nitrogen, form a heterocyclic group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The term "seizure" is used herein as meaning the physical affliction characterized by transient clouding of consciousness, generally associated with a disturbance in the electrical activity of the cortex of the brain. Illustrative of such seizures are those associated with petit mal epilepsy.

The term "sulfanyl" or "thiol" refers to the groups: —S-(optionally substituted alkyl), —S-(optionally substituted aryl), —S-(optionally substituted heterocyclyl). Preferred sulfanyl groups include, by way of example, allylsulfanyl (—SCHCH$_2$=CH$_2$), n-(iso-butylsulfanyl) (—SCH$_2$CH (CH$_3$)$_2$), 3-thiazol-2-ylsulfanyl, captopril, 3-carboxy-2-methylpropylsulfanyl, and the like.

The term "sulfonic acid" refers to the group: —S(O$_2$)—OH.

The term "therapeutically effective amount" refers to that amount of a compound of this invention that is sufficient to effect treatment, as defined below, when administered to a mammal in need of such treatment. The therapeutically effective amount will vary depending upon the subject and disease condition being treated, the weight and age of the subject, the severity of the disease condition, the particular compound chosen, the dosing regimen to be followed, timing of administration, the manner of administration and the like, all of which can readily be determined by one of ordinary skill in the art.

The term "treatment" or "treating" means any treatment of a disease or disorder in a mammal, including:
preventing or protecting against the disease or disorder, that is, causing the clinical symptoms not to develop;
inhibiting the disease or disorder, that is, arresting or suppressing the development of clinical symptoms; and/or
relieving the disease or disorder that is, causing the regression of clinical symptoms.

It will be understood by those skilled in the art that in human medicine, it is not always possible to distinguish between "preventing" and "suppressing" since the ultimate inductive event or events may be unknown, latent, or the patient is not ascertained until well after the occurrence of the event or events. Therefore, as used herein the term "prophylaxis" is intended as an element of "treatment" to encompass both "preventing" and "suppressing" as defined herein. The term "protection," as used herein, is meant to include "prophylaxis."

Nomenclature

In general, the nomenclature used in this Application was generated with the help of version 2.2 of the AUTONOM™ naming package within the ChemOffice® version 7.0.3 suite of programs by CambridgeSoft Corp (Cambridge, Mass.).

A compound of Formula I wherein V is bicyclo[2.2.1] heptane, -A-B— is —CH$_2$—CH$_2$—, n is 2, R$^1$ is methyl, R$^2$ is —C(O)OCH$_3$, R$^3$ and R$^4$ are hydrogen is named 3-(6-Hydroxy-2-methyl-3,4,7,8,9,10-hexahydro-7,10-methano-2H-benzo[h]chromen-2-yl)-propionic acid methyl ester.

Synthesis of the Compounds of the Invention

Synthetic Reaction Parameters

The terms "solvent", "inert organic solvent" or "inert solvent" mean a solvent inert under the conditions of the reaction being described in conjunction therewith. Solvents employed in synthesis of the compounds of the invention include, for example, methanol ("MeOH"), acetone, water, acetonitrile, 1,4-dioxane, dimethylformamide ("DMF"), benzene, toluene, tetrahydrofuran ("THF"), chloroform, methylene chloride (also named dichloromethane( ("DCM"), diethyl ether, ethyl acetate ("EtOAc"), pyridine and the like, as well as mixtures thereof. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

Unless specified to the contrary, the reactions described herein take place at atmospheric pressure within a temperature range from 0° C. to 110° C. (preferably from 0° C. to 25° C.; most preferably at "room" or "ambient" temperature ("RT"), e.g., 20° C.). Further, unless otherwise specified, the reaction times and conditions are intended to be approximate, e.g., taking place at about atmospheric pressure within a temperature range of about 0° C. to about 110° C. (preferably from about 0° C. to about 25° C.; most preferably at about "room" or "ambient" temperature, e.g., approximately 20° C.) over a period of about 1 to about 10 hours (preferably about 5 hours).

Isolation and purification of the compounds and intermediates described herein can be effected, if desired, by any suitable separation or purification procedure such as, for example, filtration, extraction, crystallization, column on silica gel, thin-layer chromatography on silica gel or thick-layer chromatography on silica gel, or a combination of these procedures. Specific illustrations of suitable separation and isolation procedures can be had by reference to the examples herein below. However, other equivalent separation or isolation procedures can also be used.

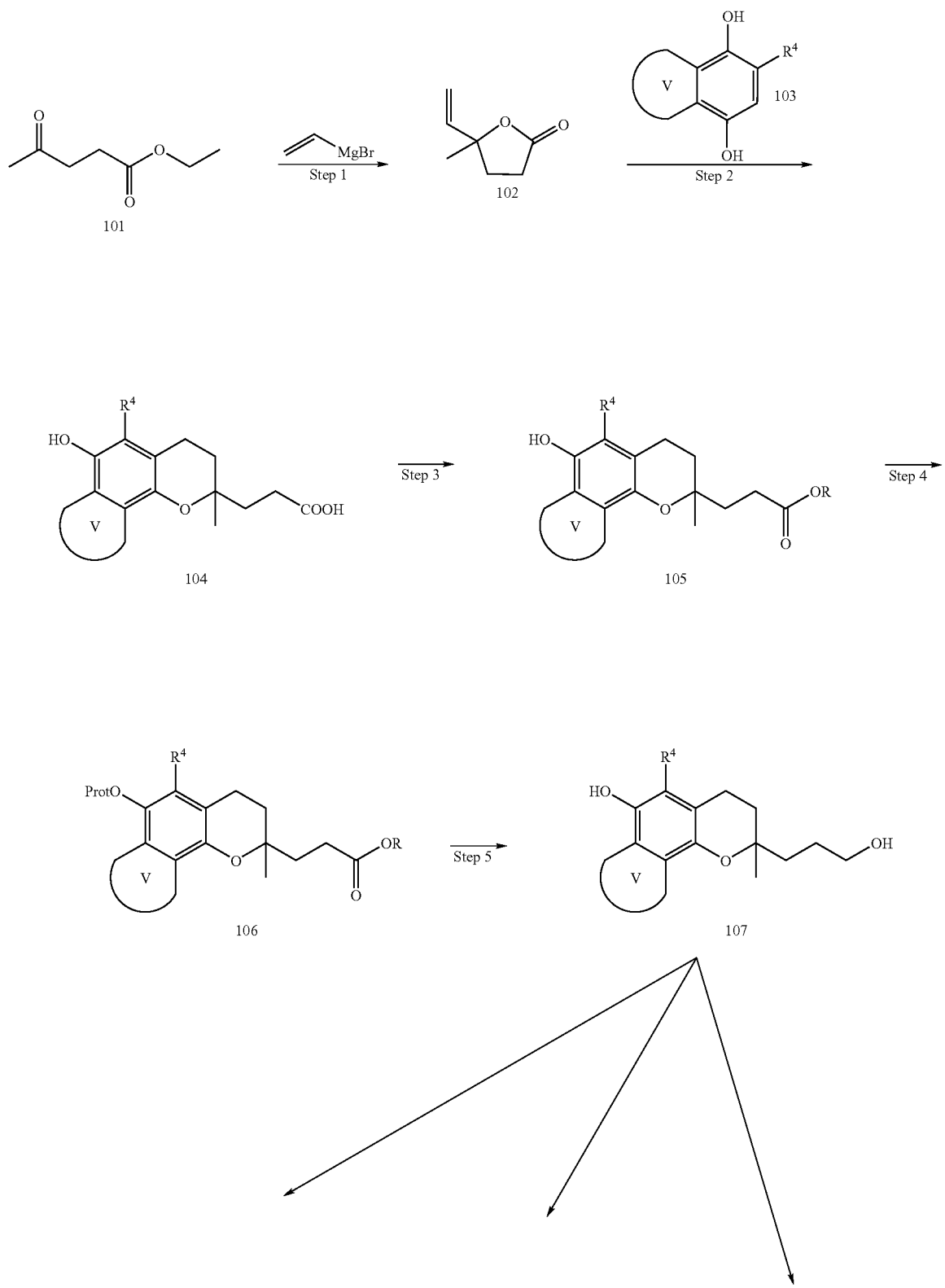

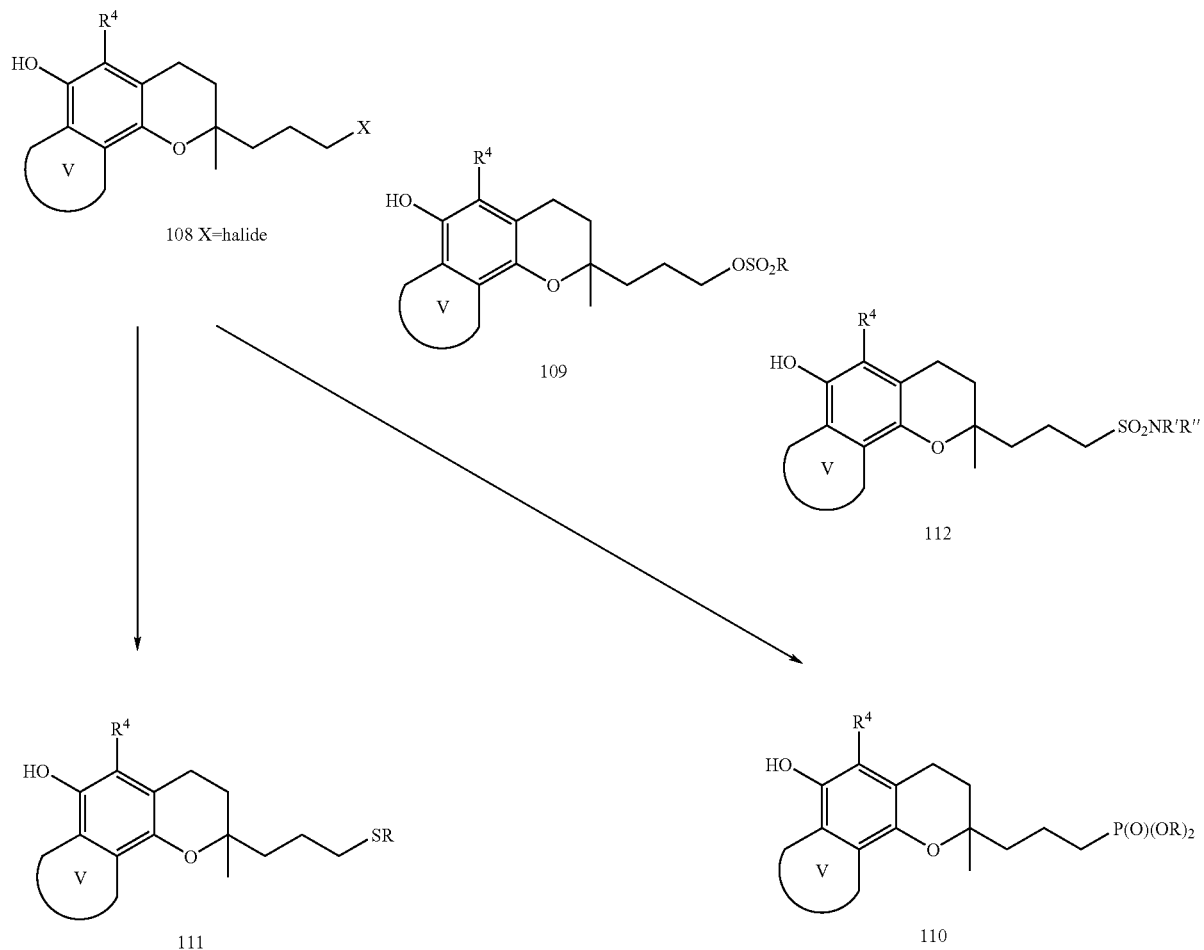

Referring to Reaction Scheme 1, ethyl 2-ketopentoate (Formula 101) undergoes a Grignard reaction with vinylmagnesium bromide to give a furanone of Formula 102. The hydroquinone derivative of Formula 103 wherein $R^4$ is hydrogen and V is a bicyclo[2.2.1]heptane ring used in Step 2 is available commercially from TCI, Portland, Oreg. or from Fisher Scientific, Somerville, N.J. Other hydroquinone derivatives of Formula 103 can be prepared by methods known to those of ordinary skill in the art, by Diels Adler reaction of a quinone and a cyclohexadiene. Reaction of compound 103 with the vinyl furanone of Formula 102, in the presence of boron trifluoride in an inert solvent such as dioxane gives the acid of Formula 104. Esterification in Step 3 to the corresponding compound of Formula 105 can be done under conditions well known in the art, such as with an alcohol in the presence of an acid such as hydrochloric acid. In Step 4, the hydroxyl group is protected with, for example, chloromethyl methyl ether in the presence of a base such as diisopropylethylamine in solvent such as methylene chloride, and the protected ester of Formula 106 is reduced and deprotected to give the alcohol of Formula 107. The reducing agents that can be used include lithium aluminum hydride, lithium borohydride or sodium borohydride in an organic solvent such as tetrahydrofuran (THF) or diethylether. Deprotection can be done with an acid such as hydrochloric acid in a solvent such as methanol. In methods well known to the skilled practitioner the alcohol derivative of Formula 107 can be converted into, for example, a halide of Formula 108, a sulfonate of Formula 109, a phosphonate of Formula 110, a thiol of Formula 111, or a sulfonamide of Formula 112, as exemplified in the examples. In the reaction scheme described above, V, R, R', R" and $R^4$ have the meanings defined supra.

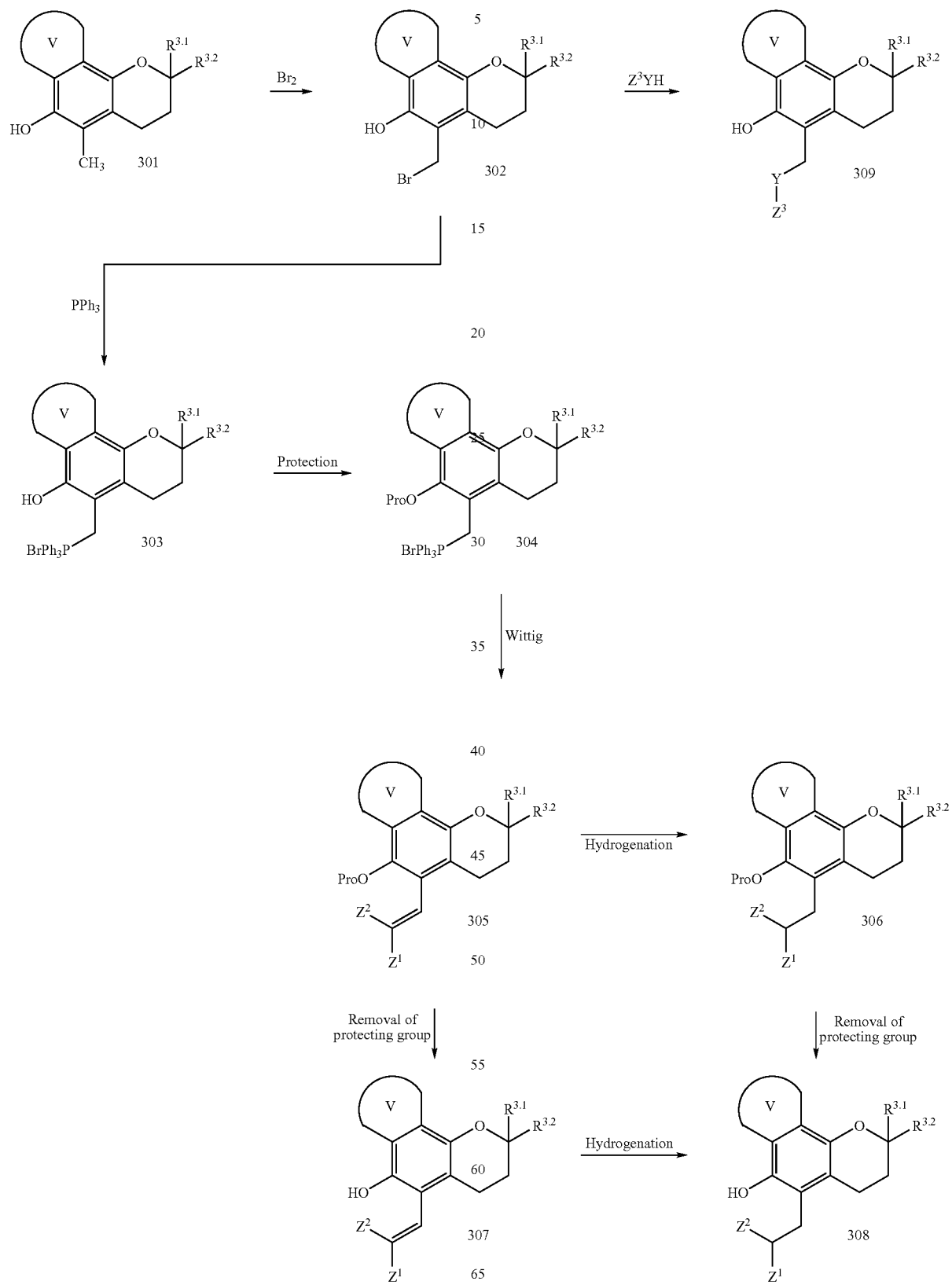

Compounds of Formula I wherein the 5-position is substituted with a substituted alkyl of at least two carbons or a substituted alkenyl, can be prepared following Scheme 3. In Scheme 3, $R^{3.1}$ and $R^{3.2}$ are hydrocarbon groups, preferably unsubstituted alkyl groups, V has the meaning of a bicyclic ring as defined in Formula I. Pro is a protective group and $Z^1$ and $Z^2$ are the substituents of interest for the alkyl group at the 5 position, or $Z^1$ is hydrogen and $Z^2$ is the substituent of interest for the alkyl group.

The chroman of Formula 301 is brominated in an inert solvent to give the methylbromide derivative 302, which is then converted to the phosphonium salt of Formula 303 by addition of triphenylphosphine. The hydroxy group of the phosphonium salt derivative 303, can be protected with for example, the methoxymethyl (MOM) group by reaction with chloromethylmethyl ether to give a MOM-protected compound of Formula 304. In the next step a Wittig reaction is performed with an aldehyde or a ketone of formula $Z^1Z^2C$(O), in an inert solvent in the presence of a strong base, such as sodium alkoxide or sodium hydride, preferably sodium hydride to give a compound of Formula 305. Hydrogenation of the double bond of compound of Formula 305 in a hydrogen atmosphere in the presence of a catalyst such as Palladium on charcoal can yield compound of Formula 306, which after removal of the protective group can give the desired saturated compound of Formula 308. Removal of the protecting group can be effected with an acid such as hydrochloric acid in a solvent such as an alcohol, preferably in methanol. Deprotection of compound of Formula 305 with an acid can give the unsaturated compound of Formula 307, which if desired, can also be hydrogenated to give the compound of Formula 308, under the conditions described herein.

Alternatively, the chromans of Formula 301, wherein $R^{3.1}$ and $R^{3.2}$ have respectively the meaning of $R^1$ and $(CH_2)_nR^2$ of Formula I as defined supra, and further wherein V has the meaning of a bicyclic ring as defined in Formula I, can be brominated as described herein to give a bromide derivative of Formula 302, which followed by the treatment with a compound of Formula $Z^3YH$ wherein Y is oxygen, sulfur or nitrogen and $Z^3$ is the desired substituent, in the presence of a mild base such as sodium or potassium carbonate, sodium or potassium bicarbonate, in an inert solvent, preferably methylene chloride, can give a compound of Formula 309.

Preferred Compounds

The compounds of Formula I encompass the chroman derivatives of the invention as disclosed, and/or the pharmaceutically acceptable salts of such compounds. In addition, the compounds of this invention include the individual stereochemical isomers and mixtures thereof, arising from the selection of substituent groups. For Example, 3-(6-hydroxy-2-methyl-3,4,7,8,9,10-hexahydro-7,10-methano-2H-benzo[h]chromen-2-yl)-propionic acid exists as 4 single stereoisomers:

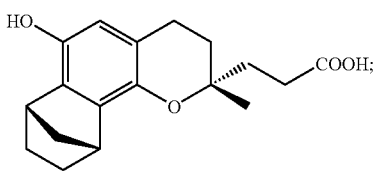

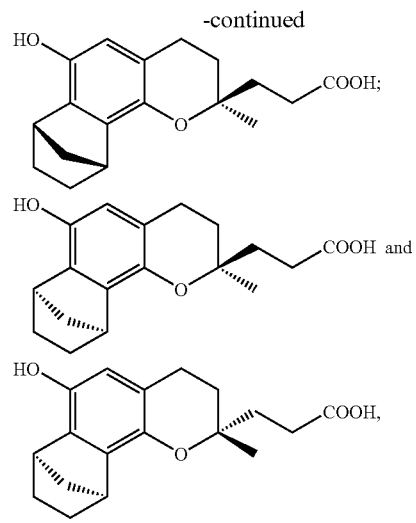

and the chemical name 3-(6-hydroxy-2-methyl-3,4,7,8,9,10-hexahydro-7,10-methano-2H-benzo[h]chromen-2-yl)-propionic acid as used herein includes all 4 stereoisomers individually or as mixtures of stereoisomers. The mixture of stereoisomers can be separated into their individual stereoisomers by procedures well known in the art such as for example chiral chromatography.

It will be understood by those skilled in the art with respect to any group containing one or more substituents that such groups are not intended to introduce any substitution or substitution patterns that are sterically impractical and/or synthetically non-feasible.

Preferred for the compounds, pharmaceutical formulations, methods of manufacture and use of the present invention are the following combinations and permutations of substituent groups of Formula I.

Utility, Testing and Administration

General Utility

Compound, compositions, formulations, and methods of the present invention can be used for the treatment of disorders characterized by neuroinflammation, neurodegeneration, defective mitochondrial activity, oxidative stress and inflammation. In particular, compounds of the present invention can be used in the treatment of stroke or of neurodegeneration caused by stroke, particularly for the reduction of edema in the brains of stroke patients. Compounds of the present invention can also be used in the treatment of diseases such as degenerative diseases of the brain ((Wernicke-Korsakoff disease, Kreuzfeldt-Jakob disease (KJD), Hallervorden-Spatz disease, Schilder's disease, Alzheimer's disease, senile dementia, Down's syndrome in middle age, Abercrombie's disease, Prion diseases, Zellweger syndrome, Alper's Syndrome), spinocerebellar degenerations (spinal ataxia, cerebellar cortical degenerations, Friedreich's ataxia and other ataxias), multiple system degenerations (Menzel, Dejerine-Thomas, Shy-Drager, and Machado Joseph), systemic disorders (Refsum disease, ataxia telangiectasia), epilepsy, mitochondrial disorders (MELAS, MERFF, KSS, Leigh's, MILS, MNGIE, NARP, PEO, Pearson), demyelinating core disorders (multiple sclerosis, acute transverse myelitis), muscular atrophies (amyotrophic lateral sclerosis (ALS), multiple sclerosis (MS), infantile spinal muscular atrophy, Huntington's disease, spinobulbar atrophy (SBA), juvenile spinal muscular atrophy, myasthenia gravis and other motor neuron diseases), movement disorder (drug-induced Parkinsonism or Parkinson's disease), retinopathy (Leber's hereditary optic neuropathy, age-related macular degeneration (AMD), cataracts), cerebral ischemia ("stroke" most often caused by thrombosis, vasoconstriction and embolism), myocardial ischemia (including chronic stable angina, angina pectoris, unstable angina and Prinzmetal's angina, silent ischemia, reinfarction, reocclusion, restenosis, myocardial infarction and other forms of heart disease), diabetes, renal disease, pre-menstrual syndrome (PMS), asthma, cardiopulmonary inflammatory disorders, chronic heart failure, rheumatoid arthritis, muscle fatigue, irritable bowel syndrome, inflammatory bowel disease, intermittent claudication and for the preservation of allograft tissue for transplantation. Certain compounds of the present invention can also be useful in treating conditions falling with the group of dermatologic conditions, in particular prevention and protecting skin tissue against age-related damage or damage resulting from insults such as harmful ultraviolet (UV) radiation, stress and fatigue, and in the treatment of contact dermatitis, skin irritation, skin pigmentation, psoriasis, or acne.

Without subscribing to a particular theory or mechanism of action, compounds of the invention may target certain enzymes known as "oxidoreductases" that function widely across a variety of physiological processes; more particularly certain compounds of the present invention may target lipoxygenases such as 5-lipoxygenase, 15 lipoxygenase and/or 12/15-lipoxygenase. In particular, oxidoreductases catalyze reactions in which two molecules interact so that one molecule is oxidized and the other is reduced. Abnormalities in oxidoreductase activity may underlie such disorders as congestive heart failure, respiratory chain defects (e.g., abnormalities associated with enzymes of the respiratory chain, acute respiratory distress syndrome (ARDS)), glycogen storage disease, end-stage renal disease, and rheumatoid arthritis. Inhibitors of lipoxygenases are known to be useful in the prevention or treatment of for example, asthma, arthritis, chronic obstructive pulmonary disease (COPD), osteoarthritis, psoriasis, diabetes, ulcers, bone loss, atherosclerosis, and myocardial infarction.

Testing

This section describes how compositions incorporating compositions of the present invention are selected, using in vitro and/or in vivo models, for example, and used as therapeutic interventions in the exemplary indications, i.e., stroke, epilepsy, Parkinson's disease, Friedreich's ataxia, MELAS, macular degeneration, ALS, and Alzheimer's disease.

MPTP/MPP$^+$-induced neurodegeneration of dopaminergic neurons is a well characterized model which is therefore widely used to understand the pathogenesis of Parkinson's disease. The compounds were tested against MPTP/MPP$^+$ induced neuronal death in vitro and in vivo as shown in the following examples. In vitro evaluation of protection against mitochondrial dysfunction is carried out using substantia nigra-derived dopaminergic progenitor cell line (as described in Son J H, et al J W. (1999) *J Neurosci*, 19: 10-20), exposed to 1-methyl4-phenylpyridinium (MPP$^+$). In vivo evaluation was carried out using mice that had been treated with 1-methyl4-phenyl-1,2,3,6-tetrahydropyridine (MPTP), a neurotoxin. MPTP is metabolized by astrocytes into 1-methyl4-phenylpyridinium (MPP$^+$), a substrate for the dopamine transporter which then selectively inhibits complex 1 of the mitochondrial electron transport chain. This results in depletion of ATP, the production of reactive oxygen species and, consequently cell death. In a number of species, including humans, non-primates and rodents, MPTP produces an irreversible and severe parkinsonian syndrome which includes virtually all the clinical features of the disease. The striking pathologic and clinical similarities between idiopathic Parkinson's disease and MPTP-induced Parkinsonism suggest that the two disorders share common pathogenic mechanism.

A cellular assay using FRDA-patient derived fibroblasts (as described by Jauslin, M L et al, Human Molecular Genetics 11; 3055-3063 (2002)); was used to determine the protective effects of the test compounds by analyzing survival of dermal fibroblasts taken from FRDA patients and unaffected normal donors under conditions of partial GSH depletion. Exposure of FRDA fibroblasts to BSO (L-buthionine (S,R)-sulfoximine) under conditions of restricted selenium causes depletion of cellular glutathione (GSH) and severe plasma membrane damage leading to cell death. Pre-incubation with the test compounds before the addition of BSO was used to determine if they could protect FRDA cells from BSO-mediated cell death.

In experiments carried out in support of the present invention according to methods detailed in the Examples, anoxia/ischemia was induced in primary cultures of hippocampal neuronal cells, oxidative stress was induced in a neuronal cell line, and compounds were tested for their ability to prevent cell death. Using in vitro assays the potency and efficacy of test articles against redox injury and cell death can be established in a high throughput manner and the compounds found to have activity in those in vitro assays are then further tested in one or more animal models of cerebral ischemia ("stroke"), such as the middle cerebral artery occlusion (MCAO) model in rats.

Primary embryonic hippocampal neuronal cells are widely recognized as useful in models of neuronal function. Briefly, primary cultures of hippocampal neurons are used to test compounds for activity in neuronal protection. Hippocampal cultures are typically prepared from 18- to 19-day fetal rats. At this age, the generation of pyramidal neurons, which begins in the rat at about E15, is essentially complete. The brain tissue at this stage is relatively easy to dissociate, the meninges are removed readily, and the number of glial cells still is relatively modest (Park L C, Calingasan N Y, Uchida K, Zhang H, Gibson G E. (2000). Metabolic impairment elicits brain cell type-selective changes in oxidative stress and cell death in culture. *J Neurochem* 74(1):114-124). In order to evaluate the activity of compounds of the present invention, a test compound is assessed for its ability to protect cells against beta-amyloid induced oxidative stress in hippocampal neurons, as detailed in Examples.

Protection against redox stress can be further evaluated in cell culture using high glutamate induced oxidative stress (HGOS) in mouse dopaminergic cell lines. The cytotoxic effect of glutamate is not due to excitotoxicity, as this cell line is devoid of inotropic glutamate receptors. Rather, the glutamate-induced toxicity of dopaminergic cells is associated with an inhibition of cystine transport which subsequently leads to depletion of intracellular glutathione (GSH) levels (Murphy T. H., et al. Neuron 2, 1547-1558, 1989), activation of neuronal 12-lipoxygenase (Li, Y. et al., *Neuron* 19,453 463, 1997), increased ROS production (Tan S. et al., *J. Cell Biol.* 141,1423-1432, 1998) and elevated intracellular $Ca^{2+}$ (Li, Y. et al., see supra). Some molecules were measured for their ability to protect cells against glutamate-induced stress and the assay is detailed in Examples.

Further validation of neuroantiinflammatory activity of compounds can be assessed in vitro by the inhibition of IL-1.beta. release from a microglial cell line.

Interleukin-1 (IL-1) is a proinflammatory cytokine that exists in two separate forms that share 30% sequence homology (alpha and beta). Constitutive expression of IL-1 is low in the brain but levels of both forms of this cytokine increase dramatically after injury. There is substantial evidence that IL-1 is an important mediator of neurodegeneration induced by cerebral ischemia (Touzani O et al, *J Neuroimmunol.*, 100:203-215, (1999)). Both IL-1 forms are rapidly induced in experimental models of stroke and administration of recombinant IL-1 beta enhances ischemic injury (see Hill J K. et al. *Brain Res.* 820:45-54, (1999), Hillhouse E W et al. *Neurosci Lett* 249:177-179, (1998), Loddick S A et al *J Cereb Blood Flow Metab* 16:932-940, (1996), Stroemer R P et al., *J Cereb Blood Flow Metab.* 18:833-839, (1998)). Conversely, blocking IL-1 actions with a receptor antagonist or a neutralizing antibody markedly reduces neuronal death and inflammation in models of ischemic damage (see Betz A L, *J Cereb Blood Flow Metab* 15:547-551, (1995); Relton J K, *Brain Res Bull* 29:243-246, (1992); Yamasaki Y et al, Stroke 26:676-680, (1995)). Furthermore, mice with decreased IL-1.beta. production (caspase-1 knockouts) are significantly protected from ischemic injury (Schielke G P, et al. *J Cereb Blood Flow Metab* 18:180-185, (1998)) and IL-1α and β double knockouts exhibit dramatically reduced ischemic infarct volumes compared with wild-type mice (87% reduction in cortex) (Boutin H et al., *J Neurosci* 21:5528-5534, (2001)).

In addition to a role in ischemic damage, IL-1 elevation has been associated with many neurodegenerative diseases. There is increasing evidence for a role of IL-1 in Alzheimer's Disease (AD) (Mrak R E et al. Neurobiol Aging 22(6):903-908, (2001)). Elevated levels of IL-1β have been shown to surround amyloid plaques in the disease and recent genetic studies have indicated that a polymorphism in IL-1α is linked to an increased risk of AD (3-6 fold increase) (Griffin W S et al., J Leukoc Biol 72(2):233-238, (2002)). This polymorphism has also been correlated with rate of cognitive decline in AD patients (Murphy G M et al., Neurology, 56(11)1595-1597, (2001)). The risk of AD is increased even further when the polymorphism in IL-i.alpha. is found in combination with another polymorphism in IL-1β (see Griffin W S, supra), providing convincing evidence that these cytokines play an important role in the pathology of the disease.

This assay measures the release of IL-1β from a mouse microglial cell line following an inflammatory challenge with LPS and interferon-gamma. The ability of test articles to inhibit microglial cell activation and IL-1β release is determined by co-incubation of the test article with the inflammatory challenge.

Cerebral ischemic insults are modeled in animals by occluding vessels to, or within, the cranium (Molinari, G. F., 1986, in H. J. M. Barnett, et al., (Eds) Stroke: Pathophysiology, Diagnosis and Management, Vol. 1, Churchill Livingstone, N.Y.). The rat middle cerebral artery occlusion (MCAO) model is one of the most widely used techniques to induce transient focal cerebral ischemia approximating cerebral ischemic damage in humans, e.g., those who suffer from a stroke. The middle cerebral artery used as the ischemic trigger in this model is the most affected vessel in human stroke. The model also entails a period of reperfusion, which typically occurs in human stroke victims. MCAO involving a two-hour occlusion has been found to produce the maximum size of cortical infarction obtainable without increased mortality at twenty-four hours.

Further validation of efficacy in neuroprotection can be assessed in functional tests, such as the grip strength test or the rotorod test. Animals treated with compounds that show neuroprotection maintain their pre-MCAO grip strength values after MCAO, as compared to untreated animals, which showed a significant reduction in grip strength, indicating loss of sensorimotor function. Likewise, animals treated with compounds that show neuroprotection also maintained their pre-MCAO rotorod activity scores after MCAO, as compared to untreated animals, which showed a significant reduction in rotorod scores, indicating loss of sensorimotor function at higher brain levels.

In vitro cell-based assays for inflammation are well known in the art, for example e-selectin (also named Endothelial Leukocyte Adhesion Molecule or ELAM) or C-reactive protein (CRP). The ELAM assay measures in vitro activity of the test compounds in reducing expression of ELAM in activated endothelial cells. Briefly, endothelial cells are created by adding known activators such as lipopolysaccharides, TNF or IL-1β, alone or in some combination. Activated cells produce ELAM, which can be measured using, for example, an E-selectin monoclonal antibody-based ELISA assay. Similarly the CRP assay measures in vitro activity of test compounds in reducing expression of CRP in Human Hep3B epithelial cells. The activated cells produce CRP, which can be measured with a CRP ELISA assay.

In vivo evaluation of anti-inflammatory activity can be determined by well characterized assays measuring Carrageenan-Induced Paw Edema and by Mouse Ear Inflammatory Response to Topical Arachidonic Acid. (Gabor, M., Mouse Ear Inflammation Models and their Pharmacological Applications, 2000). Carrageenan-Induced Paw Edema is a model of inflammation, which causes time-dependent edema formation following carrageenan administration into the intraplantar surface of a rat paw. The application of arachidonic acid (AA) to the ears of mice produces immediate vasodilation and erythema, followed by the abrupt development of edema, which is maximal at 40 to 60 min. The onset of edema coincides with the extravasations of protein and leukocytes. After one hour the edema wanes rapidly and the inflammatory cells leave the tissue so that at 6 hours the ears have returned to near normal. These assays, as described in the Examples, measure a test compound's ability to treat these inflammatory processes via systemic and topical routes of administration.

The 5-lipoxygenase pathway is a major synthetic pathway relevant to human inflammatory disease. 5-lipoxygenase catalyses the two first steps in the oxygenation of arachidonic acid (a polyunsaturated 20-carbon fatty acid) to leukotrienes. Leukotrienes are known to be important mediators of inflammatory and allergic reactions. The first step in the synthesis of leukotrienes, which is catalyzed by 5-lipoxygenase, is the formation of 5-HPETE. The rearrangement of 5-HPETE to form the unstable $LTA_4$, the rate-limiting step in the synthesis of the leukotrienes, is also catalyzed by 5-lipoxygenase. $LTA_4$ is then converted to either $LTB_4$ or $LTC_4$. $LTC_4$ is rapidly metabolized to $LTD_4$ and then to $LTE_4$. $LTC_4$, $LTD_4$ and $LTE_4$ are collectively referred to as the cysteinyl (Cys) leukotrienes.

Biosynthesis of $LTB_4$, $C_4$, $D_4$ and $E_4$ occurs predominantly in leukocytes, in response to a variety of immunological stimuli. The primary target of $LTB_4$ is the leukocyte where it elicits enzyme release, chemotaxis, adherence, and aggregation in nM concentrations. $LTB_4$ modulates immune responses and participates in the host-defense against infections. Hence, $LTB_4$ is an important chemical mediator in the development and maintenance of inflammatory reactions and disease states.

In vitro evaluation of the ability of a composition to inhibit the enzymes 5- or 12/15 as described in Walidge, N. B. et al Anal. Biochem., 231: 354-358 (1995) using a high throughput assay format with colorimetric method for the determination of lipoxygenase activity; as well as in vitro evaluation of inhibiting $LTB_4$ is described in Examples.

Administration

The compounds of Formula I are administered at a therapeutically effective dosage, e.g., a dosage sufficient to provide treatment for the disease states previously described. Administration of the compounds of the invention or the pharmaceutically acceptable salts thereof can be via any of the accepted modes of administration for agents that serve similar utilities.

While human dosage levels have yet to be optimized for the compounds of the invention, generally, a daily dose is from about 0.01 to 10.0 mg/kg of body weight, preferably about 0.1 to 5 mg/kg of body weight, and most preferably about 0.3 to 1.0 mg/kg of body weight. The amount of active compound administered will, of course, be dependent on the subject and disease state being treated, the severity of the affliction, the manner and schedule of administration and the judgment of the prescribing physician.

In employing the compounds of this invention for treatment of the above conditions, any pharmaceutically acceptable mode of administration can be used. The compounds of this invention can be administered either alone or in combination with other pharmaceutically acceptable excipients, including solid, semi-solid, liquid or aerosol dosage forms, such as, for example, tablets, capsules, powders, liquids, suspensions, suppositories, aerosols or the like. The compounds of this invention can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages. The compositions will typically include a conventional pharmaceutical carrier or excipient and a compound of this invention or a pharmaceutically acceptable salt thereof. In addition, these compositions may include other medicinal agents, pharmaceutical agents, carriers, adjuvants, and the like, including, but not limited to anticoagulants, blood clot dissolvers, permeability enhancers and slow release formulations.

Generally, depending on the intended mode of administration, the pharmaceutically acceptable composition will contain about 0.1% to 90%, preferably about 0.5% to 50%, by weight of a compound or salt of Formula I, the remainder being suitable pharmaceutical excipients, carriers, etc.

One preferred manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium crosscarmellose, glucose, gelatin, sucrose, magnesium carbonate, and the like. Such compositions take the form of solutions, suspensions, tablets, dispersible tablets, pills, capsules, powders, sustained release formulations and the like.

Preferably the compositions will take the form of a pill or tablet and thus the composition will contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrine derivatives, sorbitan monolaurate, triethanolamine acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound in an amount effective to alleviate the symptoms of the subject being treated.

Dosage forms or compositions containing active ingredient in the range of 0.005% to 95% with the balance made up from non-toxic carrier may be prepared.

For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate, sodium saccharin, talcum and the like. Such compositions take the form of solutions, suspensions, tablets, capsules, powders, sustained release formulations and the like. Such compositions may contain 0.01%-95% active ingredient, preferably 0.1-50%.

For a solid dosage form, the solution or suspension, in for example propylene carbonate, vegetable oils or triglycerides, is preferably encapsulated in a gelatin capsule. Such diester solutions, and the preparation and encapsulation thereof, are disclosed in U.S. Pat. Nos. 4,328,245; 4,409,239; and 4,410,545. For a liquid dosage form, the solution, e.g. in a polyethylene glycol, may be diluted with a sufficient quantity of a pharmaceutically acceptable liquid carrier, e.g. water, to be easily measured for administration.

Alternatively, liquid or semi-solid oral formulations may be prepared by dissolving or dispersing the active compound or salt in vegetable oils, glycols, triglycerides, propylene glycol esters (e.g. propylene carbonate) and the like, and encapsulating these solutions or suspensions in hard or soft gelatin capsule shells.

Other useful formulations include those set forth in U.S. Pat. Nos. Re. 28,819 and 4,358,603.

The formulation can be administered in a single unit dosage form for continuous treatment or in a single unit dosage form ad libitum when relief of symptoms is specifically required. For example, the formulation may be administered as a bolus or as a continuous intravenous infusion after onset of symptoms of stroke, myocardial infarction or chronic heart failure.

Another preferred manner of administration is the topical administration. "Topical administration" refers to application of the present compositions by spreading, spraying, etc. onto the surface of the skin. The typical amount applied may vary from about 0.1 mg of composition per square centimeter of skin to about 25 mg of composition per square centimeter of skin. The compounds of the present invention may be formulated for topical administration to the epidermis as ointments, creams or lotions or as transdermal patch. Formulations suitable for topical administration in the mouth include lozenges, pastilles and mouthwashes.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

A more recently devised approach for parenteral administration employs the implantation of a slow-release or sustained-release system, such that a constant level of dosage is maintained. See, e.g., U.S. Pat. No. 3,710,795. The percentage of active compound contained in such parenteral compositions is highly dependent on the specific nature thereof, as well as the activity of the compound and the needs of the subject. However, percentages of active ingredient of 0.01 % to 10% in solution are employable, and will be higher if the composition is a solid which will be subsequently diluted to the above percentages. Preferably the composition will comprise 0.2-2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, preferably less than 10 microns.

EXAMPLES

The following preparations and examples are given to enable those skilled in the art to more clearly understand and to practice the present invention. They should not be considered as limiting the scope of the invention, but merely as being illustrative and representative thereof.

General Characterization Methods

As reported in the following examples, Nuclear Magnetic Resonance (NMR) spectra were recorded on a Bruker DTX 300 spectrometer using, in most cases, tetramethyl silane (TMS) as the internal reference. Mass spectra were obtained on an Agilent 1100 LC/MSD instrument using either electrospray ionization (positive or negative mode) (ESI) or atmospheric pressure chemical ionization (positive or negative mode) (APCI).

Example 1

Beta-Amyloid Cell Death Assay

Media Composition
Neurobasal/B27i: Neurobasal medium plus 1× B27 supplement, 0.5 mM L-glutamine, 25 µM L-glutamic acid, and 0.5× Penicillin/Streptomycin
Neurobasal/B27m: Neurobasal medium plus 1× B27 supplement and 0.5 mM L-glutamine BSS (Ca/Mg free): HBSS (calcium/magnesium free) plus 10 mM Hepes (pH 7.25), 1× Penicillin/Streptomycin, and 1 mM Sodium Pyruvate
Glucose-free $BSS_0$: 143.6 mM NaCl, 5.4 mM KCl, 1.8 mM $CaCl_2$, 0.8 mM $MgSO_4$, 1 mM $NaH_2PO_4$, 26.2 mM $NaHCO_3$, 10 mg/l phenol red, 0.25× Penicillin/Streptomycin, and 10 mM Hepes (pH 7.4)
Papain Quench solution: Neurobasal medium plus 1× B27 supplement, 1× Penicillin/Streptomycin and 0.5 mg/ml DNase1
Assay media: Neurobasal medium plus 1× B27 (minus AO) supplement, 0.5 mM L-glutamine, and 0.25× Penicillin/Streptomycin.

Experimental Procedure

Hippocampal Cell Culture

Hippocampal neurons were isolated from E18 rat embryos as follows. Embryos were decapitated and the heads immersed in cold BSS (Ca/Mg free). Using a dissecting microscope the hippocampi were dissected out and placed in cold BSS (Ca/Mg free). The isolated hippocampi were then centrifuged at 1000 rpm for 2 min, the BSS aspirated off and 2 ml of 2 mg/ml Papain in Neurobasal media added per 10 embryos. After mixing on a rotational shaker for 10 min at 37° C., 5 ml Papain Quench solution was added. Cells were then centrifuged at 1000 rpm for 2 min, the supernatant was aspirated and 2ml of Neurobasal/B27i was added. The cells were triturated 6 times with siliconized pipettes (decreasing bore size) after which an additional 5 ml Neurobasal/B27i was added. The cell suspension was then centrifuged at 1000 rpm for 2 min, the supernatant was aspirated and 2 ml of Neurobasal/B27i was added. Cells were triturated again as described above and the volume of Neurobasal/B27i was adjusted to 1 ml/embryo. Cells were then counted and seeded at a density of 75,000 cells per well in a poly-D-lysine coated 24-well plate. After four days media was removed from the cells and replaced with Neurobasal/B27m media +5 µM Ara-C (cytosine arabinoside). Seven days after isolation the media was removed again and replaced with fresh Neurobasal/B27m media. Ten days after isolation the hippocampal cultures were used in the assay described below.

Preparation of Oligomeric beta-Amyloid (Aβ) Peptide

Aggregation of Aβ(1-42) (American Peptide Co, Sunnyvale, Calif.) into oligomers was carried out according to the method of Dahlgren et al, (2002) Oligomeric and fibrillar species of amyloid-beta peptides differentially affect neuronal viability. J Biol Chem 277: 32046-32053. The Aβ peptide was dissolved to 1 mM in hexafluoroisopropanol (HFIP) and aliquoted into sterile microcentrifuge tubes. The HFIP was removed under vacuum and the peptide film stored at −20° C. The day before the assay, the peptide film was resuspended in dry DMSO to a concentration of 5 mM. Ham's F-12 media was then added to bring the peptide to a final concentration of 100 µM, and this solution was incubated at 4° C. for 24 hours to allow formation of oligomers.

Treatment of Hippocampal Neurons with Oligomeric Aβ

The existing growth medium was aspirated from the hippocampal cultures and the monolayer was washed once with 500 µl glucose free-$BSS_0$. Test articles were diluted to 2-fold the desired testing concentration in assay media and 250 µL was added to the cells. From the 100 µM oligomeric beta-amyloid peptide solution described above, a working solution of 6 µM was made in assay media. 250 µL of this working solution was also added to the cells. The final volume for each well was 500 µL and the final concentration of Aβ peptide was 3 µM. As a negative control, cells were incubated with 500 µL assay media with no additions.

Cells were incubated in a 39° C. incubator (5% CO$_2$) for 24 hours. After this time, the number of live neurons remaining in each well was determined using a fluorescent vital cell stain, Cell Tracker Green (Molecular Probes, Eugene, Oreg.). Assay media was aspirated from the cells and 400 µL of 2.5 µM Cell Tracker Green was added to each well. Cells were placed in a 37° C. incubator for 5 minutes after which time the cell stain was aspirated off and 500 µl of HBSS (Invitrogen, Life Technologies, Carlsbad, Calif.) was added to each well. The number of live cells in each well was then quantitated using an automated fluorescent microscope/imaging system (Universal Imaging, Downingtown Pa.).

Certain compounds of the present invention such as
3-(6-Hydroxy-2-methyl-3,4,7,8,9,10-hexahydro-7,10-methano-2H-benzo[h]chromen-2-yl)-propionic acid methyl ester;
3-(6-Hydroxy-2-methyl-3,4,7,8,9,10-hexahydro-7,10-methano-2H-benzo[h]chromen-2-yl)-propionic acid;
3-(6-Hydroxy-2-methyl-3,4,7,8,9,10-hexahydro-7,10-propano-2H-benzo[h]chromen-2-yl)-propionic acid;
2-(3-Chloro-propyl)-2-methyl-3,4,7,8,9,10-hexahydro-7,10-methano-2H-benzo[h]chromen-6-ol; and
2-[3-(Benzothiazol-2-ylsulfanyl)-propyl]-2-methyl-3,4,7,8,9,10-hexahydro-7,10-methano-2H-benzo[h]chromen-6-ol;

when tested as described above exhibited assay between 10% and 40% protection in the p amyloid cell assay Example 2

MPP$^+$ Cell Death Assay

Media Composition
RF media: DMEM-No glucose, glucose (29.1 mM), L-glutamine (1.4 mM), 10% heat-inactivated FBS, and 1× penicillin/streptomycin (P/S)
Wash media: DMEM-No glucose and 1× P/S
Low serum media: DMEM-No glucose, glucose (29.1 mM), L-glutamine (1.4 mM), 0.5% FBS, and 1× P/S
Assay Media: DMEM-No glucose, L-glutamine (1.4 mM), 0.5% FBS, and 1× P/S Experimental Procedure The substantia nigra-derived dopaminergic progenitor cell line was seeded in poly-D-lysine-coated 24-well plates at a density of 4500 cells per well in RF media. The cells were left to attach for 16 hours in a 33° C. incubator (5% CO$_2$) after which time they were washed once with 500 µL wash media and then differentiated into a neuronal phenotype by incubating in low serum media for 24 hours in a 39° C. incubator (5% CO$_2$).

After 24 hours the low serum medium was aspirated from the cells and the monolayer was washed once with 500 µL wash media. Test articles were diluted to 2-fold the desired testing concentration in assay media and 250 µL was added to the cells. From a 10 mM stock, a working solution of 140 µM 1-methyl-4-phenylpyridinium (MPP$^+$) (Sigma, St. Louis, Mo.) was made in assay media and 250 µL of this working solution was also added to the cells. The final volume in each well was 500 µL and the final concentration of MPP$^+$ was 70 µM. As a negative control, cells were incubated with 500 µL assay media with no additions.

Cells were incubated in a 39° C. incubator (5% CO$_2$) for 24 hours. After this time, the number of live neurons remaining in each well was determined using a fluorescent vital cell stain, Cell Tracker Green (Molecular Probes, Eugene, Oreg.). Assay media was aspirated from the cells and 400 µL of 2.5 µM Cell Tracker Green was added to each well. Cells were placed in a 37° C. incubator for 5 minutes after which time the cell stain was aspirated off and 500 µL of HBSS (Invitrogen Life Technologies, Carlsbad, Calif.) was added to each well. The number of live cells in each well was then quantitated using an automated fluorescent microscope/imaging system (Universal Imaging, Downingtown Pa.).

Results:
Certain compounds of the present invention such as
3-(6-Hydroxy-2-methyl-3,4,7,8,9,10-hexahydro-7,10-methano-2H-benzo[h]chromen-2-yl)-propionic methyl ester;
3-(6-Hydroxy-2-methyl-3,4,7,8,9,10-hexahydro-7,10-methano-2H-benzo[h]chromen-2-yl)-propionic
2,2,-Dimethyl-3,4,7,8,9,10-hexahydro-7,10-methano-2H-benzo[h]chromen-6-ol;
2-Methyl-2-[3-(thiazol-2-ylsulfanyl)-propyl]-3,4,7,8,9,10-hexahydro-7,10-methano-2H-benzo[h]chromen-6-ol;
[3-(6-Hydroxy-2-methyl-3,4,7,8,9,10-hexahydro-7,10-methano-2H-benzo[h]chromen-2-yl)-propyl]-phosphonic acid dimethyl ester;
3-[6-Hydroxy-2-methyl-5-(3-methyl-but-2-enyl)-3,4,7,8,9,10-hexahydro7,10-methano-2H-benzo[h]chromen-2-yl]-propionic acid;
2-(3-Hydroxy-propyl)-2-methyl-3,4,7,8,9,10-hexahydro-7,10-propano-2H-benzo[h]chromen-6-ol;
3-(6-Hydroxy-2-methyl-3,4,7,8,9,10-hexahydro-7,10-propano-2H-benzo[h]chromen-2-yl)-propionic acid;
3-(6-Hydroxy-2-methyl-3,4,7,8,9,10-hexahydro-7,10-methano-2H-benzo[h]chromen-2-yl)-1-morpholin-4-yl-propan-1-one;
2-(3-Chloro-propyl)-2-methyl-3,4,7,8,9,10-hexahydro-7,10-methano-2H-benzo[h]chromen-6-ol;
2-[3-(Benzothiazol-2-ylsulfanyl)-propyl]-2-methyl-3,4,7,8,9,10-hexahydro-7,10-methano-2H-benzo[h]chromen-6-ol;
2,2-Dimethyl-3,4,7,8,9,10-hexahydro-7,10-methano-2H-benzo[h]chromen-6-ol;
2-(2-Chloro-ethyl)-2-methyl-3,4,7,8,9,10-hexahydro-7,10-methano-2H-benzo[h]chromen-6-ol;
2,2-Dimethyl-5-(3-methyl-but-2-enyl)-3,4,7,8,9,10-hexahydro-7,10-methano-2H-benzo[h]chromen-6-ol;
Acetic acid 2,2-dimethyl-5-(3-methyl-but-2-enyl)-3,4,7,8,9,10-hexahydro-7,10-methano-2H-benzo[h]chromen-6-yl ester;
2,6:9,12-Dimethano-9,10,11,12-tetrahydro-2,4,4-trimethyl-naphtho[1,2-b]oxocan-8-ol;
5-(4,6-Dimethyl-pyrimidin-2-ylsulfanylmethyl)-2,2,7,8-tetramethyl-chroman-6-ol;
2,2-Dimethyl-5-(3-methyl-butyl)-3,4,7,8,9,10-hexahydro7,10-methano-2H-benzo[h]chromen-6-ol;
5-Bromo-2,2-dimethyl-3,4,7,8,9,10-hexahydro7,10-methano-2H-benzo[h]chromen-6-ol;
Acetic acid 2,2-dimethyl-5-(3-methyl-butyl)-3,4,7,8,9,10-hexahydro-7,10-methano-2H-benzo[h]chromen-6-yl ester;
2,2-Dimethyl-5-(3-methyl-but-2-enyl)-7,8,9,10-tetrahydro-7,10-methano-2H-benzo[h]chromen-6-ol
2,2-Dimethyl-5-(3-methyl-but-2-enyl)-3,4,7,10-tetrahydro-7,10-ethano-2H-benzo[h]chromen-6-ol when tested as described above provided protection in at least 30%, preferably in at least 50% of the cells tested at concentrations ranging from 1 to 25 µM.

Example 3

MPTP Animal Model

Male C57/BL6 mice (Harlan, Ind.), weight 25-30 g, were used in all studies. MPTP-HCl (Sigma) was administered i.p. according to one of the following protocols. The maximum volume which was given per injection is 200 μL. In all studies, animals were euthanized with carbon dioxide and, brains removed for subsequent determination of dopamine depletion where appropriate.

Subacute Model

Animals received 25 mg/kg of MPTP once a day for 5 consecutive days. The end point was 2 days after the final dose.

Acute Model

Animals received 4×20 mg/kg of MPTP at 2 hour intervals. The end point was at either 7 or 14 days.

Subchronic Model

Animals received 2×40 mg/kg of MPTP with this repeated 16 hours later. The end point was at either 14 or 28 days.

Chronic Model

Animals received 25 mg/kg of MPTP, given twice weekly for 5 weeks. The end point was either 1, 3 or 24 weeks after the final dose.

Neurobehavioral Outcome Measures

Compound efficacy was examined with the use of neurobehavioral models. These models allowed the determination of a given compound's ability to reverse the motor deficits seen with MPTP treatment.

All animals received pre-training for the individual model and a baseline reading was obtained one day prior to the commencement of MPTP treatment.

Open Field Test

The open field test measures spontaneous activity. Deficits can be observed with hippocampal and basal ganglia lesions, and with hind limb dysfunction. It is sensitive to moderate dopamine (DA) depletion.

The open field test was carried out in a clear, acrylic open box 60 cm×60 cm. The base of the box was marked into a 5×5 grid of 12 cm×12 cm squares. Animals were individually placed in the box and allowed to roam free. The number of squares an animal crossed in a 90 second time period was recorded. In order to be scored, the animal must either have had all four limbs within a given square or, all four limbs must have left a given square.

Tactile Adhesion Model

The tactile adhesion model measures an animal's ability to complete a complex sensorimotor task. It is sensitive to moderate to severe DA depletion.

A tactile stimulus (0.5×0.5 cm square of "sticky tape") was applied to each side of the animal's face and the time taken to remove it was recorded. The following measurements were recorded:
   a. Latency to contact left side tape
   b. Latency to contact right side tape
   c. Order of side contacted (left vs. right)
   d. Latency to remove left side tape
   e. Latency to remove right side tape Pole test The pole test evaluates motor co-ordination.

A rough surfaced metal pole (diameter 8 mm, height 50 cm) protruding from a cage filled with animal bedding was used for this test. Animals were placed head upwards at the top of the pole. They were required to turn and descend downwards and the time taken for this was recorded (latency to reach bedding). Timing was started when the individual animal gripped the top of the pole and was stopped when all four limbs contacted the bedding.

Compound Administration

All test compounds were administered ip. The maximum volume which was given per injection was 200 μL. Compounds were dosed up to twice daily, two days prior and 7 days post MPTP treatment.

Data Analysis

A baseline reading was taken for each animal one day prior to MPTP treatment. All subsequent readings were normalized to the individual animal's baseline. Values were expressed as a percent baseline.

Data is percent baseline and expressed as mean±std dev:

|  | Day 1 | Day 2 | Day 3 |
|---|---|---|---|
| MPTP positive control | 1329 ± 973 | 2740 ± 1298 | 1641.7 ± 651.1 |
| Neg control (no MPTP) | 90.8 ± 27.4 | 98.9 ± 42.5 | 137.2 ± 100.9 |
| L-DOPA | 110 ± 13.2 | 97.9 ± 20.0 | 100.1 ± 14.8 |
| Vehicle | 1238.3 ± 987.8 | 1008.5 ± 992.1 | 308.9 ± 239.6 |
| 3 mg/kg/day | 623.7 ± 533.1 | 355.3 ± 207.3* | 90.7 ± 15.2* |
| 10 mg/kg/day | 520.2 ± 52.1 | 363.7 ± 94.9* | 137.9 ± 44.9* |
| 30 mg/kg/day | 105.3 ± 22.1*† | 94.2 ± 27.7*† | 108.2 ± 29.1* |

*$p < 0.05$ (relative to MPTP induced deficit)
†$p < 0.05$ (relative to vehicle)

Summary

Compound and vehicle given for 9 days in total, 2 days prior to MPTP and 7 days after MPTP treatment. L-DOPA given 1 hour prior to the pole test each day.

Results

Certain compounds of Formula I, such as 3-(6-Hydroxy-2-methyl-3,4,7,8,9,10-hexahydro-7,10-methano-2H-benzo[h]chromen-2-yl)-propionic acid methyl ester 3-(6-Hydroxy-2-methyl-3,4,7,8,9,10-hexahydro-7,10-methano-2H-benzo[h]chromen-2-yl)-propionic acid at a dose of 30 mg/kg/day significantly reduced the functional deficit produced by MPTP on each of days 1-3. Functional outcome was significantly better on days 1 and 2 than in vehicle treated animals and in both cases was comparable to that of the negative control group.

Doses of 10 mg/kg/day and 3 mg/kg/day significantly reduced the MPTP induced deficit on days 2 and 3 but this was not significantly different from vehicle treated animals.

Example 4

FRDA Fibroblast Assay for Protection from Oxidative Stress

A. Cell Culture and Reagents

Primary fibroblasts were derived from donors with a molecular diagnosis of FRDA and control donors with no mitochondrial disease. Lines F2, C2 and C3 were obtained from Coriell Cell Repositories (Camden, N.J., USA; catalog #'s GM04078, GM 08402 and GM08399, respectively). All cell types were diagnosed at the molecular level for intronic GAA triplet repeat length in the frataxin gene using a PCR-based method, according to methods known in the art. FRDA-fibroblasts types had ~400-450 repeats (F2 line) or more (F1 and F3), whereas control cell lines displayed repeats of normal length. The cells were seeded in 96-well plates at a density of 4000 cells per 100 µl in growth medium consisting of 25% (v/v) M199 EBS and 64% (v/v) MEM EBS without phenol red (Bioconcept, Allschwil, Switzerland) supplemented with 10% (v/v) fetal calf serum (PAA Laboratories, Linz, Austria), 100 U/ml penicillin, 100 µg/ml streptomycin (PAA Laboratories, Linz, Austria), 10 µg/ml insulin (Sigma, Buchs, Switzerland), 10 ng/ml EGF (Sigma, Buchs, Switzerland), 10 ng/ml bFGF (PreproTech, Rocky Hill, N.J., USA) and 2 mM glutamine (Sigma, Buchs, Switzerland). The cells were incubated in the presence of the various test compounds for 24 h before addition of 1 mM BSO (L-buthionine (S,R)-sulfoximine).

B. Cell Viability Measurements

Cell viability was measured after the first signs of toxicity appeared in the BSO-treated controls (typically after 16-48 h). The cells were stained for 60 min at room temperature in PBS with 1.2 µm calceinAM and 4 µm ethidium homodimer (Live/Dead assay, Molecular Probes, Eugene, Oreg., USA). Fluorescence intensity was measured with a Gemini Spectramax XS spectrofluorimeter (Molecular Devices, Sunnyvale, Calif., USA) using excitation and emission wavelengths of 485 and 525 nm, respectively.

C. Data and statistics

In experiments carried out in support of the present invention, certain compounds such as 3-(6-Hydroxy-2-methyl-3,4,7,8,9,10-hexahydro-7,10-methano-2H-benzo[h]chromen-2-yl)-propionic acid methyl ester;

3-(6-Hydroxy-2-methyl-3,4,7,8,9,10-hexahydro-7,10-methano-2H-benzo[h]chromen-2-yl)-propionic acid;

3-[6-Hydroxy-2-methyl-5-(3-methyl-but-2-enyl)-3,4,7,8,9,10-hexahydro-7,10-methano-2H-benzo[h]chromen-2-yl]-propionic acid;

2-(3-Hydroxy-propyl)-2-methyl-3,4,7,8,9,10-hexahydro-7,10-propano-2H-benzo[h]chromen-6-ol;

2-(3-Chloro-propyl)-2-methyl-3,4,7,8,9,10-hexahydro-7,10-methano-2H-benzo[h]chromen-6-ol;

2,6:9,12-Dimethano-9,10,11,12-tetrahydro-2-methylnaphtho[1,2-b]oxocan-8-ol;

2,2-Dimethyl-3,4,7,8,9,10-hexahydro-7,10-methano-2H-benzo[h]chromen-6-ol;

2-(2-Chloro-ethyl)-2-methyl-3,4,7,8,9,10-hexahydro-7,10-methano-2H-benzo[h]chromen-6-ol;

2,2-Dimethyl-5-(3-methyl-but-2-enyl)-3,4,7,8,9,10-hexahydro-7,10-methano -2H-benzo[h]chromen-6-ol;

5-Bromo-2,2-dimethyl-3,4,7,8,9,10-hexahydro7,10-methano-2H-benzo[h]chromen-6-ol;

Acetic acid 2,2-dimethyl-5-(3-methyl-butyl)-3,4,7,8,9,10-hexahydro-7,10-methano-2H-benzo[h]chromen-6-yl ester;

2-(3-Isobutylsulfanyl-propyl)-2-methyl-3,4,7,8,9,10-hexahydro-7,10-methano-2H-benzo[h]chromen-6-ol;

2-Methyl-2-thiophen-2-yl-3,4,7,8,9,10-hexahydro-7,10-methano-2H-benzo[h]chromen-6-ol;

2,2-Dimethyl-3,4,7,10-tetrahydro-7,10-methano-2H-benzo[h]chromen-6-ol;

2,2-Dimethyl-3,4,7,8,9,10-hexahydro-7,10-ethano-2H-benzo[h]chromen-6-ol;

2,2-Dimethyl-5-(3-methyl-but-2-enyl)-7,8,9,10-tetrahydro-7,10-methano-2H-benzo[h]chromen-6-ol;

2,2-Dimethyl-5-(3-methyl-but-2-enyl)-3,4,7,10-tetrahydro-7,10-ethano-2H-benzo[h]chromen-6-ol significantly reduced cell death in FRDA fibroblasts compared to untreated FRDA fibroblasts with an $EC_{50}$ of between 0.01 µM and 10 µM.

Example 5

Determination of Activity Utilizing Neuronal Cell Stress Assay

A. Isolation and Culture of Primary Hippocampal Neuronal Cells.

Materials
  Neurobasal/B27: Neurobasal medium (Invitrogen, Carlsbad, Calif.) with 1× B27 supplement (Invitrogen Life Technologies), 0.5 µM L-glutamine, 25 µM L-glutamic acid, and 1× Penicillin/Streptomycin.
  Hank's Basic Salt Solution (HBSS, Ca/Mg-free) was prepared by preparing 1× Hanks CMF (Gibco) supplemented with HEPES (10 mM, pH 7.3), sodium bicarbonate (0.35%), 1× Penicillin/Streptomycin, and 1 mM pyruvate.
  Poly-D-lysine (Sigma, St. Louis, Mo.), 50 µg/ml solution filtered through 0.2 µm filter tubes.
  Sigmacote (Sigma, St. Louis, Mo.).
  Plastic Culture Flasks (T75 $cm^2$) or 12-well cell culture plates treated with Poly-D-Lysine (Sigma, St. Louis, Mo.).

Preparation of Primary Hippocampal Neuronal Cells

A pregnant female mouse (E18-E19) was euthanized with $CO_2$ prior to removal of the uterus, which was then placed in a sterile plastic petri dish. The embryos were removed from the sac, and the embryonic brains were removed and immersed in cold (4° C.) Buffered Salt Solution (HBSS; Ca/Mg free; Invitrogen Life Technologies) in a small petri dish. Hippocampi were then removed from the brains under a dissecting microscope and were placed on a paraffin-covered dish. The meninges were stripped away and the dissected hippocampi were collected in a small petri dish in HBSS. The hippocampi were transferred to a 15-ml centrifuge tube (normally 10-12 brains)filled with HBSS. The tube containing the brains was centrifuged at 1000 rpm for 2 min in a tabletop centrifuge. The supernatant was removed, 2 ml of HBSS was added to the hippocampi in the tube, and the resulting suspension was triturated 2 times each with long-tipped siliconized glass pipettes having progressively smaller apertures, starting with a pipette with a standard size opening (approximately 1.0 mm diameter), following with one having an aperture of half standard size (approximately 0.5 mm diameter), then with one having an aperture about one-half that size (0.25 mm diameter). The suspension was then centrifuged again at 1000 rpm for 2 min in a tabletop centrifuge, the supernatant was discarded, and 2 ml of Neurobasal/B27i (with antibiotics) was added to the tube. The trituration procedure described above was then repeated on this suspension.

The density of cells was determined on a small aliquot of cells using standard counting procedures and correcting for cell viability by trypan blue stain exclusion. Using this procedure, the expected yield is $3 \times 10^5$-$6 \times 10^5$ cells/brain. Cells were then added to PDL-coated 24-well plates, flasks or MetTek dishes in Neurobasal/B27 l at a density of about $1.5 \times 10^6$ cells (T75 flask) or about 70,000 cells/well of a 24-well plate. Plated cells were incubated at 37 degrees in an atmosphere of 5 % $CO_2$/95% $O_2$. Media was renewed after 3-4 days by replacing half of it with fresh Neurobasal/B27m medium, containing 5 µM cytosine arabinoside (AraC).

Seven to eight days from the initial culture, the media was renewed again, by removing one-half or it and replacing with an equal amount of fresh Neurobasal/B27m medium (without Ara-C).

B. Hippocampal Anoxia-Reoxygenation Cell Death Assay

This assay was used to induce ischemia by anoxia-reoxygenation in cultured hippocampal neuronal cells. Test compounds were added to assess potency and efficacy against ischemia-induced neuronal cell injury and cell death.

Materials.
Neurobasal media, NoG neurobasal media, B27 supplement and B27 Supplement minus AO were obtained from Invitrogen Life Technologies.
Neurobasal/B27 medium was prepared with 2× B27 minus AO supplement, 0.5 mM L-glutamine and 0.25× penicillin/streptomycin.
Cell Tracker Green was obtained from Molecular Probes and a fresh 5 μM solution was prepared from 10 mM stock just before use.
LoG-Neurobasal contains NoG neurobasal medium plus 1 mM glucose, 0.5 mM L-glutamine, 0.25× Penicillin/Streptomycin, and 10 mM Hepes (pH 7.4).
Primary hippocampal neuronal cells were prepared according to the methods described above and were cultured in poly-D-lysine coated 24-well plates for 10-11 days prior to use.

Deoxygenated LoG-Neurobasal medium (100 ml) was prepared by pre-equilibrating the medium in a T150 cm$^2$ flask in a hypoxic chamber overnight. Following pre-incubation under hypoxic conditions, the LoG-Neurobasal media was lightly bubbled with 100% $N_2$ for 30 min to completely deoxygenate the media. An additional 20 ml LoG-Neurobasal was pre-equilibrated in a T75 cm$^2$ flask and was incubated in a normal incubator (5% $CO_2$) overnight. Reoxygenated medium was prepared by placing Neurobasa/B27 media overnight in the culture incubator (5% $CO_2$/95% $O_2$).

10-11 Days after plating the hippocampal neurons, existing culture medium (Neurobasal/B27m) was removed from the cells by aspiration. Cells were washed once with 600 μl/well (24-well culture plates) of glucose free-BSS. Neurons were replenished with deoxygenated LoG-Neurobasal (400 μl per well for each well of a 24-well plate). Test compounds were added directly to each well (usually 3 concentrations of the compound plus positive control, each in triplicate). Most test compounds were dissolved in 100% DMSO; however, concentrations were adjusted such that the final concentration of DMSO in the cell media never exceeded 0.5%. Plates containing cells with test compounds were placed in a hypoxic chamber for 4-5 hr with plate lids ajar. For normoxia controls, pre-equilibrated normoxic LoG-Neurobasal medium was added to each well of cells, and the plate was replaced in the normal culture incubator for 4-5 hr. After 4-5 hr of hypoxia, the existing media was carefully aspirated off, and 400 μL of new, reoxygenated (pre-equilibrated) Neurobasal/B27 was added to each well. The same test compounds (in the same the concentrations) were added back into the corresponding wells. Plates were placed in the cell culture incubator (5% $CO_2$/95% $O_2$) and reoxygenated for 20-24 hr. After reoxygenation for 20-24 hr, live neurons were quantitated using the cell tracker green fluorescence method, described below.

To test for cell viability, existing culture medium was aspirated from each well of the 24 well plates, and neurons were washed once with 1 mL of HBSS (pH 7.4, pre-warmed to 30-37° C.). To each well was added 500 μL of 5 μM Cell Tracker Green fluorescent dye dissolved in HBSS. Plates were placed in the dark at room temperature for 15 minutes, then were washed with 1 mL of HBSS. 500 μL of HBSS was then added to each well, and fluorescent cells were counted using a fluorescent microscope. Significantly increased cell viability compared to control cells is indicative of a protective compound.

Certain compounds of the present invention such as:
3-(6-Hydroxy-2-methyl-3,4,7,8,9,10-hexahydro-7,10-methano-2H-benzo[h]chromen-2-yl)-propionic acid methyl ester;
3-(6-Hydroxy-2-methyl-3,4,7,8,9,10-hexahydro-7,10-methano-2H-benzo[h]chromen-2-yl)-propionic acid;
2,2,-Dimethyl-3,4,7,8,9,10-hexahydro-7,10-methano-2H-benzo[h]chromen-6-ol;
3-(6-Hydroxy-2-methyl-3,4,7,8,9,10-hexahydro-7,10-propano-2H-benzo[h]chromen-2-yl)-propionic acid methyl ester;
[3-(6-Hydroxy-2-methyl-3,4,7,8,9,10-hexahydro-7,10-methano-2H-benzo[h]chromen-2-yl)-propyl]-phosphonic acid dimethyl ester;
[3-(6-Hydroxy-2-methyl-3,4,7,8,9,10-hexahydro-7,10-methano-2H-benzo[h]chromen-2-yl)-propyl]-phosphonic acid;
3-(6-Hydroxy-2-methyl-3,4,7,8,9,10-hexahydro-7,10-methano-2H-benzo[h]chromen-2-yl)-propionic acid methyl ester;
4-(6-Hydroxy-2-methyl-3,4,7,8,9,10-hexahydro-7,10-methano-2H-benzo[h]chromen-2-yl)-butane-1-sulfonic acid dimethylamide;
3-(6-Hydroxy-2-methyl-3,4,7,8,9,10-hexahydro-7,10-methano-2H-benzo[h]chromen-2-yl)-propionic acid methyl ester;
3-(6-Hydroxy-2-methyl-3,4,7,8,9,10-hexahydro-7,10-methano-2H-benzo[h]chromen-2-yl)-propionic acid;
3-[7-(2-Methoxycarbonyl-ethyl)-2,7-dimethyl-2,7,9,10,11,12-hexahydro-1,8-dioxa-0-12-methano-triphenylen-2-yl]-propionic acid methyl ester
3-[6-Hydroxy-2-methyl-5-(3-methyl-but-2-enyl)-3,4,7,8,9,10-hexahydro-7,10-methano-2H-benzo[h]chromen-2-yl]-propionic acid;
2-(3-Hydroxy-propyl)-2-methyl-3,4,7,8,9,10-hexahydro-7,10-propano-2H-benzo[h]chromen-6-ol; and
2-(3-Chloro-propyl)-2-methyl-3,4,7,8,9,10-hexahydro-7,10-methano-2H-benzo[h]chromen-6-ol;

when tested as described above provided protection against stressor-induced cell death in at least about 30% of the cells tested, at concentrations ranging from 1 to 100 μM, preferably at concentrations of 25 μM.

Example 6

Rat Middle Cerebral Artery Occlusion (MCAO) Model of Cerebral Ischemia

A. Animal Preparation

Male Wistar rats (Harlan, Ind.) weighing 300-350 g were commonly used in these experiments. Animals were allowed free access to water and commercial rodent diet under standard laboratory conditions. Room temperature was maintained at 20-23° C. and room illumination is on a 12/12-hour light/dark cycle. Animals were acclimatized to the laboratory environment 5 to 7 days prior to the study, and fasted (with free access to water) overnight before surgery.

B. Middle Cerebral Artery Occlusion (MCAO)

Anesthesia was maintained by inhalation of 3.0% isoflurane (Aerrane, Front Dodge, Iowa) in 0.8% oxygen. The animal's neck was shaved and sterilized before operation. Body temperatures were controlled and maintained at 37.5° C. ±1 degree via external heating and cooling devices. To lower the body temperature, animals were placed in a cooling chamber, which uses ice to cool circulating air. Throughout the study the body temperature was recorded using a temperature transponder (BMDS Inc., Seaford, Del.) implanted subcutaneously at the time of MCAO between the rat shoulder blades that allowed the user to read the body temperature via a pocket scanner (BMDS Inc., Seaford, Del.). The body temperature was taken by inserting the temperature probe into the animal's rectum. Body temperature was recorded every hour for 6 hours post-occlusion; however, body temperatures were taken more frequently so that they could be maintained at the normothermic temperature.

Animals were subjected to two hours MCAO using a modified intraluminal filament technique, as follows: A midline incision on the ventral part of the neck was made to expose external and internal carotid arteries. The right external and common carotid arteries were ligated by a suture (silk 5/0, Carlisle Laboratories, Farmers Branch, Tex.) and the right internal artery was temporarily ligated using a microvascular clip (Fine Science Tool Inc., Foster City, Calif.). A small incision was made in the common carotid artery. A nylon filament, its tip rounded by heating, was prepared from a fishing line (Stren Fishing Lines, Wilmington, Del.) and was inserted from the right common carotid artery. The filament was advanced into the internal carotid artery 18-20 mm from the point of bifurcation of internal and external arteries and a suture is tightly ligated around the filament. Two hours post occlusion, animals were re-anesthetized to allow reperfusion for the remaining of the experiment by removal of the filament.

C. Drug Administration

Test compounds may be administered by any of a number of routes, such as those described below. Compounds can be administered before, during or after occlusion, as appropriate to the protocol.

a) Intracerebroventricular (ICV) Infusion

The anesthetized animal is placed on a stereotaxic apparatus (Harvard Apparatus, S. Natick, Mass.). Anesthesia is maintained by inhalation of 3.0% isoflurane (Aerrane, Front Dodge, Iowa) in 0.8% oxygen throughout the entire procedure. The scalp is shaved and sterilized prior to surgery. A midline sagittal incision about 3 cm long is made slightly behind the eyes to expose the skull. The skull is scraped with a rounded end spatula to remove periosteal connective tissue. A bur hole is placed 1.5 mm lateral, 1 mm posterior to the left of the bregma to mark the left lateral ventricle. A brain infusion cannula (ALZET Co., Palo Alto, Calif.) is inserted 4 mm deep into the hole. The desired depth is adjusted by attaching spacers to the cannula. The cannula attached to a 4-cm silastic catheter (Helix Medical Inc., Carpinteria, Calif.) fixed in place with dental cement (Ketac-cement, Norristown, Pa.). The catheter is either attached to a primed osmotic pump placed subcutaneously between the shoulder blades for permanent infusion or to a syringe for a short infusion.

b) Intravenous (IV) Osmotic Pump Implantation into the Jugular Vein

Anesthesia is maintained by inhalation of 3.0% isoflurane (Aerrane, Front Dodge, Iowa) in 0.8% oxygen throughout the entire procedure. The animal's neck will be shaved and sterilized before operation. A midline incision is made on the ventral part of the neck to exposes the jugular vein. The vein is isolated and ligated with a suture (silk 5/0, Carlisle Laboratories, Farmers Branch, Tex.) rostral to the point of the incision and a microvascular clip (Fine Science Tool Inc., Foster City, Calif.) close to the heart. A small incision is made between two ligations. A 2-cm silastic catheter (Helix Medical Inc.) attached to a PE-60 tube (Becton. Dickinson and Co. Sparks, Md.) connected to an ALZET (ALZET CO. Palo Alto, Calif.) pump is introduced and advanced 2 mm into the jugular vein toward the heart. The microvascular clip is removed and the catheter is secured in place with a suture (silk 5/0, Carlisle Laboratories, Farmers Branch, Tex.). The pump is placed into a pocket made subcutaneously between the shoulder blades, allowing the catheter to reach over neck to the jugular vein with sufficient slack to permit free movement of neck and head.

c) IV Infusion via Femoral Vein

Anesthesia is maintained by inhalation of 3.0% isoflurane (Aerrane, Front Dodge, Iowa) in 0.8% oxygen throughout the entire procedure. The exterior site of the right femoral vein is shaved and sterilized prior to surgery. A 3-cm incision is made in the right groin region and the femoral vein is isolated. A small incision is made on the femoral vein temporarily ligated with a microvascular clip to introduce and advance a polyethylene (PE-50) catheter (Becton Dickinson and Co. Sparks, Md.). The catheter is secured in place with suture (silk 5/0, Carlisle Laboratories, Farmers Branch, Tex.). The other end of the catheter is attached to a syringe filled with the heparinized saline for the bolus injection. Using a hemostat, a pocket is made subcutaneously on the back of the animal so the PE catheter can be brought up to the exteriorization point at the nape of the neck for either a bolus injection or a continuous injection by an osmotic pump.

d) Intraperitoneal (IP) Injection

An awake rat is held in a standard hand hold position, a 23¾ G needle is injected into the lower right quarter of the abdomen pass the peritoneum, slightly off the midline. To avoid organ injection, the plunger of the syringe is slightly pulled back. If no fluid is withdrawn, the content of the syringe is delivered into the abdominal cavity.

e) Gavage Feeding

A standard rat gavage tube (Popper & Sons Inc., NY) is attached to a 3-cc hypodermic syringe. The animal is held by the shoulder in a vertical position. The feeding tube is placed into the mouth then advanced until it reaches the stomach (the approximate insertion length of the tube was measured prior to the feeding). The content of the syringe is slowly delivered, and then the tube is withdrawn.

D. Behavioral Assessment

One hour after MCAO, the animal was gently held by its tail and observed for forelimb flexion. Then the animal is placed on the floor to be observed for walking pattern; only the animals that score 3 on Bederson grading system (Table 1) are included in the study.

TABLE 1

Bederson Grading System for Neurological Evaluation

| Neurological deficit | Grading | Behavioral observation |
|---|---|---|
| Normal | grade 0: | No observable deficit |
| Moderate | grade 1: | forelimb flexion |
| Severe | grade 2: | forelimb flexion, decreased resistance to lateral push |
| Extreme | grade 3: | forelimb flexion, decreased resistance to lateral push, circle to paretic side |

E. Evaluation of Ischemic Damage

Twenty-four hours post-MCAO, or longer, in some experiments, animals were sacrificed by $CO_2$ asphyxiation (dry ice). The brain was quickly removed from the skull, using standard procedures, rinsed in chilled saline solution, and placed on a rat brain tissue slicer (ASI instrument, MI). Seven 2-mm thick coronal slices are cut from each brain using razor blades. The slices were immersed in 0.9% saline containing 1.0% 2,3,5-triphenyltetrazolume chloride (TTC) (Sigma Chemical Co., St. Louis, Mo.) and incubated in a 37° C. water bath for 30 minutes.

After staining, each 2-mm slice was photographed with a TMC-7 camera (JH Technologies, Ca) which were directly connected to a desktop PC to capture and saved the image of each brain slice. This image was used for the measurements of the regions of interest using a computer-based image processing system (Metamorph).

To measure each area, the region of interest was selected using a freehand selection tool, the area was automatically computed by selecting the measure command. The measurements for primary regions of interest were right hemisphere, left hemisphere, total infarct, subcortical infarct, total penumbra and subcortical penumbra. After all regions of interest were measured for all seven slices of the brain, they were sorted by slice number and the corresponding regions of interest using a custom made Excel™ macro. This macro calculates the cortical penumbra, cortical infarct and total ischemic damage for each slice; the corresponding areas of each rat brain were added together to produce a single measurement for each area. Since the ipsilateral hemisphere is swollen following MCAO, edema volume was calculated and reported as the volumetric differences between the right and left hemispheres of each brain slice. Using the % of hemispheric swelling all the volumes were corrected for the edema.

The volume of the damage was determined using the calculations below for each rat's brain.

post hoc Bonferroni's multiple comparisons or by the non-parametric Dunnelt's test (between control and the drug treated groups).

Test compounds of the present invention were administered by intravenous osmotic pump implantation, and IV infusion. Certain compounds of the present invention such as:

3-(6-Hydroxy-2-methyl-3,4,7,8,9,10-hexahydro-7,10-methano-2H-benzo[h]chromen-2-yl)-propionic acid methyl ester;

3-(6-Hydroxy-2-methyl-3,4,7,8,9,10-hexahydro-7,10-methano-2H-benzo[h]chromen-2-yl)-propionic acid methyl;

3-(6-Hydroxy-2-methyl-3,4,7,8,9,10-hexahydro-7,10-ethano-2H-benzo[h]chromen-2-yl)-propionic acid;

2,2-Dimethyl-3,4,7,8,9,10-hexahydro-7,10-methano-2H-benzo[h]chromen-6-ol;

2,2-Dimethyl-3,4,7,8,9,10-hexahydro-7,10-ethano-2H-benzo[h]chromen-6-ol;

when tested as described above provided a reduction in total infarct volume of at least about 30% at doses in the range of 10 μg/kg to 40 mg/kg.

Example 7

Interleukin-1β Microglial Cell Assay

Materials and Equipment

A. Materials for Cell Preparation and Experiment

Mouse microglial cell line
DMEM High Glucose media (Gibco Catalog #11965-092)
FBS (Hyclone Catalog #SH30070.03)
100× Penicillin/Streptomycin (Gibco Catalog #15140-122).
LPS (Sigma Catalog #L2537)
Interferon-gamma (Sigma Catalog #I4777)

| Measurement | Equation | Corrected Value(s) |
|---|---|---|
| Cortical Penumbra (C.P.) | Total Penumbra (T.P.) − Subcortical Penumbra (S.P.) | $T.P._{corr} = (T.P. \times \% H.S./100)$<br>$C.P._{corr} = C.P. − (C.P. \times \% H.S./100)$<br>$S.P._{corr} = S.P. − (S.P. \times \% H.S./100)$ |
| Cortical Infarct | Total Infarct (T.I.) − Subcortical Infarct (S.I.) | $T.I._{corr} = T.I. − (T.I. \times \% H.S./100)$<br>$S.I._{corr} = S.I. − (S.I. \times \% H.S./100)$<br>$C.I._{corr} = C.I. − (C.I. \times \% H.S./100)$ |
| Total Ischemic Damage (T.I.D.) | Total Penumbra + Total Infarct | $T.I.D._{corr} = T.I.D. − (T.I.D. \times \% H.S./100)$ |
| Total Volume (mm³) | Each value is multiplied by 2 (the thickness of the tissue). | |
| Edema Volume | The volumetric differences between the sum of right and left hemispheres determines the edema volume. | |
| % Hemispheric swelling (H.S.) | Edema × 100/left hemisphere | |

F. Statistical Analysis

Sample size was chosen to achieve a 90% probability of significant results. The measurements, which represented the same region of interest in seven slices of each rat's brain were added together to yield a single measurement for total infarct, subcortical infarct, cortical infarct, total penumbra, subcortical penumbra, cortical penumbra, total ischemic damage and edema in each animal. Group data was presented as means±SEM. Differences at the level of $p<0.05$ were considered statistically significant. Between groups comparison of each region of interest are carried out by unpaired student t test (between two groups) or one way ANOVA followed by Cell Tracker Green (Molecular Probes Catalog #C2925)
HBSS buffer (950 ml Pyrogen-free water, 2.44 g/L MgCl2.6H20, 3.73 g/L KCl, 59.58 g/L Hepes, 58.44 g/L NaCl, 1.36 g/L KH2PO4, 1.91 g/L CaCl2 .2H2O and pH to 4.5 with HCl)
Sterile 96-well plates precoated with poly-D-lysine (Corning Catalog #3665)
96-well deep well mother plate, DyNA Block 1000 (VWR Catalog #40002-008)

B. Materials for Il-1 beta Elisa

Mouse IL-1 beta Duo Set (R & D Systems Catalog #DY401)
Substrate Solution (R & D Systems Catalog #DY 999)

Bovine Serum Albumin fraction V (BSA V) (Sigma Catalog #A4503)
96-well Costar EIA high binding plates (VWR Catalog #29442-302)
Plate seal (VWR Catalog #29442-310)
PBS (Irvine Scientific Catalog #9240)
Cell Culture Grade Water (Irvine Scientific Catalog #9312)
Tween 20 (Sigma Catalog #P 1379)
Sucrose (Sigma Catalog #S7903)
Sodium Azide (Sigma Catalog #S 8032)
$H_2SO_4$ 5N (VWR Catalog #JT 5691-2)

Experimental Preparation and Procedure:
LPS Activation:
Mouse microglial cells were seeded in poly-D-lysine coated 96-well plates at a density of 10,000 cells/well and allowed to attach for 24 hours. Cells were stimulated by addition of LPS (10 μg/ml) and IFN gamma (10 ng/ml) in the presence or absence of test article. The cells were then incubated for 24 hours at 37oC, after which time the media was removed and used for cytokine determination as described below.

Cell Viability:
Viability of mouse microglial cells after exposure to the test article was determined using a fluorescent viability dye, Cell Tracker Green. Cell Tracker Green was used at a working concentration of 5 μM in 1× HBSS. Cells were washed once with HBSS (200 μl/well) and 100 μl Cell Tracker Green was added to each well. Cells were then incubated at 37° C. for 30 minutes, after which time the Cell Tracker was removed and the cells were washed once with HBSS (200 μl/well). 100 μl fresh HBSS was added to each well and the plate was read on a Fluoroskan plate reader using an excitation wavelength of 485 nm and an emission wavelength of 538 nm.

Mouse IL-1beta Elisa:
Solutions:
Wash Buffer: PBS 1 L+500 μl Tween 20 (final 0.05%) pH 7.2-7.4.
Blocking Buffer: 500 ml PBS+5 g BSA V (1%)+25 g Sucrose (5%)+0.25 g Sodium Azide (0.05%).
Reagent Diluent: 500 ml PBS+5 g BSA V (1%) pH 7.2-7.4 and filter sterilize through 0.2 μm.
Stop Solution: 2N sulfuric acid.

Duo Set Preparations:
1. The IL-1β capture antibody was reconstituted in 1 ml of PBS to give a final concentration of 720 μg/ml, and the working concentration was 4 μg/ml. For coating one 96-well plate (at 100 μl/well) 56 μl of the 720 μg/ml stock was diluted into 10 ml of PBS.
2. The IL-1β standards were reconstituted in 0.5 ml of Reagent Diluent (70 ng/ml). For a high standard of 1 ng/ml (2wells at 100 μl each + enough for series dilution) 7.1 μl of the 70 ng/ml standard were diluted into 0.5 ml of Reagent Diluent
3. The IL-1β detection antibody was reconstituted in 1 ml of Reagent Diluent to give a final concentration of 18 μg/ml and the working concentration is 100 ng/ml. For one 96-well plate (at 100 μl/well) 56 μl of the 18 μg/ml stock was diluted into 10 ml of Reagent Diluent.

IL-1.beta ELISA Procedure

Plate Preparation:
The Costar EIA Hi-binding plate was coated with capture antibody at 4 μg/ml. Each well was coated with 100 μl, and the plate was sealed and incubated overnight at room temperature.

Each well was aspirated and washed 3× with Wash Buffer. Each well was filled to the top, dispensed, and any remaining buffer was removed by inverting the plate and gently blotting against clean paper towels.
Non-specific binding sites were blocked by adding 300 μl of Blocking Buffer to each well, and after sealing incubating for at least 1 hour at room temperature.
After washing the plate was now ready for the samples.

Assay Procedure:
100 μl of either standard or sample were added in each well of the capture-coated and pre-blocked plate. The plate was sealed and incubated for 2 hours at room temperature, followed with washing.
100 μl of the detection antibody (100 ng/ml) were added to each well.
The plate was sealed and incubated at room temperature for 2 hours, followed with washing.
100 μl of the working dilution of Streptavidin-HRP was added, and the plate was sealed and incubated in the dark for 20 minutes at room temperature, followed with washing.
The fresh Substrate Solution was prepared by mixing Color Reagent A ($H_2O_2$) and Color Reagent B (Tetramethylbenzidine) in a 1:1 ratio. 100 μl of this Substrate Solution mixture was added to each well and the plate was incubated in the dark for 20 minutes at room temperature.
50 μl of Stop Solution was added to each well, mixing was ensured by gently tapping.
Each plate was read with the Spectramax once at 450 nm.

Results
When tested as described above, compounds of the present invention, such as:
3-[7-(2-Methoxycarbonyl-ethyl)-2,7-dimethyl-2,7,9,10,11,12-hexahydro-1,8-dioxa-0-12-methano-triphenylen-2-yl]-propionic acid methyl ester;
3-[6-Hydroxy-2-methyl-5-(3-methyl-but-2-enyl)-3,4,7,8,9,10-hexahydro-7,10-methano-2H-benzo[h]chromen-2-yl]-propionic acid;
3-(6-Hydroxy-2-methyl-3,4,7,8,9,10-hexahydro-7,10-propano-2H-benzo[h]chromen-2-yl)-propionic acid;
2,2-Dimethyl-5-(3-methyl-but-2-enyl)-3,4,7,8,9,10-hexahydro-7,10-methano-2H-benzo[h]chromen-6-ol;
Acetic acid 2,2-dimethyl-5-(3-methyl-but-2-enyl)-3,4,7,8,9,10-hexahydro-7,10-methano-2H-benzo[h]chromen-6-yl ester; and
2,2-Dimethyl-5-(3-methyl-butyl)-3,4,7,8,9,10-hexahydro-7,10-methano-2H-benzo[h]chromen-6-ol;

inhibited IL-1 beta production with an $EC_{50}$ of 20 μM or less.

Example 8

Rat Paw Edema Assay

Animal Preparation:
Male Sprague-Dawley rats weighing between 175 to 200 g are used in this study. Animals are allowed free access to water and commercial rodent diet under standard laboratory conditions. Room temperature is maintained at 20-23° C. and room illumination is on a 12/12-hour light/dark cycle. Animals are acclimatized to the laboratory environment 5 to 7 days prior to the study.

Experimental Procedure:

Each animal was treated by administration of vehicle, reference or test substance one hour prior to carrageenan injection, as follows:

I.V. Infusion via Femoral Vein: Anesthesia was maintained by inhalation of 3.0% isoflurane (Aerrane, Front Dodge, Iowa) in oxygen throughout the entire procedure. The exterior site of the right femoral vein was shaved and sterilized prior to surgery. A 3-cm incision is made in the right groin region and the femoral vein was isolated. The femoral vein was temporarily ligated with a micro-vascular clip, and a small incision was made on the femoral vein to introduce and advance a polyethylene (PE-50) catheter (Becton. Dickinson and Co., Sparks, Md.). The catheter was secured in place with suture (silk 5/0, Carlisle Laboratories, Farmers Branch, Tex.). The other end of the catheter was attached to a syringe filled with the saline for the bolus injection. Using a hemostat, a pocket was made subcutaneously on the back of the animal so the PE catheter could be brought up to the exteriorization point between the shoulder blade for either a bolus injection or a continuous injection by an osmotic pump.

I.P. Injection: An awake rat was held in a standard hand held position. A 23¾G needle was injected into the lower right quarter of the abdomen pass the peritoneum, slightly off the midline. To avoid organ injection, the plunger of the syringe was slightly pulled back. If no fluid is withdrawn, the content of the syringe was delivered into the abdominal cavity.

Gavage Feeding: A standard rat gavage tube (Popper & Sons Inc, NY) was attached to a 3-cc hypodermic syringe. The animal was held in a vertical position. The feeding tube was placed into the mouth and then gently advanced until it reached the stomach (the approximate insertion length of the tube should be measured prior to feeding). The content of the syringe was slowly delivered, and then the tube was withdrawn.

One hour post treatment each animal was anesthetized with 3.0% isoflurane (Aerrane, Front Dodge, Iowa) in oxygen and administered 100 µl of 1% Carrageenan Lambda type IV (Sigma Chemical Company, St. Louis, Mo.) suspension in saline, into the intraplantar surface of the right hind paw. Paw edema was measured four hours after carrageenan injection, either by measuring the increase in paw volume using a plethysmometer or the increase in paw weight using a fine scale. Immediately prior to edema measurement, the animals were euthanized via $CO_2$ asphyxiation and 500 µl blood was withdrawn by cardiac puncture for later analysis. Paw volume is determined by the extent to which water was displaced by the paw from a pre-calibrated chamber. The volume of the left hind paw (control) was subtracted from the volume of the right hind paw (carrageenan-treated) to determine the volume of carrageenan-induced edema. To measure the weight difference between paws, both hind paws were removed and weighed separately.

To minimize the variation in the model following steps were taken:

Carrageenan was made fresh every day prior to the study (2-3hours before injection).

The plethysmometer was calibrated each day prior to the study.

If carrageenan injection causes significant bleeding or a hematoma on the treated foot, the animal was excluded from the study.

Each paw was marked at the tibio-tarsal joint across the ankle prior to measurements, to ensure each paw was submerged at the same level.

If reading on the volume needs to be repeated, the paw had to be dried off completely.

Statistical Analysis

The difference of the weight or the volume between right and left paw was calculated for each animal for the analysis. Group data were presented as means±SEM and p<0.05 were considered significant. Inter-group comparisons were carried out by unpaired student t test (between two groups) or one-way ANOVA followed by post hoc Bonferroni's multiple comparisons.

Results

Certain compounds of the present invention showed significant reduction in edema 40% -71% p<0.05, when tested by this method.

Example 9

Mouse Ear Inflammatory Response to Topical Arachidonic Acid

Animals: Balb C Mice 23-28 gms, from Simonsen Labs, Gilroy, Calif.

Materials:

Arachidonic Acid, 99% pure from Porcine Liver (Sigma Aldrich) reconstituted in acetone 2 mg/20 ul (200 mg/ml).

Inhalation anesthesia: Isoflurane 3% (Baxter).

Blood Sample tubes: Microtainer tubes w/heparin (Becton Dickinson).

TNFα Elisa assay (R&D Science).

Experimental Procedure

Test compounds, positive control (arachidonic acid only) and standard (Dexamethasone @ 0.1 mg/kg) prepared in solutions of acetone, ethanol or aqueous ethanol, were applied to both sides of the right ear with an Eppendorf repipettor pipette, in a volume of 10 µl each side (20 µl total). 30 Minutes later, 10 µl of arachidonic acid was applied to both sides of the right ear (20 µl total). One hour after the application of arachidonic acid, the mice were deeply anesthetized with isoflurane and a blood sample is taken via the orbital sinuses and placed in Microtainer tubes. The animals were then euthanized by $CO_2$ inhalation and the right ears removed at the base. A uniform plug of ear tissue was obtained using a 8 mm dermal punch. The earplugs were quickly weighed to the nearest 0.1 mg and then flash frozen for TNFα determination.

Statistical Analysis:

Group data was presented as means±SEM and p<0.05 is considered significant. Inter-group comparisons were carried out by unpaired student t tests (between two groups) or ANOVA (three or more groups) followed by post hoc Dunnet's test.

Results

The compounds of the present invention, such as:

3-(6-Hydroxy-2-methyl-3,4,7,8,9,10-hexahydro-7,10-methano-2H-benzo[h]chromen-2-yl)-propionic acid methyl ester;

3-(6-Hydroxy-2-methyl-3,4,7,8,9,10-hexahydro-7,10-methano-2H-benzo[h]chromen-2-yl)-propionic acid methyl; and 3-(6-Hydroxy-2-methyl-3,4,7,8,9,10-hexahydro-7,10-ethano-2H-benzo[h]chromen-2-yl)-propionic acid;

showed significant reduction in edema (10 to 70%, p <0.05) when tested by this method.

Example 10

High Glutamate-Induced Oxidative Stress Assay (HGOS)

This procedure was used to induce high glutamate-induced oxidative stress (HGOS) in a dopaminergic neuronal cell line. Using this assay the potency and efficacy of test articles against HGOS neuronal cell injury and cell death was established in a high throughput manner.

Materials
  Dopaminergic neuronal cell lines
  DMEM-No Glucose (Life Technologies Cat #11966-025)
  L-glutamine (Life Technologies Cat #25030-081)
  L-glutamic acid, monosodium salt (Sigma Cat #G5889)
  D-glucose (Sigma Cat #G-6151)
  10× HBSS buffer(pH 7.4) (950 ml Pyrogen-free water, 2.44 g/L MgCl2.6H20, 3.73 g/L KCl, 59.58 g/L Hepes, 58.44 g/L NaCl, 1.36 g/L KH2PO4, 1.91 g/L CaCl2 .2H2O and pH to 4.5 with HCl)
  Cell Tracker Green fluorescent dye (Molecular Probes, Cat #2925). Prepare a 5 µM solution in pre-warmed HBSS just prior to use.
  Sterile 96-well plates precoated with poly-D-lysine (Corning Catalog #3665)
  96-well deep well mother plate, DyNA Block 1000 (VWR Catalog #40002-008)

Neuronal Cells
  The cells were seeded into 96-well plates at a density of 2000 per well and left to grow for 72 hours in a 33° C. incubator with 5% $CO_2$ in air atmosphere. The passage number of the cells for each assay experiment were no later than p11 in order to minimize experimental variation.

Compound Preparation in Deep-well Mother Plates
  VWRBrand DyNA Block 1000, deep well mother plates (VWR Cat. #40002-008) were used for the preparation of the test compounds.
  All compounds were dissolved in DMEM-No Glu containing 1 mM glucose, 30 mM glutamate and 1× Pen/Strep. DMEM-No Glu with 1 mM glucose and 1× P/S was used as the negative control, DMEM-No Glucose with 1 mM glucose, 100 M glutamate was used as a positive control and 100 µM Glutathione was added to the positive control as a standard. All of the procedures for this involving the making and dilution of compounds were performed using aseptic conditions and with minimal light.

Cell Preparation
  The plates were removed from the incubator and examined under the microscope for morphological appearance and density. Using an aseptic technique and an 8-channel aspirator the media was carefully removed from the cells and replaced with 200 µl of 1× HBSS. This was done as quickly as possible to prevent the cells drying out. The plates were then placed in the humidified 37° C. incubators of the Biomek 2000 Side Loader. Four plates were washed at a time so as to minimize the time that the cells were sitting in 1× HBSS prior to addition of the compound test solution.

Experimental Setup
  The Beckman Biomek workstations were used to load the compounds and controls from the mother plates onto the cell plates that were prewashed with HBSS under sterile conditions. The plates were incubated in the upper HTS incubator at 37° C. in 5% $CO_2$ for exactly 16 hrs. The following day, using the Beckman Biomek workstations, the plates were removed from the incubator. Using Cell Tracker Addition, the compounds were removed from the plates, washed once with 200 µM of pre-warmed 1× HBSS and then 100 µL of 5 µM Cell Tracker Green was added to each well. The plates were incubated at 37° C. for 30 min to allow the dye to enter the cell and be cleaved by the esterases. After washing the cells twice with prewarmed 1× HBSS, the plates were read with the 485 excitation; 538 emission filter pair on a Fluoroskan.

Certain compounds of the present invention such as:
  (6-Hydroxy-2,2-dimethyl-3,4,7,8,9,10-hexahydro-7,10-methano-2H-benzo[h]chromen-5-ylmethyl)-1-hydroxyurea;
  4-(6-Hydroxy-2,2-dimethyl-3,4,7,8,9,10-hexahydro-7,10-methano-2H-benzo[h]chromen-5-ylmethylene)-2-methyl-5-propyl-2,4-dihydro-pyrazol-3-one;
  4-[4-(6-Hydroxy-2,2-dimethyl-3,4,7,8,9,10-hexahydro-7,10-methano-2H-benzo[h]chromen-5-ylmethylene)-3-methyl-5-oxo-4,5-dihydro-pyrazol-1-yl]-benzoic acid;
  5-Hydroxy-3-(6-hydroxy-2,2-dimethyl-3,4,7,8,9,10-hexahydro-7,10-methano-2H-benzo[h]chromen-5-ylmethylene)-3H-benzofuran-2-one;
  Acetic acid 2,2-dimethyl-5-(3-methyl-but-2-enyl)-7,8,9,10-tetrahydro-7,10-methano-2H-benzo[h]chromen-6-yl ester;
  5-(2-Cyclohexylidene-ethyl)-2,2-dimethyl-3,4,7,8,9,10-hexahydro-7,10-ethano-2H-benzo[h]chromen-6-ol;
  2-[3-(Benzothiazol-2-ylsulfanyl)-propyl]-2-methyl-3,4,7,8,9,10-hexahydro-7,10-ethano-2H-benzo[h]chromen-6-ol;
  5-Bromo-2,2-dimethyl-3,4,7,8,9,10-hexahydro-7,10-ethano-2H-benzo[h]chromen-6-ol;
  5-Hydroxymethyl-2,2-dimethyl-3,4,7,8,9,10-hexahydro-7,10-methano-2H-benzo[h]chromen-6-ol;
  2-(3-Chloro-propyl)-2,5-dimethyl-3,4,7,8,9,10-hexahydro-7,10-ethano-2H-benzo[h]chromen-6-ol;
  2,2-Dimethyl-5-(3-methyl-but-2-enyl)-3,4,7,8,9,10-hexahydro-7,10-ethano-2H-benzo[h]chromen-6-ol;
  2,2-Dimethyl-7,8,9,10-tetrahydro-7,10-ethano-2H-benzo[h]chromen-6-ol;
  2-(3-Chloro-propyl)-2-methyl-3,4,7,8,9,10-hexahydro-7,10-ethano-2H-benzo[h]chromen-6-ol;
  2,2-Dimethyl-5-(3-methyl-but-2-enyl)-3,4,7,10-tetrahydro-7,10-ethano-2H-benzo[h]chromen-6-ol
  2,2-Dimethyl-5-(3-methyl-but-2-enyl)-7,8,9,10-tetrahydro-7,10-methano-2H-benzo[h]chromen-6-ol;
  2,2-Dimethyl-3,4,7,10-tetrahydro-7,10-methano-2H-benzo[h]chromen-6-ol;
  2-Methyl-2-thiophen-2-yl-3,4,7,8,9,10-hexahydro-7,10-methano-2H-benzo[h]chromen-6-ol;
  2-(3-Isobutylsulfanyl-propyl)-2-methyl-3,4,7,8,9,10-hexahydro-7,10-methano-2H-benzo[h]chromen-6-ol;
  Acetic acid 2,2-dimethyl-5-(3-methyl-butyl)-3,4,7,8,9,10-hexahydro-7,10-methano-2H-benzo[h]chromen-6-yl ester;
  5-Bromo-2,2-dimethyl-3,4,7,8,9,10-hexahydro-7,10-methano-2H-benzo[h]chromen-6-ol;
  2,2-Dimethyl-5-(3-methyl-butyl)-3,4,7,8,9,10-hexahydro7,10-methano-2H-benzo[h]chromen-6-ol;
  2,6:9,12-dimethano-9,10,11,12-tetrahydro-2,4,4-trimethylnaphtho[1,2-b]oxocan-8-ol;
  Acetic acid 2,2-dimethyl-5-(3-methyl-but-2-enyl)-3,4,7,8,9,10-hexahydro-7,10-methano-2H-benzo[h]chromen-6-yl ester, 2,2-Dimethyl-5-(3-methyl-but-2-enyl)-3,4,7,8,9,10-hexahydro-7,10-methano -2H-benzo[h]chromen-6-ol;

2-(2-Chloro-ethyl)-2-methyl-3,4,7,8,9,10-hexahydro-7,10-methano-2H-benzo[h]chromen-6-ol;

2,6:9,12-Dimethano-9,10,11,12-tetrahydro-2-methyl-naphtho[1,2-b]oxocan-8-ol;

2-[3-(Benzothiazol-2-ylsulfanyl)-propyl]-2-methyl-3,4,7,8,9,10-hexahydro-7,10-methano-2H-benzo[h]chromen-6-ol;

2-(3-Chloro-propyl)-2-methyl-3,4,7,8,9,10-hexahydro-7,10-methano-2H-benzo[h]chromen-6-ol;

2-Methyl-2-[3-(thiazol-2-ylsulfanyl)-propyl]-3,4,7,8,9,10-hexahydro-7,10-methano-2H-benzo[h]chromen-6-ol; and 3-(6-Hydroxy-2-methyl-3,4,7,8,9,10-hexahydro-7,10-propano-2H-benzo[h]chromen-2-yl)-propionic acid methyl ester;

exhibited protection against HGOS cell injury and cell death with an $EC_{50}$ in a range of 1 μM or less.

Example 11

Inflammation Assay—Cell-ELAM Assay

Endothelial-Leukocyte Adhesion Molecule (ELAM), also known as E-selectin, was expressed on the surface of endothelial cells. In this assay, lipopolysaccharide (LPS) and IL-1β were used to stimulate the expression of ELAM; test agents were tested for their abilities to reduce this expression, in accordance with studies showing that reduction of leukocyte adhesion to endothelial cell surface was associated with decreased cellular damage (e.g., Takada, M., Et al., Transplantation 64: 1520-25, 1997; Steinberg, J. B., et al., J. Heart Lung Trans. 13:306-313, 1994).

Endothelial cells may be selected from any of a number of sources and cultured according to methods known in the art; including, for example, coronary artery endothelial cells, human brain microvascular endothelial cells (HBMEC; Hess, D. C., et al., Neurosci. Lett. 213(1): 37-40, 1996), or lung endothelial cells. Cells were conveniently cultured in 96-well plates. Cells were stimulated by adding a solution to each well containing 10 μg/ml LPS and 100 pg/ml IL-1β for 6 hours in the presence of test agent (specific concentrations and time may be adjusted depending on the cell type). Treatment buffer was removed and replaced with pre-warmed Fixing Solution® (100 μl/well) for 25 minutes at room temperature. Cells were then washed 3×, then incubated with Blocking Buffer (PBS+2% FBS) for 25 minutes at room temperature. Blocking Buffer containing Monoclonal E-Selectin Antibody (1:750, Sigma Catalog #S-9555) was added to each well. Plates were sealed and stored at 4° overnight. Plates were washed 4× with 160 μL Blocking Buffer per well. Second Antibody-HRP diluted 1:5000 in Blocking Buffer was then added (100 μL/well), and plates were incubated at room temperature (protected from light) for two hours. Plates were then washed 4× with Blocking Buffer before addition of 100 μL of ABTS Substrate solution at room temperature (Zymed, Catalog #00-2024). Wells were allowed to develop for 35 minutes, before measurement at 402 nm in a Fluoroskan® Reader with shake program for 10 seconds. Positive results were recorded as a decrease in ELAM concentration in tested wells, as compared to control wells.

Certain compounds of this invention such as:

2-Methyl-2-[3-(thiazol-2-ylsulfanyl)-propyl]-3,4,7,8,9,10-hexahydro-7,10-methano-2H-benzo[h]chromen-6-ol;

2-(3-Chloro-propyl)-2-methyl-3,4,7,8,9,10-hexahydro-7,10-methano-2H-benzo[h]chromen-6-ol;

2-[3-(Benzothiazol-2-ylsulfanyl)-propyl]-2-methyl-3,4,7,8,9,10-hexahydro-7,10-methano-2H-benzo[h]chromen-6-ol;

2,6:9,12-Dimethano-9,10,11,12-tetrahydro-2-methylnaphtho[1,2-b]oxocan-8-ol;

2-(2-Chloro-ethyl)-2-methyl-3,4,7,8,9,10-hexahydro-7,10-methano-2H-benzo[h]chromen-6-ol;

2,2-Dimethyl-5-(3-methyl-but-2-enyl)-3,4,7,8,9,10-hexahydro-7,10-methano -2H-benzo[h]chromen-6-ol;

2,2-Dimethyl-5-(3-methyl-butyl)-3,4,7,8,9,10-hexahydro7,10-methano-2H-benzo[h]chromen-6-ol;

5-Bromo-2,2-dimethyl-3,4,7,8,9,10-hexahydro7,10-methano-2H-benzo[h]chromen-6-ol;

2-(3-Isobutylsulfanyl-propyl)-2-methyl-3,4,7,8,9,10-hexahydro-7,10-methano-2H-benzo[h]chromen-6-ol;

2,2-Dimethyl-3,4,7,8,9,10-hexahydro-7,10-ethano-2H-benzo[h]chromen-6-ol; and 2,2-Dimethyl-5-(3-methyl-but-2-enyl)-3,4,7,10-tetrahydro-7,10-ethano-2H-benzo[h]chromen-6-ol;

when tested as described above showed activity at an $EC_{50}$ of 30 μM or less.

Example 12

Inhibition of $LTB_4$ Production in Blood

Materials
Fresh heparinized whole blood.
NDGA, control 5-Lipoxygenase inhibitor.
A23187, calcium ionophore (Sigma C-7522)
DMSO
Methanol
Ethanol
EIA, ELISA Kit (Cayman Chemical Co., Ann Arbor, Mich., USA)

Procedure
The blood was collected in heparinized tubes or syringes to prevent clotting. Heparin was at 20 USP U/ml. About 3-5 ml of blood was collected per rat and about 0.5-0.75 ml per mouse. This assay required 200 μl/data point, therefore a 96 well plate requires 20 ml.

The Calcium ionophore A23187 was prepared as a 10 mM stock solution in DMSO and the test agent is prepared in DMSO so that ≧1 μl DMSO will be added to the well Assay
200 μl blood per well were added in a round bottom 96 well clear plastic 96 well plate followed by the test agent. After 10 minutes incubation at 37° C., 5 μl of Calcium ionophore A23187 for a final concentration of 20 μM were added and mixed, and further incubated for 30 min. After 1000×g centrifugation to pellet blood cells, 20 μl plasma was carefully removed.

20 μl plasma were added to 80 μl methanol to precipitate protein and mixed. This was further incubated 10min. at room temperature and centrifuged at 1000×g to pellet protein.

Following manufacturer's instructions, the commercially available EIA kit was used to subsequently measure the $LTB_4$ production in the samples. The $LTB_4$ levels produced in the vehicle control sample were then compared to those in which the test compound had been added. From this a percent inhibition of LTB.sub.4 production by each concentration of test compound was calculated and the $IC_{50}$ for inhibition of $LTB_4$ production for each test compound was determined.

Certain compounds of this invention such as:
2-(3-Chloro-propyl)-2-methyl-3,4,7,8,9,10-hexahydro-7,10-ethano-2H-benzo[h]chromen-6-ol;
4-(6-Hydroxy-2,2-dimethyl-3,4,7,8,9,10-hexahydro-7,10-methano-2H-benzo[h]chromen-5-ylmethylene)-2-methyl-5-propyl-2,4-dihydro-pyrazol-3-one;
2-Methyl-2-[3-(thiazol-2-ylsulfanyl)-propyl]-3,4,7,8,9,10-hexahydro-7,10-methano-2H-benzo[h]chromen-6-ol;
[3-(6-Hydroxy-2-methyl-3,4,7,8,9,10-hexahydro-7,10-methano-2H-benzo[h]chromen-2-yl)-propyl]-phosphonic acid dimethyl ester;
2-(3-Chloro-propyl)-2-methyl-3,4,7,8,9,10-hexahydro-7,10-methano-2H-benzo[h]chromen-6-ol;
2,2-Dimethyl-3,4,7,8,9,10-hexahydro-7,10-methano-2H-benzo[h]chromen-6-ol;
2-(3-Isobutylsulfanyl-propyl)-2-methyl-3,4,7,8,9,10-hexahydro-7,10-methano-2H-benzo[h]chromen-6-ol;
2-Methyl-2-thiophen-2-yl-3,4,7,8,9,10-hexahydro-7,10-methano-2H-benzo[h]chromen-6-ol;
2,2-Dimethyl-3,4,7,10-tetrahydro-7,10-methano-2H-benzo[h]chromen-6-ol;
2,2-Dimethyl-3,4,7,8,9,10-hexahydro-7,10-ethano-2H-benzo[h]chromen-6-ol;
2-(3-Chloro-propyl)-2,5-dimethyl-3,4,7,8,9,10-hexahydro-7,10-ethano-2H-benzo[h]chromen-6-ol; and
5-Bromo-2,2-dimethyl-3,4,7,8,9,10-hexahydro-7,10-ethano-2H-benzo[h]chromen-6-ol;

when tested as described above provided protection against $LTB_4$ at an EC50 of 10 µM or less.

Example 13

$LTB_4$-Cell Assay

This procedure was used for measuring the release of the leukotriene LTB4 from a neutrophil cell line using a competitive ELISA technique.

Materials and Equipments

Materials for Cell Preparation and Experiment
  MPRO cell line (ATCC, Catalog #CRL-11422)
  Calcium ionophore (A23187) (Sigma, Catalog #C7522)
  Nordihydroguaiaretic acid (NDGA) (BioMol Catalog #El101-0001)
  Retinoic Acid (all-trans) (ATRA) (Sigma, Catalog #95152)
  Sterile, tissue-culture treated 96-well plates (Corning, Catalog #3614)

Materials for LTB4 ELISA
  Precoated (Mouse Anti-Rabbit IgG) EIA 96 Well Strip Plates (Cayman, Catalog #400004)
  Leukotriene B4 AChE Tracer (Cayman Catalog #420110)
  Leukotriene B4 EIA Antiserum (Cayman Catalog #420112)
  Ellman's Reagent (Cayman Catalog #400050)
  EIA Buffer Concentrate (10×) (Cayman Catalog #400060)
  Wash Buffer Concentrate (400×) (Cayman Catalog #400062)
  Plastic plate covers (Cayman Catalog #400012)

Procedure

A mouse promyelocytic cell line (MPRO) was used in this assay. These cells are committed immature neutrophils that can be differentiated into mature neutrophils by treatment with 10 µM all-trans retinoic acid for 72 hours Following 72 hours of differentiation, cells were stimulated with 1 µM of a calcium ionophore (A23187) in the presence or absence of test compound or vehicle for 1 hour at 37° C. After this time, supernatant was removed from the cells and the LTB4 levels were determined following manufacturer's instructions, using a Leukotriene B4 EIA kit from Cayman (Cat #520111)

The negative controls were media samples from differentiated but unstimulated cells.

The compounds were screened at 5 concentrations in quadruplicate starting at 10 µM Following the procedure described above certain compounds of the present invention, such as:
2,2,-Dimethyl-3,4,7,8,9,10-hexahydro-7,10-methano-2H-benzo[h]chromen-6-ol;
2-Methyl-2-[3-(thiazol-2-ylsulfanyl)-propyl]-3,4,7,8,9,10-hexahydro-7,10-methano-2H-benzo[h]chromen-6-ol;
2-(3-Chloro-propyl)-2-methyl-3,4,7,8,9,10-hexahydro-7,10-methano-2H-benzo[h]chromen-6-ol;
2,2-Dimethyl-3,4,7,8,9,10-hexahydro-7,10-methano-2H-benzo[h]chromen-6-ol;
2-Methyl-2-[3-(pyridine-4-ylsulfanyl)-propyl]-3,4,7,8,9,10-hexahydro-7,10-methano-2H-benzo[h]chromen-6-ol;
2-(3-Isobutylsulfanyl-propyl)-2-methyl-3,4,7,8,9,10-hexahydro-7,10-methano-2H-benzo[h]chromen-6-ol;
2-Methyl-2-thiophen-2-yl-3,4,7,8,9,10-hexahydro-7,10-methano-2H-benzo[h]chromen-6-ol;
2-Methyl-2-thiazol-2-yl-3,4,7,8,9,10-hexahydro-7,10-methano-2H-benzo[h]chromen-6-ol;
2,2-Dimethyl-3,4,7,10-tetrahydro-7,10-methano-2H-benzo[h]chromen-6-ol;
2,2-Dimethyl-3,4,7,8,9,10-hexahydro-7,10-ethano-2H-benzo[h]chromen-6-ol;
2-(3-Chloro-propyl)-2-methyl-3,4,7,8,9,10-hexahydro-7,10-ethano-2H-benzo[h]chromen-6-ol;
2,2-Dimethyl-7,8,9,10-tetrahydro-7,10-ethano-2H-benzo[h]chromen-6-ol;
2,2,5-Trimethyl-3,4,7,8,9,10-hexahydro-7,10-ethano 2H-benzo[h]chromen-6-ol; and
Dimethylamino-acetic acid 2,2-dimethyl-3,4,7,8,9,10-hexahydro-7,10-ethano-2H-benzo[h]chromen-6-yl ester. were considered to be active if they exhibited inhibition of LTB4 with an $EC_{50}$ in a range of 5 µM or less.

Example 14

5-Lypoxygenase Enzyme Assay

This procedure was used for measuring the enzymatic activity of human recombinant 5-lipoxygenase using a colorimetric method based on the ferric oxidation of xylenol orange.

Materials
  96 well flat bottom microfilter plates (VWR, Catalog #62402-933 9295)
  Lipoxygenase screening assay buffer (Cayman, Catalog #760710)
  Human recombinant 5-lipoxygenase (Cayman, Catalog #60402)

Arachidonic Acid (Sigma, Catalog #A3555)
Iron (II) sulfate heptahydrate (Sigma, Catalog #F7002)
Sulfuric acid (95-98%) [18M]
Methanol Procedure Human recombinant 5-lipoxygenase (Cayman Cat #60402) was used in this assay. The test compound and/or vehicle was added to 0.5 U 5-lipoxygenase in 50 mM Tris-HCl buffer, pH 7.4. The reaction was initiated by addition of 70 μM arachidonic acid in Tris-HCl buffer, pH 7.4, and terminated after a 10 minute incubation at room temperature by addition of FOX reagent (25 mM sulphuric acid, 100 μM xylenol orange, 100 μM iron (II) sulphate, methanol:water 9:1). The yellow color of acidified xylenol orange was converted to a blue color by the lipid hydroperoxide-mediated oxidation of $Fe^{2+}$ ions and the interaction of the resulting $Fe^{3+}$ ions with the dye. The complex was allowed to form during a 1 hour incubation at room temperature with shaking. Absorbance of the $Fe^{3+}$ complex was then measured at 620 nM using a spectrophotometer.

Negative controls contained enzyme during the incubation step but substrate was not added until after the FOX reagent.

Compounds were screened at 5 concentrations in triplicate starting at 10 μM

Certain compounds of this invention such as 2,2,-Dimethyl-3,4,7,8,9,10-hexahydro-7,10-methano-2H-benzo[h]chromen-6-ol;

3-(6-Hydroxy-2-methyl-3,4,7,8,9,10-hexahydro-7,10-propano-2H-benzo[h]chromen-2-yl)-propionic acid methyl ester;

2-Methyl-2-[3-(thiazol-2-ylsulfanyl)-propyl]-3,4,7,8,9,10-hexahydro-7,10-methano-2H-benzo[h]chromen-6-ol;

3-(6-Hydroxy-2-methyl-3,4,7,8,9,10-hexahydro-7,10-methano-2H-benzo[h]chromen-2-yl)-propionic acid methyl ester;

2-(3-Chloro-propyl)-2-methyl-3,4,7,8,9,10-hexahydro-7,10-methano-2H-benzo[h]chromen-6-ol;

2-Methyl-2-[3-(ϵyridine-4-ylsulfanyl)-propyl]-3,4,7,8,9,10-hexahydro-7,10-methano-2H-benzo[h]chromen-6-ol;

2,2-Dimethyl-3,4,7,10-tetrahydro-7,10-methano-2H-benzo[h]chromen-6-ol;

2,2-Dimethyl-3,4,7,8,9,10-hexahydro-7,10-ethano-2H-benzo[h]chromen-6-ol;

2,2-Dimethyl-5-(3-methyl-but-2-enyl)-3,4,7,10-tetrahydro--7,10-ethano-2H-benzo[h]chromen-6-ol;

10-Methoxy-2,2-dimethyl-3,4,7,8,9,10-hexahydro-7,10-ethano-2H-benzo[h]chromen-6-ol;

3-(6-Hydroxy-2-methyl-3,4,7,8,9,10-hexahydro-7,10-ethano-2H-benzo[h]chromen-2-yl)-propionic acid methyl ester;

2,2-Dimethyl-7,8,9,10-tetrahydro-7,10-ethano-2H-benzo[h]chromen-6-ol;

2-(3-Chloro-propyl)-2,5-dimethyl-3,4,7,8,9,10-hexahydro-7,10-ethano-2H-benzo[h]chromen-6-ol;

5-Bromo-2,2-dimethyl-3,4,7,8,9,10-hexahydro-7,10-ethano-2H-benzo[h]chromen-6-ol; and 3-(6-Hydroxy-2-methyl-3,4,7,8,9,10-hexahydro-7,10-ethano-2H-benzo[h]chromen-2-yl)-propionic acid benzyl ester;

when tested as described above provided protection against 5-Lipoxygenase with an $IC_{50}$ of 5 μM or less.

Example 15

12/15-Lipoxygenase Enzyme Assay

This procedure was used for measuring the enzymatic activity of porcine leukocyte 12/15-lipoxygenase using a colorimetric method based on the ferric oxidation of xylenol orange.

Materials 96 well flat bottom microfilter plates (VWR, Catalog #62402-933 9295)

Lipoxygenase screening assay buffer (Cayman, Catalog #760710)

Porcine leukocyte 12/15-lipoxygenase (Cayman, Catalog #60300)

Arachidonic Acid (Sigma, Catalog #A3555)

Xylenol orange tetrasodium salt (Aldrich, Catalog #227854)

Iron (II) sulfate heptahydrate (Sigma, Catalog #F7002)

Sulfuric acid (95-98%) [18M]

Methanol

Procedure

Porcine Leukocyte 12/15-lipoxygenase (Cayman Cat #60300) was used in this assay. Test compound and/or vehicle was added to 1.3 U 12/15-lipoxygenase in 50 mM Tris-HCl buffer, pH 7.4. The reaction was initiated by addition of 70 μM arachidonic acid in Tris-HCl buffer, pH 7.4, and terminated after a 10 minute incubation at room temperature by addition of FOX reagent (25 mM sulphuric acid, 100 μM xylenol orange, 100 μM iron (II) sulphate, methanol:water 9:1). The yellow color of acidified xylenol orange was converted to a blue color by the lipid hydroperoxide-mediated oxidation of $Fe^{2+}$ ions and the interaction of the resulting $Fe^{3+}$ ions with the dye. The complex was allowed to form during a 1 hour incubation at room temperature with shaking. Absorbance of the $Fe^{3+}$ complex was then measured at 620 nM using a spectrophotometer.

Negative controls contained enzyme during the incubation step but substrate was not added until after the FOX reagent.

Compounds are screened at 5 concentrations in triplicate starting at 10 μM

Certain compounds of the present invention such as:

2,2,-Dimethyl-3,4,7,8,9,10-hexahydro-7,10-methano-2H-benzo[h]chromen-6-ol;

2-Methyl-2-[3-(thiazol-2-ylsulfanyl)-propyl]-3,4,7,8,9,10-hexahydro-7,10-methano-2H-benzo[h]chromen-6-ol;

2-Methyl-2-[3-(☐yridine-4-ylsulfanyl)-propyl]-3,4,7,8,9,10-hexahydro-7,10-methano-2H-benzo[h]chromen-6-ol;

2-(3-Isobutylsulfanyl-propyl)-2-methyl-3,4,7,8,9,10-hexahydro-7,10-methano-2H-benzo[h]chromen-6-ol;

2-Methyl-2-thiophen-2-yl-3,4,7,8,9,10-hexahydro-7,10-methano-2H-benzo[h]chromen-6-ol;

2-Methyl-2-thiazol-2-yl-3,4,7,8,9,10-hexahydro-7,10-methano-2H-benzo[h]chromen-6-ol;

2,2-Dimethyl-3,4,7,8,9,10-hexahydro-7,10-ethano-2H-benzo[h]chromen-6-ol;

2,2-Dimethyl-7,8,9,10-tetrahydro-7,10-ethano-2H-benzo[h]chromen-6-ol; and 2,2,5-Trimethyl-3,4,7,8,9,10-hexahydro-7,10-ethano 2H-benzo[h]chromen-6-ol;

were considered to be active when they exhibited inhibition of 12/15-Lipoxygenase with an $IC_{50}$ of 10 μM or less.

Example 16

3-(6-Hydroxy-2-methyl-3,4,7,8,9,10-hexahydro-7,10-methano-2H-benzo[h]chromen-2-yl)-propionic acid methyl ester

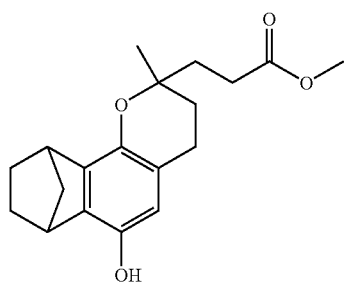

Step 1

To a solution of ethyl 2-ketopentanoate (10 mL, 71 mmol) in 100 mL of THF at −78° C. was added dropwise a solution of 1.0 M vinyl magnesium bromide (80 mL, 80 mmol). After completion of the addition, the mixture was stirred for two more hours, the cooling bath was removed and the mixture was gradually warmed to ambient temperature. After the removal of the most of the solvent, the residue was poured to 2N HCl aqueous solution, extracted with ethyl acetate and dried over $MgSO_4$ Purification by lash column chromatography on silica gel with DCM as elute afforded 4.80 grams of 5-methyl-5-vinyl-dihydro-furan-2-one. $^1$H-NMR (300 MHz, $CDCl_3$) δ (ppm): 5.824-5.917 (dd, 1H); 5.29 (d, 1H); 5.13 (d, 1H); 2.50-2.56 m, (2H); 2.07-2.18 (m, 2H); 1.48 (s, 3H).

Step 2

A mixture of 1,2,3,4-tetrahydro-1,4-methano-naphthalene-5,8-diol (1.34 g, 7.94 mmol), 1.0 mL (3.97 mmol) of $BF_3.Et_2O$ and 25 mL of dioxane was heated up to 110° C. under a nitrogen atmosphere. A solution of 5-methyl-5-vinyl-dihydro-furan-2-one (1.12 mg, 8.6 mmol) in 24 ml of dioxane was added slowly to the mixture. The addition was completed after two hours and the mixture was continued to reflux for additional 3 hours. After cooling down to room temperature, the mixture was poured to water, extracted with ethyl acetate, washed with water and dried over $MgSO_4$. After the removal of solvents, the residue was mixed with methanol/HCl and let stand overnight at room temperature. Then the solvents were removed and the residue was purified via flash column chromatography on silica gel (1:3 EtOAc/Hex) twice to give 1.30 g of 3-(6-hydroxy-2-methyl-3,4,7,8,9,10-hexahydro-7,10-methano-2H-benzo[h]chromen-2-yl)-propionic acid methyl ester. $^1$H-NMR (300 MHz, $CDCl_3$) δ (ppm): 6.29 (s. 1H), 4.70 (s, 1H), 3.68 (s, 3H), 3.52-3.46 (d, 2H), 2.69-2.55 (m, 2H), 2.52-2.47 (m, 2H), 2.00-1.64 (m, 8H), 1.43-1.15 (m, 5H). MS (ESI): 317 (M+H$^+$, 70%), 339 (M+Na$^+$, 100%).

Example 17

3-(6-Hydroxy-2-methyl-3,4,7,8,9,10-hexahydro-7,10-methano-2H-benzo[h]chromen-2-yl)-propionic acid

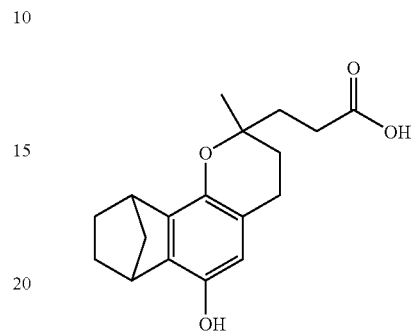

1.0 gram (3.16 mmol) of 3-(6-hydroxy-2-methyl-3,4,7,8,9,10-hexahydro-7,10-methano-2H-benzo[h]chromen-2-yl)-propionic acid methyl ester, prepared as described in Example 13, was mixed with 20 mL of 2N NaOH and 20 mL of dioxane, the mixture was stirred for 5 hours and was acidified with dilute HCl. Water and ethyl acetate were added and the organic layer was separated, washed and dried over $MgSO_4$. After the removal of solvents, the residue was further purified by flash column chromatography on silica gel (3:2 ethyl acetate/hexane) to afford 700 mg of 3-(6-hydroxy-2-methyl-3,4,7,8,9,10-hexahydro-7,10-methano-2H-benzo[h]chromen-2-yl)-propionic acid. $^1$H-NMR (300 MHz, $CDCl_3$) δ (ppm): 6.29 (s, 1H), 4.70 (s, 1H), 3.52-3.46 (d, 2H), 2.69-2.55 (m, 2H), 2.52-2.47 (m, 2H), 2.00-1.64 (m, 8H), 1.43-1.15 (m,5H); MS: 302 (M+H$^+$, 73%), 325 (M+Na$^+$, 100%).

Example 18

3-(6-Methoxymethoxy-2-methyl-3,4,7,8,9,10-hexahydro-7,10-methano-2H-benzo[h]chromen-2-yl)-propionic acid methyl ester

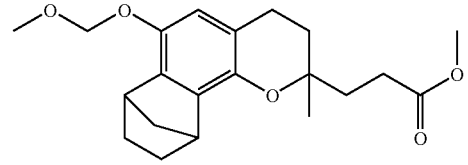

To a solution of 3-(6-hydroxy-2-methyl-3,4,7,8,9,10-hexahydro-7,10-methano-2H-benzo[h]chromen-2-yl)-propionic acid methyl ester from Example 13 (400 mg, 1.27 mmol) and diisopropyl ethylamine (DIPEA) (0.90 ml, 5 mmol) in 4 mL of DCM was slowly added chloromethyl methyl ether (0.30 mL, 3.8 mmol) at room temperature. The reaction was left over night. After the completion of reaction shown by TLC, the mixture was poured into brine and the organic layer was separated and dried over $MgSO_4$. After the removal of solvents the residue was purified through flash column chromatography on silica gel (25% of ethyl acetate in hexane) to afford 340 mg of 3-(6-methoxymethoxy-2-methyl-3,4,7,8,9,10-hexahydro-7,10-methano-2H-benzo[h]chromen-2-yl)-propionic acid methyl ester. $^1$H-NMR (300 MHz, CDCl$_3$) δ (ppm)): 6.25 (s, 1H), 4.29 (s, 1H), 3.63 (s, 3H), 2.48 (s, 1H), 3.40 (s, 1H), 2.66-2.64(m, 2H), 2.47-2.43 (m, 2H), 1.83-1.50, (m, 12H), 1.18 (s, 3H).

Example 19

2-(3-Hydroxy-propyl)-2-methyl-3,4,7,8,9,10-hexahydro-7,10-methano-2H-benzo[h]chromen-6-ol

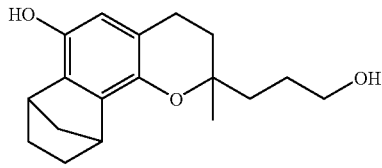

To the mixture of lithium aluminum hydride (LiAlH$_4$, 713 mg, 18 mmol) in 40 mL of dried THF under nitrogen was added drop-wise a solution of the MOM-protected methyl ester from Example 15 (2.70 g, 7.5 mmol), and the reaction mixture was stirred overnight. Ethyl acetate was slowly added to the mixture to destroy the excess of LiAlH$_4$. The mixture was filtered and the solution was washed with water and dried over MgSO4. The solvent was removed and the residue was purified via flash column chromatography on silica gel (2:3 EtOAc/Hex) to afford 2.15 grams of 6-methoxymethoxy 3-hydroxy-propyl-alcohol chroman derivative.

$^1$H-NMR (300 MHz, CDCl$_3$) δ (ppm): 6.50 (s, 1H), 5.02 (s, 2H), 3.60 (m, 2H), 3.44 (s, 2H), 3.41 (s, 3H), 2.83 (s, 1H), 2.64 (m, 2H), 1.80-1.50 (m, 12H), 1.25 (s, 3H); MS: 333 (M+H$^+$, 10%), 355 (M+Na$^+$, 100%)

A mixture of 200 mg of the above synthesized MOM-protected alcohol, 6.5 mL of methanol and 6 drops of concentrated HCl was stirred overnight. The solvent was removed carefully and the residue was partitioned with ethyl acetate and water. The ester layer was separated and washed with water and dried over Na$_2$SO$_4$. Removal of solvent followed by flash column chromatography on silica gel (2:3 ethyl acetate/hexane) afforded 160 mg of 2-(3-hydroxy-propyl)-2-methyl-3,4,7,8,9,10-hexahydro-7,10-methano-2H-benzo[h]chromen-6-ol.

$^1$H-NMR (300 MHz, CDCl$_3$) δ (ppm): 6.29 (s, 1H), 4.35 (s, 1H), 3.56-3.70 (m, 2H), 3.50 (s, 1H), 3.40 (s, 1H), 2.66-2.72 (m, 2H), 1.52-1.90 (m, 12H), 1.23-1.28 (d, 3H)
MS: 289 (M+H$^+$, 80%), 311 (M+Na$^+$, 75%)

Example 20

[3-(6-Hydroxy-2-methyl-3,4,7,8,9,10-hexahydro-7,10-methano-2H-benzo[h]chromen-2-yl)-propyl]-phosphonic acid dimethyl ester

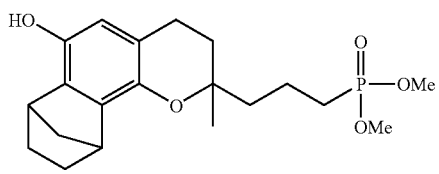

Step 1
To a mixture of 6-methoxymethoxy 3-hydroxy-propyl-alcohol chroman derivative (287 mg, 0.86 mmol), prepared as described above, triethylamine (18.5mL, 1.3 mmol) and 5 ml of DCM, was added methane sulfonyl chloride (8 mL, 1.04 mmol). After 5 hours of stirring the mixture was poured into water, extracted with ethyl acetate, and dried over MgSO$_4$. Removal of solvent afforded 300 mg of the mesylate derivative. This product is pure enough to go directly to next step.

Step 2
A mixture of 800 mg of methanesulfonate derivative from Step 1, 1.0 gram of sodium iodide and 20 mL of acetone was stirred overnight. The solvent was removed, and a mixture of ethyl acetate and water was added to the residue, the organic layer was separated and dried. The solvents were removed and the residue was purified via flash column chromatography on silica gel using 15:1 hexane/ethyl acetate to afford 520 mg of the iodide derivative.

Step 3
A mixture of 650 mg of the iodide derivative from Step 2 and 5mL of trimethyl phosphite was refluxed for 4 hours followed by distillation of the excess of the starting materials. The mixture was cooled to room temperature, and was purified by flash column chromatography on silica gel (5% MeOH/DCM) to afford 610 mg of [3-(6-methoxymethoxy-2-methyl-3,4,7,8,9,10-hexahydro-7,10-methano-2H-benzo[h]chromen-2-yl)-propyl]-phosphonic acid methyl ester. $^1$H-NMR (300 MHz, CDCl$_3$) δ (ppm): 6.38 (s, 1H), 5.11(s, 2H), 3.72-3.82 (m, 6H) 3.53 (s, 3H), 2.62-2.68 (m, 4H), 1.70-1.84 (m, 12H), 1.22-1.28 (d, 3H); MS: 425 (M+H$^+$, 65%), 403 (M+Na$^+$, 100%).

Step 4
190 mg of 6-methoxymethoxy-dimethyl phosphonate derivative from Step 3 was treated with a mixture of 20 mL of MeOH and 20 drops of concentrate HCl for overnight. After removal of most of the solvent, ethyl acetate was added and then washed with water, and dried over MgSO$_4$. After the removal of solvents the residue was purified by flash column chromatography on silica gel (10% MeOH/DCM) to afford 90 mg of [3-(6-hydroxy-2-methyl-3,4,7,8,9,10-hexahydro-7,10-methano-2H-benzo[h]chromen-2-yl)-propyl]-phosphonic acid dimethyl ester. $^1$H-NMR (300 MHz, CDCl$_3$) δ (ppm): 6.38 (s, 1H), 5.323 (s, 1H), 3.72-3.82 (m, 6H) 3.50-3.54 (m, 2H), 2.62-2.68 (m, 4H), 1.70-1.84 (m, 12H), 1.22-1.28 (s, 3H)
MS: 381 (M+H$^+$, 100%), 403 (M+Na$^+$, 36%)

Example 21

[3-(6-Hydroxy-2-methyl-3,4,7,8,9,10-hexahydro-7,10-methano-2H-benzo[h]chromen-2-yl)-propyl]-phosphonic acid A mixture of 90 mg of dimethyl phosphonate, prepared as described above, 0.3 mL of trimethylsilylbromide in 6 mL of DCM was stirred at room temperature for 2 hours. The solvent and excess of trimethylsilylbromide was evaporated and the residue was mixed with 3 mL of 1:3 MeOH/H2O and was then dried overnight to afford [3-(6-hydroxy-2-methyl-3,4,7,8,9,10-hexahydro-7,10-methano-2H-benzo[h]chromen-2-yl)-propyl]-phosphonic acid as a white solid. $^1$H-(NMR, CD$_3$OD) δ (ppm): 6.05 (s, H), 4.87 (s, 2H), 3.27-3.29 (d, 2H), 3.12-3.13 (m, 1H), 2.48 (m, 2H), 1.70-1.84 (m, 12H), 1.22-1.28 (d, 3H). MS: 353 (M+H$^+$, 100%).

Example 22

2-Methyl-2-[3-(thiazol-2-ylsulfanyl)-propyl]-3,4,7,8,9,10-hexahydro-7,10-methano-2H-benzo[h]chromen-6-ol

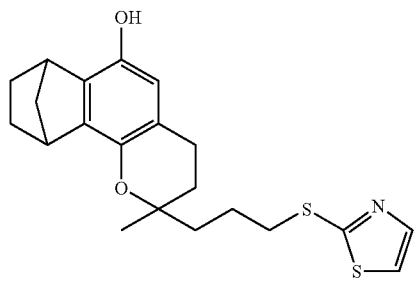

Step 1

A mixture of 50 mg methanesulfonate prepared as described above, 86 mg of LiBr and 1.8 ml of acetone was stirred overnight. After the removal of solvent the residue was purified via flash column chromatography on silica gel (1:5 EtOAc/Hex) to afford 29 mg of the 6-methoxymethoxy-propylbromide derivative. 1H-NMR (300 MHz, CDCl$_3$) δ (ppm): 6.60 (s, 1H), 5.10 (s, 2H), 3.60 (m, 2H), 3.54 (m, 3H), 2.64 (m, 4H), 1.80-1.50 (m, 12H), 1.25 (s, 3H)

Step 2

A mixture of bromide from Step 1 (190 mg, 0.48 mmol), 76 mg (0.647 mmol) of thiazole-2-thiol, 200 mg (1.45 mmol) of K$_2$CO$_3$, small amount of NaI and 5 ml of acetone was stirred overnight. The mixture was filtered and the filtrate was concentrated by evaporation. The residue was purified via flash column chromatography on silica gel (1:3 EtOAc/Hex) to afford 200 mg of the 6-methoxymethoxy-2-[3-(thiazol-2-ylsulfanyl)-propyl chroman derivative. $^1$H-NMR (300 MHz, CDCl$_3$) δ (ppm): 7.71 (s, 1H), 7.18 (s, 1H), 6.56 (s, 1H), 5.12 (s, 2H), 3.54 (s, 3H), 3.10-3.28 (m, 2H), 2.65-2.77 (m, 2H), 1.63-2.01 (m, 8H), 1.58 (s, 3H), 1.18-1.32 (m, 6H)

Step 3

200 mg of thiazole from Step 2 was treated with a mixture of 20 mL of MeOH and 20 drops of concentrate HCl and stirred overnight. After removal of the solvent, ethyl acetate was added and the mixture was washed with water and dried over MgSO$_4$ to give 140 mg of 2-methyl-2-[3-(thiazol-2-ylsulfanyl)-propyl]-3,4,7,8,9,10-hexahydro-7,10-methano-2H-benzo[h]chromen-6-ol. $^1$H-NMR(300 MHz, CDCl$_3$) δ (ppm): 7.69 (s, 1H), 7.23 (s, 1H), 6.32 (s, 1H), 4.19 (s, 1H), 3.46-3.54 (d, 2H), 3.23-3.26 (m, 2H), 2.69-2.72 (m, 2H), 2.07-1.77 (m, 12H), 1.31-1.24 (m, 6H); MS: 388 (M+H$^+$, 100%).

Example 23

4-(6-Hydroxy-2-methyl-3,4,7,8,9,10-hexahydro-7,10-methano-2H-benzo[h]chromen-2-yl)-butane-1-sulfonic acid dimethylamide

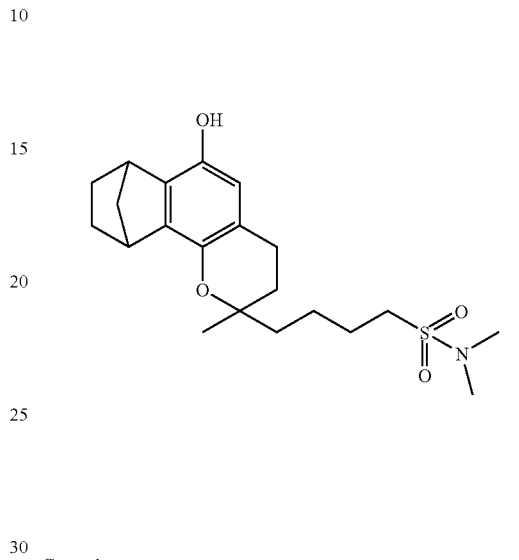

Step 1

To a solution of N,N-dimethylmethanesulfonamide (369 mg, 3 mmol) in 4ml of THF at −78° C. was added a solution of 2.5 M n-BuLi in hexane (0.8 mL, 2 mmol). The mixture was stirred at this temperature for one hour and then a solution of the methanesulfonate prepared as described above (205 mg, 0.5 mmol) in 2 mL of THF was added and the mixture was gradually warmed to room temperature and stirred overnight. The mixture was poured into water, extracted with ethyl acetate, and dried over MgSO$_4$. After the removal of solvent, the residue was purified via flash column chromatography on silica gel with 1:2 ethyl acetate/hexane to afford 75 mg of the bicyclic 6-methoxymethoxy-2-butyldimethylsulfonamide chroman derivative. $^1$H-NMR (300 MHz, CDCl$_3$) δ (ppm): 6.30 (s, 1H), 3.50-3.54 (m, 2H), 2.88-3.00 (m, 1H), 2.60-2.70 (m, 4H), 1.25-1.84 (m, 12H), 1.22-1.28 (d, 3H); MS: 394 (M+H$^+$, 100%), 416 (M+Na$^+$, 70%)

Step 2

A mixture of 70 mg of 6-methoxymethoxy-2-butyldimethylsulfonamide chroman derivative from Step 1, 8 ml of methanol and 0.1 ml of conc. HCl was stirred overnight. The solvent was removed and the residue was partitioned with ethyl acetate and water. The ester layer was separated and washed with water and dried over Na$_2$SO$_4$. Removal of the solvent followed by flash column chromatography on silica gel (3:2 EtOAc/hexane) afforded 31 mg of 4-(6-hydroxy-2-methyl-3,4,7,8,9,10-hexahydro-7,10-methano-2H-benzo[h]chromen-2-yl)-butane-1-sulfonic acid dimethylamide $^1$H-NMR (300 MHz, CDCl$_3$) δ (ppm): 6.29 (s, 1H), 3.54 (s, 1H), 3.45(s, 1H), 2.88-2.99 (m, 1H), 2.80 (m, 6H), 2.60-2.72 (m, 4H), 1.50-1.88(m, 12H), 1.23-1.28 (d, 3H), 1.22-1.31 (2H); MS: 394 ( M+H$^+$100%), 416 (M+Na$^+$, 70%)

Example 24

2-(3-Chloro-propyl)-2-methyl-3,4,7,8,9,10-hexahydro-7,10-methano-2H-benzo[h]chromen-6-ol

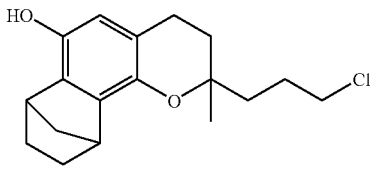

Step 1

To a solution of 5-chloro-pentane 2-one (13.4 mL, 100 mmol) in 100 ml of THF at −78° C. was added dropwise a solution of 1M vinyl magnesium bromide (120 mL, 120 mmol), the mixture was stirred for two hours, and the cooling bath was removed to let the mixture gradually warm to room temperature. After the removal of the solvent, the residue was poured to 2N HCl, extracted with ethyl acetate and dried over MgSO$_4$ Purification by flash column chromatography on silica gel with DCM as elute afforded 4.80 grams of 6-chloro-3-methyl-hex-1-en-3-ol. 1H-NMR (300 MHz, CDCl$_3$) δ (ppm): 5.86-5.90 (dd, 1H); 5.29 (d, 1H), 5.13 (d, 1H), 3.50-3.59 (t, 3H); 1.87-1.83 2.18 (m, 2H); 1.63-1.69 (m, 2H), 1.31 (s, 3H)

Step 2

A mixture of 1,2,3,4-tetrahydro-1,4-methano-naphthalene-5,8-diol (1.34 g, 794 mmol), 1.0 mL (3.97 mmol) of BF$_3$.Et$_2$O and 25 ml of dioxane was heated up to 110° C. under a N$_2$ atmosphere. A solution of 6-chloro-3-methyl-hex-1-en-3-ol (1.12 g, 8.6 mmol) in 24 ml of dioxane was added slowly to the mixture. The addition was completed after two hours and the mixture was continued to reflux for an additional 3 hours. After cooling down to room temperature, the mixture was poured to water, extracted with ethyl acetate, washed with water and dried over MgSO$_4$. After removal of the solvents, the residue was mixed with methanol/HCl and let stand overnight at room temperature. After the removal of the solvents the residue was purified via flash column chromatography on silica gel (1:3 EtOAc/Hex) twice to give 1.30 g of 2-(3-chloro-propyl)-2-methyl-3,4,7,8,9,10-hexahydro-7,10-methano-2H-benzo[h]chromen-6-ol. $^1$H-NMR (300 MHz, CDCl$_3$) δ (ppm): 6.39 (s, 1H), 4.27 (s, 1H), 3.63-3.47 (m, 4H), 2.73-2.70 (m, 2H), 2.00-1.47 (m, 8H), 1.43-1.15 (m, 4H); MS: 307 (M+H$^+$, 100%).

Example 25

2-[3-(Benzothiazol-2-ylsulfanyl)-propyl]-2-methyl-3,4,7,8,9,10-hexahydro-7,10-methano-2H-benzo[h]chromen-6-ol

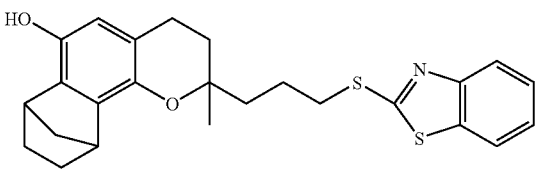

Step 1

A mixture of 612 mg of the 3-chloropropyl chroman derivative prepared as described above (2 mmol), 1.5 gram of sodium iodide (10 mmol) and 8 ml of acetone was refluxed for 6 hours. The mixture was cooled down to room temperature and the solvent was removed by evaporation. The residue was dissolved in DCM, washed with water, and the organic layer was separated and dried over MgSO$_4$. Removal of solvent afforded the crude iodide which was used directly in the next step.

Step 2

A mixture of 100 mg of 3-iodopropyl chroman derivative from Step 1 (0.25 mmol), 66 mg of benzothiazole-2-thiol (0.39 mmol), and 55 mg of K$_2$CO$_3$ (0.39 mmol) in 1.5 ml of DMF was stirred overnight. The mixture was poured into water and extracted with DCM. Purification by flash column chromatography on silica gel (3:1 Hexane/EtOAc) of the residue gave 55 mg of pure 2-[3-(benzothiazol-2-ylsulfanyl)-propyl]-2-methyl-3,4,7,8,9,10-hexahydro-7,10-methano-2H-benzo[h]chromen-6-ol. $^1$H-NMR (300 MHz, CDCl$_3$) δ (ppm): 7.86 (m, 1H), 7.78 ( m, 1H), 7.41 (m, 1H), 7.26 (m, 1H), 6.33 (s, 1H), 4.23 (s, 1H), 3.50-3.42 (m, 2H), 3.38-3.25 (m, 2H), 2.80 (m, 2H), 2.07-1.77 (m, 12H), 1.31-1.24 (m, 6H); MS: 437.(M+H$^+$, 100%).

Example 26

1-{3-[3-(6-Hydroxy-2-methyl-3,4,7,8,9,10-hexahydro-7,10-methano-2H-benzo[h]chromen-2-yl)-propylsulfanyl]-2-methyl-propionyl}-pyrrolidine-2-carboxylic acid

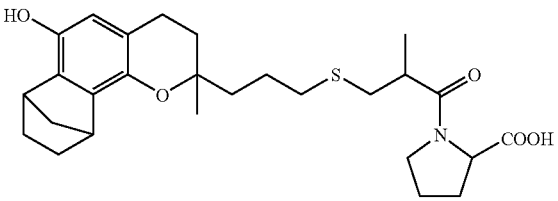

A mixture of 200 mg of iodide (0.50 mmol), 163 mg 1-(3-mercapto-2-methyl-propionyl)-pyrrolidine-2-carboxylic acid (0.75 mmol), 97 mg of K$_2$CO$_3$ (0.70 mmol) in 2.0 ml of DMF was stirred overnight. The mixture was poured into water and extracted with DCM. Purification by flash column chromatography on silica gel (4% of MeOH/DCM) of the residue gave 65 mg of 1-{3-[3-(6-hydroxy-2-methyl-3,4,7,8,9,10-hexahydro-7,10-methano-2H-benzo[h]chromen-2-yl)-propylsulfanyl]-2-methyl-propionyl }-pyrrolidine-2-carboxylic acid. $^1$H-NMR (300 MHz, CDCl$_3$) δ (ppm): 6.31 (s, 1H), 4.65 (m, 1H), 4.55 (m, 2H), 4.19 (s, 2H), 3.50-3.42 (m, 2H), 2.90 (m, 1H), 2.80-2.67(m, 5H), 2.43-2.35 (m, 2H), 2.07-1.77 (m, 12H), 1.31-1.24 (m, 10H);MS: 488 (M+H$^+$, 100%), 510 (M+Na$^+$, 65%).

Example 27

3-6-Hydroxy-2-methyl-3,4,7,8,9,10-hexahydro-7,10-propano-2H-benzo[h]chromen-2-yl)-propionic acid methyl ester

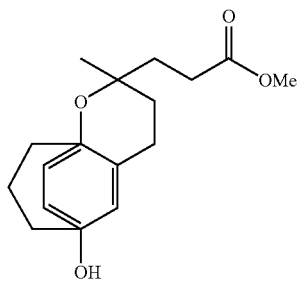

Step 1

A sealed reaction vessel containing quinone (700 mg, 6.48 mmol) and cycloheptadiene (731 mg, 7.76 mmol) was heated in a microwave reactor (Personal Chemistry) to 170° C. for 15 min. The solvent was removed under reduced pressure to afford a dark brown solid containing desired product, hydroquinone and impurities. The crude products from 17 runs of such reaction (11.9 g, 0.11 mol) were combined and chromatographed to afford a brown solid (8 g) containing the desired compound and quinone. To this material in 150 mL dry acetone was added 7 g of $K_2CO_3$ and the mixture was heated to reflux for 2 h and cooled and concentrated under reduced pressure. The crude product was purified by column chromatography on silica gel (hexanes/EtOAc=5:1) to afford of 5,8-dihydro-5,8-propano-naphthalene-1,4-diol as a light brown solid (4.6 g). MS (ESI) m/z: 203 (M+H+, 100%)

Step 2

To a solution of the hydroquinone prepared in Step 1 in 100 mL ethanol was added Pd/C (250 mg) charged with hydrogen. The reaction was stirred under hydrogen for 5 h and the solid was removed through filtration. The solvent was removed and the residue was chromatographed to afford 5,6,7,8-tetrahydro-5,8-propano-naphthalene-1,4-diol as a light brown solid (3.9g). $^1$H-NMR (300 MHz, $CDCl_3$) δ (ppm): 6.51 (s, 2H), 3.33 (bs, 2 H), 1.96-1.89 (m, 2 H), 1.70-1.57 9 (m, 6 H), 1.18 (m, 2 H);

MS (ESI) m/z: 205 (M+H+, 100%).

Step 3

To a solution of 5,6,7,8-tetrahydro-5,8-propano-naphthalene-1,4-diol from Step 2 (3.7 g, 18.1 mmol) in 80 mL of dioxane was added $BF_3.Et_2O$ (7.7 g, 54.5 mmol). The mixture was heated to reflux and vinyl lactone (2.28 g, 18.1 mmol, in 20 mL dioxane) was added over a period of 60 min. The reaction was stirred at reflux for 16 h and cooled. It was quenched on to ice (300 g) and extracted with DCM (3×120 mL). The combined organic layers were dried over $Na_2SO_4$, concentrated and dried under high vacuum. To this crude material in 250 mL MeOH was added 30 mg of toluenesulfonic acid. The mixture was heated to reflux for 15 h and cooled. After solvent removal the residue was chromatographed (hex/EtOAc=7:1) to afford 3-(6-hydroxy-2-methyl-3,4,7,8,9,10-hexahydro-7,10-propano-2H-benzo[h]chromen-2-yl)-propionic acid methyl ester as a green sticky oil (1.4 g). $^1$H-NMR (300 MHz, $CDCl_3$,) δ (ppm): 6.41 (s,1 H), 3.70 (s, 3 H), 3.53 (m, 1 H), 3.41 (m, 1 H), 2.72 (m, 2 H), 2.52 (m, 2 H), 2.09-1.62 (12 H), 1.29-1.24 (5 H); $^{13}$C-NMR δ(ppm): 174.5, 144.0, 142.9, 132.8, 128.6, 118.5, 112.4, 74.1, 51.7, 34.5, 33.9, 31.9, 29.5, 28.6, 26.3, 26.0, 24.0, 23.4, 22.7, 22.3; MS (ESI) m/z: 345 (M+H+, 100%)

Example 28

2-(3-Hydroxy-propyl)-2-methyl-3,4,7,8,9,10-hexahydro-7,10-propano-2H-benzo[h]chromen6-ol

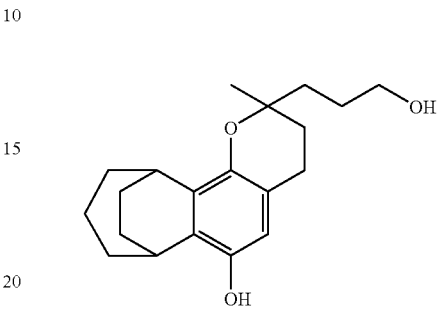

To a solution of 3-(6-hydroxy-2-methyl-3,4,7,8,9,10-hexahydro-7,10-propano-2H-benzo[h]chromen-2-yl)-propionic acid methyl ester (212 mg, 0.61 mmol) in 50 mL dry THF was added $LiAlH_4$ in 8 portions over a period of 20 min. The reaction was stirred for 2 h and quenched onto ice (80 g). The mixture was extracted with EtOAc (3×50 mL) and combined organic layers were dried over $Na_2SO_4$ and concentrated. The crude product was chromatographed (hexane/EtOAc=6:1) to yield 2-(3-hydroxy-propyl)-2-methyl-3,4,7,8,9,10-hexahydro-7,10-propano-2H-benzo[h]chromen-6-ol as a light yellow oil (169 mg). $^1$H-NMR ($CDCl_3$, 300 MHz) δ (ppm): 6.39 (s, 1 H), 5.78 (s, 1 H), 3.69 (m, 2 H), 3.54 (m, 1 H), 3.40 (m, 1 H), 2.69 (m, 2 H), 2.45 (ws, 1 H), 1.90-1.60 (m, 14 H), 1.26 (m, 5 H); $^{13}$C-NMR δ (ppm): 144.3, 142.9, 132.7, 128.9, 118.6, 112.6, 75.0, 63.3, 36.1, 35.7, 32.1, 32.0, 31.9, 29.4, 28.7, 26.8, 26.4, 26.1, 24.2, 23.6, 22.8, 22.4; MS (ESI) m/z: 317 (M+H+, 100%).

Example 29

3-(6-Hydroxy-2-methyl-3,4,7,8,9,10-hexahydro-7,10-propano-2H-benzo[h]chromen-2-yl)-propionic acid

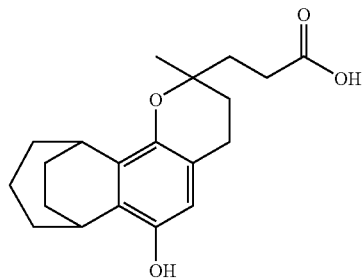

To a solution of 3-(6-Hydroxy-2-methyl-3,4,7,8,9,10-hexahydro-7,10-methano-2H-benzo[h]chromen-2-yl)-propionic acid methyl ester (235 mg, 0.68 mmol) in 5 mL of dioxane was added a solution of NaOH (41 mg, 1.02 mmol) in 400 mL water. The resulting suspension was vigorously stirred for 15 h and quenched by adding 50 mL of saturated $NaH_2PO_4$ solution. The mixture was extracted with EtOAc (3×50 mL) and the organic layers were dried over Na$_2$SO$_4$ and concentrated. The crude product was purified by chromatography on silica gel to afford 3-(6-hydroxy-2-methyl-3,4,7,8,9,10-hexahydro-7,10-propano-2H-benzo[h]chromen-2-yl)-propionic acid as a white sticky solid (184 mg). $^1$H-NMR (CDCl$_3$, 300 MHz) δ (ppm): 7.71 (ws, 1 H), 6.41 (s, 1 H), 3.54 (m, 1 H), 3.38 (m, 1 H), 2.73 )m, 2 H), 2.56 (m, 2 H), 2.10-1.62 (m, 12 H), 0.95 (m, 5 H); $^{13}$C-NMR δ (ppm): 180.1, 144.0, 142.9, 132.8 128.9, 118.5, 112.7, 74.0, 34.48, 34.0, 32.0, 31.9, 31.8, 29.5, 28.7, 28.6, 26.4, 26.3, 26.0, 23.9, 23.3, 22.7, 22.3; MS (ESI) m/z: 331 (M+H$^+$, 100%).

Example 30

2-(2-Chloro-ethyl)-2-methyl-3,4,7,8,9,10-hexahydro-7,10-methano-2H-benzo[h]chromen-6-ol

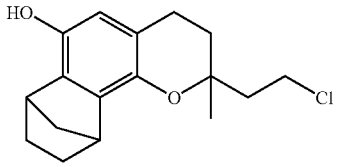

Step 1

To a solution of 4-chloro-butanone-2 (2.65 g, 25 mmol) in 25 ml of THF at −20° C. was added dropwise a solution of 1M vinyl magnesium bromide (40 ml, 40 mmol). After the completion of addition the mixture was stirred for one more hours at room temperature. To the mixture was added 10 ml of water at 0° C. with stirring. The mixture was dried over MgSO$_4$. After the removal of the solvent, the residue was purified via flash column chromatography on silica gel with 1:3 ethyl acetate and hexane as elute to afford 800 mg of 5-chloro-3-methyl-pent-1-en-3-ol. $^1$H-NMR (300 MHz, CDCl$_3$) δ (ppm): 5.86-5.90 (dd, 1H); 5.29 (d, 1H), 5.13 (d, 1H), 3.50-3.59 (t, 3H); 1.87-1.83 2.18 (m, 2H); 1.63-1.69 (m, 2H), 1.31 (s, 3H)

Step 2

A mixture of, 1,2,3,4-tetrahydro-1,4-methano-naphthalene-5,8-diol (1.34 g, 794 mmol), 1.0 ml (3.97 mmol) of BF$_3$.Et$_2$O and 25 ml of dioxane was heated up to 110° C. under a nitrogen atmosphere. A solution of 5-chloro-3-methyl-pent-1-en-3-ol (1.12g, 8.6 mmol) in 24 ml of dioxane was added slowly to the mixture. The addition was completed after two hours and the mixture was continued to reflux for an additional 3 hours. After cooling down to room temperature, the mixture was poured to water, extracted with ethyl acetate, washed with water and dried over MgSO$_4$. After the removal of solvents, the residue was mixed with methanol/HCl and let stirred overnight at room temperature. After the removal of the solvents the residue was purified via flash column chromatography on silica gel (1:3 EtOAc/Hex) twice to give 1.30 g of 2-(2-chloro-ethyl)-2-methyl-3,4,7,8,9,10-hexahydro-7,10-methano-2H-benzo[h]chromen-6-ol. $^1$H-NMR (300 MHz, CDCl$_3$) δ (ppm): 6.39 (s, 1H), 4.27 (s, 1H), 3.63-3.47 (m, 4H), 2.73-2.70 (m, 2H), 2.00-1.47 (m, 8H), 1.43-1.15 (m, 4H); MS: 307 (M+H$^+$, 100%).

Similarly, substituting in Step 1, 4-chloro-butanone-2 with 5-chloro-pentan-2-one, 6-chloro-3-methyl-hex-1-en-3-ol was produced ($^1$H-NMR (300 MHz, CDCl$_3$): 5.86-5.90 (dd, 1H); 5.29 (d, 1H), 5.13 (d, 1H), 3.50-3.59 (t, 3H); 1.87-1.83 2.18 (m, 2H); 1.63-1.69 (m, 2H), 1.31 (s, 3H)), and cycliza-tion with 3',6'-dihydrobenzo-norbornane gave of 2-(3-chloro-propyl)-2-methyl-3,4,7,8,9,10-hexahydro-7,10-methano-2H-benzo[h]chromen-6-ol: $^1$H-NMR (300 MHz, CDCl$_3$) δ (ppm): 6.39 (s. 1H), 4.27 (s, 1H), 3.63-3.47 (m, 4H), 2.73-2.70 (m, 2H), 2.00-1.47 (m, 8H), 1.43-1.15 (m, 4H); MS: 307 (M+H$^+$, 100%)

Similarly, substituting in Step 1, 4-chloro-butanone-2 with 1-thiophen-2-yl-ethanone, followed by cyclization with 3',6'-dihydrobenzo-norbornane gave 2-methyl-2-thiophen-2-yl-3,4,7,8,9,10-hexahydro-7,10-methano-2H-benzo[h]chromen-6-ol, $^1$H-NMR (300 MHz, CDCl$_3$) δ (ppm): 7.28 (m, 1H), 7.00 (m, 2H), 4.20 (m, 1H), 3.51 (m, 2H), 2.90-2.78 (m, 2H), 2.43-2.24 (m, 2H), 1.96-1.80 (m, 3H), 1.77-1.74 (m, 4H), 1.38-1.20 (m, 3H); MS: 313 (M+H$^+$, 38%), 335 (M+Na$^+$, 100%)

Similarly, substituting in Step 1, 4-chloro-butanone-2 with 1-thiazol-2-yl-ethanone, followed by cyclization with 3',6'-dihydrobenzo-norbornane gave 2-methyl-2-thiazol-2-yl-3,4,7,8,9,10-hexahydro-7,10-methano-2-H-benzo[h]chromen-6-ol, $^1$H-NMR (300 MHz, CDCl$_3$) δ (ppm): 7.74 (dd, 1H), 7.19 (dd, 1H), 6.39 (s, 1H), 4.67 (s, 1H), 3.53-3.47 (m, 4H), 2.26 (s, 3H), 1.91-1.88 (m, 3H), 1.70 (m, 1H), 7.19 (dd, 1H), 1.31-1.21 (m, 3H); MS: 314 (M+H$^+$, 100%)

Example 31

2-Methyl-2-[3-(pyridin-4-ylsulfanyl)-propyl]-3,4,7,8,9,10-hexahydro-7,10-methano-2H-benzo[h]chromen4-ol

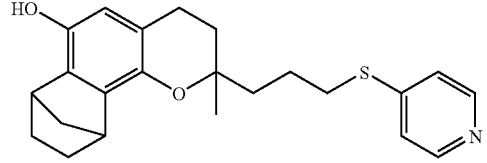

A mixture of 100 mg of iodide (0.25 mmol), 66 mg of 4-mercapto-pyridine (0.39 mmol), 55 mg of K$_2$CO$_3$ (0.39 mmol) in 1.5 mL of DMF was stirred overnight. The mixture was dumped to water and extracted with DCM. Purification flash column chromatography on silica gel (3:1 Hexane/EtOAc) of the residue gave 55 mg of 2-methyl-2-[3-(pyridin-4-ylsulfanyl)-propyl]-3,4,7,8,9,10-hexahydro-7,10-methano-2H-benzo[h]chromen-6-ol. $^1$H-NMR (300 MHz, CDCl$_3$) δ (ppm): 7.86 (m, 1H), 7.78 (m, 1H), 7.41 (m, 1H), 7.26 (m, 1H), 6.33 (s, 1H), 4.23 (s, 1H), 3.50-3.42 (m, 2H), 3.38-3.25 (m, 2H), 2.80 (m, 2H), 2.07-1.77 (m, 12H), 1.31-1.24 (m, 6H); MS: 382 (M+H$^+$, 100%)

Similarly substituting 4-mercapto-pyridine with 2-methyl-propane-1-thiol gave 2-(3-isobutylsulfanyl-propyl)-2-methyl-3,4,7,8,9,10-hexahydro-7,10-methano-2H-benzo[h]chromen-6-ol;

$^1$H-NMR (300 MHz, CDCl$_3$) δ (ppm): 6.34 (s, 1H), 4.22 (s, 1H), 3.60-3.44 (s, 2H), 2.73-2.68 (m, 2H), 2.60-2.50 (m, 2H), 2.42-2.38 (m, 2H), 1.88-1.40 (m, 6H), 1.29-1.26 (m, 10H), 0.95-0.84 (mm, 6H); MS: 361 (M+H$^+$, 100%).

Example 32

3-[6-hydroxy-2-methyl-5-(3-methyl-but-2-enyl)-3,4,7,8,9,10-hexahydro-7,10-methano-2H-benzo[h]chromen-2-yl]-propionic acid

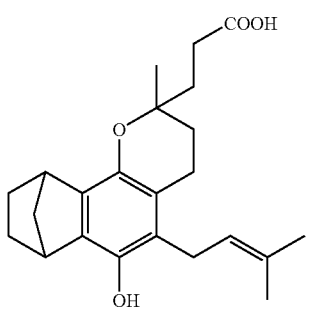

A solution of 3-(6-hydroxy-2-methyl-3,4,7,8,9,10-hexahydro-7,10-methano-2H-benzo[h]chromen-2-yl)-propionic acid, (2.39 mmol) in 1M aq. NaOH (4.8 mL, 4.8 mmol) was cooled to 0° C., and treated with prenyl bromide (0.277 mL, 2.39 mmol). Following stirring for 7 h at ambient temperature the reaction mixture was made slightly acidic with 0.5M HCl and shaken with EtOAc. The organic phase was evaporated yielding 1. The mixture was subjected to column chromatography on silica gel (SiO$_2$: hexane:EtOAc, 85:15 v/v eluting yielded 3-[6-hydroxy-2-methyl-5-(3-methyl-but-2-enyl)-3,4,7,8,9,10-hexahydro-7,10-methano-2H-benzo[h]chromen-2-yl]-propionic acid $^1$H-NMR (300 MHz, CDCl$_3$) δ (ppm): 5.17 (t, J=6, 1H), 3.54 (br s, 1H), 3.49 (br s, 1H), 3.18-3.37 (m, 2H), 2.70 (t, J=7, 2H), 2.49-2.62 (m, 2H), 1.60-2.07 (m, 13H), 1.39-1.48 (m, 1H), 1.05-1.32 (m, 5H). $^{13}$C-NMR (75 MHz CDCl$_3$) δ (ppm): 180.1, 141.1, 133.9, 133.3, 132.9, 122.9, 122.3, 117.4, 73.2, 49.0, 48.9, 40.0, 39.8, 33.6, 32.0, 28.7, 26.7, 25.9, 25.6, 23.8, 233.2, 20.5, 18.0. MS ESI-Pos m/z371.2 (M+H$^+$)

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference

What is claimed is:

1. A compound represented by Formula I:

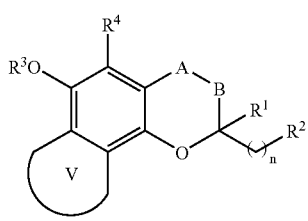

Formula I wherein:

-A-B— is —CH$_2$—(CH$_2$)$_{0-2}$—; —CH═CH—; —CH$_2$—O—; —CH$_2$—S—; or —CH$_2$—N—;

n is 0 to 5;

V is C$_{7-12}$-bicyclo[a.b.c]alkyl; C$_{7-12}$-bicyclo[a.b.c]alkenyl; C$_{7-12}$-heterobicyclo[a.b.c]alkyl; or C$_{7-12}$-heterobicyclo[a.b.c]alkenyl; and a, b, and c are 0 to 6; and wherein the bicyclo ring is optionally substituted with one or more substituents selected from C$_{1-6}$-alkyl, halogen, haloalkyl, carboxy, alkoxycarbonyl, cyano, hydroxy, alkoxy, thiol, and oxo;

R$^1$ is C$_{1-6}$ alkyl;

R$^2$ is C$_{1-20}$ alkyl; optionally substituted C$_{2-20}$ alkenyl; halogen; hydroxy; alkoxy; acyl; —C(O)OR; —S(O)$_2$OR; —NR'R''; —NH—C(═NH$_2$)—NR'R''; —N—SO$_2$R; —NHC(O)NR'R''; —N(OH)C(O)NR'R''; —SO$_2$NR'R''; —C(O)NR'R''; —S(O)$_{0-2}$R'''; —PO(OR)$_2$; triphenylphosphonium; trialkylphosphonium; optionally substituted aryl; or optionally substituted heterocyclyl;

R$^3$ is hydrogen; optionally substituted C$_{1-20}$ alkyl; C$_{2-20}$ alkenyl; hydroxyalkyl; acyl; glucoside; phosphoryl; phosphoryloxyalkyl; carboxyalkylcarbonyl; aminoalkylcarbonyl; or alkylketocarbonyl;

R$^4$ is hydrogen; halogen; nitro; cyano; optionally substituted C$_{1-6}$alkyl; aryl, aralkyl, hetercyclyl or heterocyclylalkyl all optionally substituted with alkyl, hydroxy, alkoxy, nitro, acyl, amino, oxo or —C(O)OR; optionally substituted alkenyl; hydroxy; alkoxy; nitro; —C(O)OR; —C(O)NR'R''; —NR'R''; —NHC(O)NR'R''; —NR'—SO$_2$—R; —NH—C(═NH$_2$)—NR'R''; —SO$_2$NR'R''; or —P(O)(OR)$_2$; or R$^3$ and R$^4$ taken together with the atoms to which they are attached form a heterocyclic ring;

R is hydrogen; optionally substituted alkyl; optionally substituted aryl; optionally substituted arylalkyl; optionally substituted cycloalkyl; or optionally substituted heterocyclyl;

R' and R'' are independently of each other hydrogen; C$_{1-6}$ alkyl; hydroxyalkyl; aminoalkyl; optionally substituted aryl; or optionally substituted benzyl; or R' and R'' taken together with the atom to which they are attached form a 5 to 8 membered aromatic, saturated or unsaturated ring, optionally incorporating one additional atom chosen from N, O, or S and optionally substituted with a substituent selected from the group consisting of C$_{1-6}$ alkyl, halo, cyano, alkylthio, lower alkoxy, phenyl, benzyl and carboxy; and R''' is optionally substituted C$_{1-6}$ alkyl; optionally substituted aryl; or optionally substituted heterocyclyl; or single stereoisomers and mixtures of stereoisomers, or the pharmaceutically acceptable salts thereof.

2. The compound of claim 1, wherein R$^3$ is hydrogen.

3. The compound of claim 1, wherein R$^4$ is hydrogen, C$_{1-6}$ alkyl optionally substituted with halogen, haloalkyl, hydroxy, alkoxy, amino, sulfanyl, carboxy, nitro or cyano; or C$_{2-12}$ alkenyl optionally substituted with halogen, haloalkyl, hydroxy, alkoxy, amino, sulfanyl, carboxy, nitro or cyano.

4. The compound of claim 1, wherein V is a bicyclo[2.2.1]heptane ring, and the compound is represented by Formula Ia:

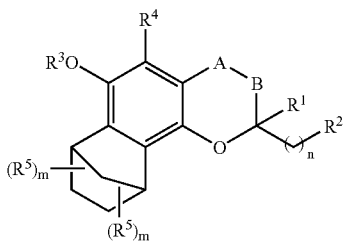

Formula Ia wherein -A-B— is —CH$_2$—CH$_2$— or —CH=CH—; R$^1$, R$^2$, R$^3$, R$^4$, and n are as defined in claim 1; m is in each occurrence independently 0-3; and R$^5$ is selected from optionally substituted C$_{1-6}$ alkyl, halogen, haloalkyl, carboxy, alkoxycarbonyl, cyano, hydroxy, alkoxy, thiol, and oxo.

5. The compound of claim 4, wherein R$^2$ is C$_{1-6}$ alkyl; halogen; hydroxy; alkoxy; —C(O)OR; —SO$_2$NR'R''; —C(O)NR'R''; —SR'''; —PO(OR)$_2$; triphenylphosphonium; trialkylphosphonium; phenyl optionally substituted with C$_{1\neq}$alkyl, halogen, haloalkyl, carboxy, alkoxycarbonyl, cyano, hydroxy, alkoxy, thiol, and oxo; or heterocyclyl selected from morpholine, piperidine, piperazine, thiazole, thiazolidine, isothiazole, oxazole, isoxazole, pyrazole, pyrazolidine, pyrazoline, imidazole, imidazolidine, benzothiazole, pyridine, pyrazine, pyrimidine, pyridazine, pyrrole, pyrrolidine, quinoline, quinazoline, purine, carbazole, benzimidazole, pyrimidine, thiophene, benzothiophene, pyran, tetrahydropyran, benzopyran, furan, tetrahydrofuran, indole, indoline, indazole, xanthene, thioxanthene, acridine, and quinuclidine, optionally substituted with C$_{1-6}$ alkyl, halogen, haloalkyl, carboxy, alkoxycarbonyl, cyano, hydroxy, alkoxy, thiol, and oxo.

6. The compound of claim 5, wherein R$^2$ is —C(O)OR or —PO(OR)$_2$, m is 0 and R is hydrogen or C$_{1-6}$ alkyl.

7. The compound of claim 5, wherein R$^1$ and R$^2$ are independently of each other C$_{1-6}$ alkyl; and m and n are 0.

8. The compound of claim 1, wherein V is a bicyclo[2.2.2]octane ring and the compound is represented by Formula Ib:

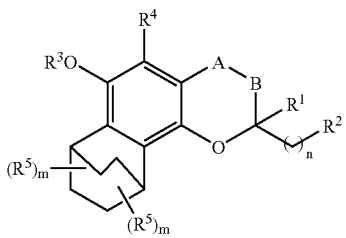

Formula Ib wherein -A-B— is —CH$_2$—CH$_2$— or —CH=CH—; R$^1$, R$^2$, R$^3$, R$^4$, and n are as defined in claim 1; m is in each occurrence independently 0-3; and R$^5$ is selected from optionally substituted C$_{1-6}$ alkyl, halogen, haloalkyl, carboxy, alkoxycarbonyl, cyano, hydroxy, alkoxy, thiol, and oxo.

9. The compound of claim 8, wherein R$^2$ is C$_{1-6}$ alkyl; halogen; hydroxy; alkoxy; —C(O)OR; —SO$_2$NR'R''; —C(O)NR'R''; —SR'''; —PO(OR)$_2$; triphenylphosphonium; trialkylphosphonium; phenyl optionally substituted with C$_{1-6}$ alkyl, halogen, haloalkyl, carboxy, alkoxycarbonyl, cyano, hydroxy, alkoxy, thiol, and oxo; or heterocyclyl selected from morpholine, piperidine, piperazine, thiazole, thiazolidine, isothiazole, oxazole, isoxazole, pyrazole, pyrazolidine, pyrazoline, imidazole, imidazolidine, benzothiazole, pyridine, pyrazine, pyrimidine, pyridazine, pyrrole, pyrrolidine, quinoline, quinazoline, purine, carbazole, benzimidazole, pyrimidine, thiophene, benzothiophene, pyran, tetrahydropyran, benzopyran, furan, tetrahydrofuran, indole, indoline, indazole, xanthene, thioxanthene, acridine, and quinuclidine, optionally substituted with C$_{1-6}$ alkyl, halogen, haloalkyl, carboxy, alkoxycarbonyl, cyano, hydroxy, alkoxy, thiol, and oxo.

10. The compound of claim 9, wherein R$^2$ is —C(O)OR or —PO(OR)$_2$, and R is hydrogen or C$_{1-6}$ alkyl.

11. The compound of claim 8, wherein R$^1$ and R$^2$ are independently of each other C$_{1-6}$ alkyl and m and n are 0.

12. The compound of claim 1, wherein V is a bicyclo[3.2.2]nonane ring and where the compound is represented by Formula Ic:

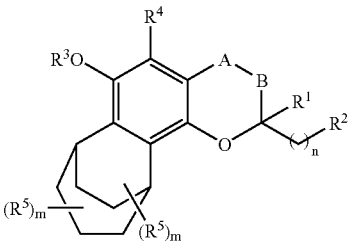

Formula Ic wherein -A-B— is —CH$_2$—CH$_2$— or —CH=CH—; R$^1$, R$^2$, R$^3$, R$^4$, and n are as defined in claim 1; m is in each occurrence independently 0-3; and R$^5$ is selected from optionally substituted C$_{1-6}$ alkyl, halogen, haloalkyl, carboxy, alkoxycarbonyl, cyano, hydroxy, alkoxy, thiol, and oxo.

13. The compound of claim 12, wherein R$^2$ is C$_{1-6}$ alkyl; halogen; hydroxy; alkoxy; —C(O)OR; —SO$_2$NR'R''; —C(O)NR'R''; —SR'''; —PO(OR)$_2$; triphenylphosphonium; trialkylphosphonium; phenyl optionally substituted with C$_{1-6}$ alkyl, halogen, haloalkyl, carboxy, alkoxycarbonyl, cyano, hydroxy, alkoxy, thiol, and oxo; or heterocyclyl selected from morpholine, piperidine, piperazine, thiazole, thiazolidine, isothiazole, oxazole, isoxazole, pyrazole, pyrazolidine, pyrazoline, imidazole, imidazolidine, benzothiazole, pyridine, pyrazine, pyrimidine, pyridazine, pyrrole, pyrrolidine, quinoline, quinazoline, purine, carbazole, benzimidazole, pyrimidine, thiophene, benzothiophene, pyran, tetrahydropyran, benzopyran, furan, tetrahydrofuran, indole, indoline, indazole, xanthene, thioxanthene, acridine, and quinuclidine, optionally substituted with C$_{1-6}$ alkyl, halogen, haloalkyl, carboxy, alkoxycarbonyl, cyano, hydroxy, alkoxy, thiol, and oxo.

14. The compound of claim 13, wherein R$^2$ is —C(O)OR or —PO(OR)$_2$, and R is hydrogen or C$_{1-6}$ alkyl.

15. The compound of claim 12, wherein R$^1$ and R$^2$ are independently of each other C$_{1-6}$ alkyl; and m and n are 0.

16. The compound of claim 1, wherein -A-B— is —CH$_2$—CH$_2$— and n is 2 or 3.

17. The compound of claim 16, wherein V is a bicyclo[2.2.1]heptane ring, a bicyclo[2.2.2]octane ring, or a bicyclo[3.2.2]nonane ring.

18. The compound of claim 17, wherein R$^2$ is —C(O)OR, and R is hydrogen or C$_{1-6}$ alkyl.

19. The compound of claim 1, wherein -A-B— is —CH$_2$=CH$_2$— and n is 2 or 3.

20. The compound of claim 19, wherein V is a bicyclo[2.2.1]heptane ring, a bicyclo[2.2.2]octane ring, or a bicyclo[3.2.2]nonane ring.

21. The compound of claim 20, wherein $R^2$ is —C(O)OR, and R is hydrogen or $C_{1-6}$ alkyl.

22. The compound of claim 1, wherein $R^1$ and $R^2$ are $C_{1-6}$ alkyl and n is 0.

23. The compound of claim 22, wherein -A-B— is —CH$_2$—CH$_2$—.

24. The compound of claim 22, wherein -A-B— is —CH$_2$=CH$_2$—.

25. The compound of claim 1 selected from:

3-(6-Hydroxy-2-methyl-3,4,7,8,9,10-hexahydro-7,10-methano-2H-benzo[h]chromen-2-yl)-propionic acid methyl ester;

3-(6-Hydroxy-2-methyl-3,4,7,8,9,10-hexahydro-7,10-methano-2H-benzo[h]chroman-2-yl)-propionic acid;

2,2,-Dimethyl-3,4,7,8,9,10-hexahydro-7,10-methano-2H-benzo[h]chromen-6-ol;

3-(6-Hydroxy-2-methyl-3,4,7,8,9,10-hexahydro-7,10-propano-2H-benzo[h]chromen-2-yl)-propionic acid methyl ester;

2-Methyl-2-[3-(thiazol-2-ylsulfanyl)-propyl]-3,4,7,8,9,10-hexahydro-7,10-methano-2H-benzo[h]chromen-6-ol;

[3-(6-Hydroxy-2-methyl-3,4,7,8,9,10-hexahydro-7,10-methano-2H-benzo[h]chromen-2-yl)-propyl]-phosphonic acid dimethyl ester;

[3-(6-Hydroxy-2-methyl-3,4,7,8,9,10-hexahydro-7,10-methano-2H-benzo[h]chromen--yl)-propyl]-phosphonic acid;

3-(6-Hydroxy-2-methyl-3,4,7,8,9,10-hexahydro-7,10-methano-2H-benzo[h]chromen-2-yl)-propionic acid methyl ester;

4-(6-Hydroxy-2-methyl-3,4,7,8,9,10-hexahydro-7,10-methano-2H-benzo[h]chromen-2-yl)-butane-1-sulfonic acid dimethylamide;

2-(3-Hydroxy-propyl)-2-methyl-3,4,7,8,9,10-hexahydro-7,10-methano-2H-benzo[h]chromen-6-ol;

2-(3-Chloro-propyl)-2-methyl-3,4,7,8,9,10-hexahydro-7,10-methano-2H-benzo[h]chromen-6-ol 2,2-Dimethyl-3,4,7,8,9,10-hexahydro-7,10-methano-2H-benzo[h]chromen-6-ol;

-(2-Chloro-ethyl)-2-methyl-3,4,7,8,9,10-hexahydro-7,10-methano-2H-benzo[h]chromen-6-ol;

2-Methyl-2-thiazol-2-yl-3,4,7,8,9,10-hexahydro-7,10-methano-2H-benzo[h]chromen-6-ol;

2,2-Dimethyl-3,4,7,8,9,10-hexahydro-7,10-ethano-2H-benzo[h]chromen-6-ol;

3-(6-Hydroxy-2-methyl-3,4,7,8,9,10-hexahydro-7,10-ethano-2H-benzo[h]chromen-2-yl)-propionic acid;

2-(3-Chloro-propyl)-2-methyl-3,4,7,8,9,10-hexahydro-7,10-ethano-2H-benzo[h]chromen-6-ol;

4-(6-Hydroxy-2,2-dimethyl-3,4,7,8,9,10-hexahydro-7,10-methano-2H-benzo[h]chromen-5-ylmethylene)-2-methyl-5-propyl-2,4-dihydro-pyrazol-3-one; and single stereoisomers and mixtures of stereoisomers, or the pharmaceutically acceptable salts thereof.

26. The compound of claim 1 selected from the group represented by the following structures:

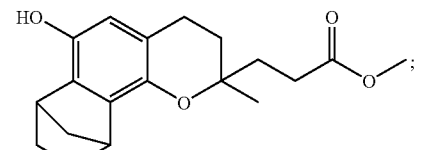

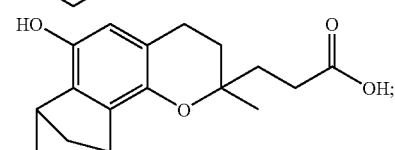

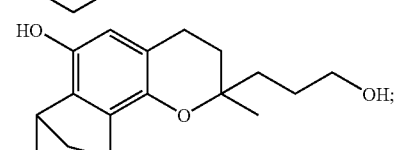

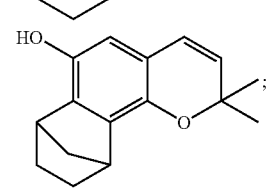

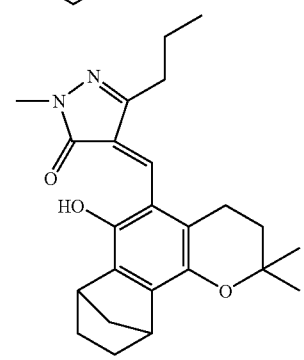

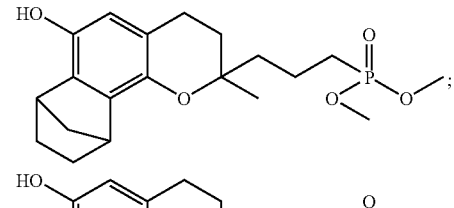

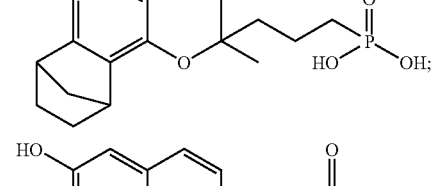

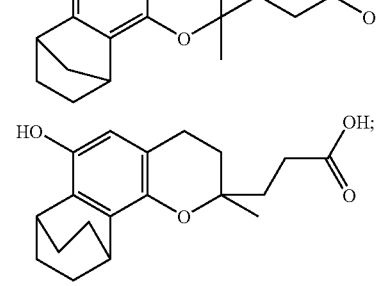

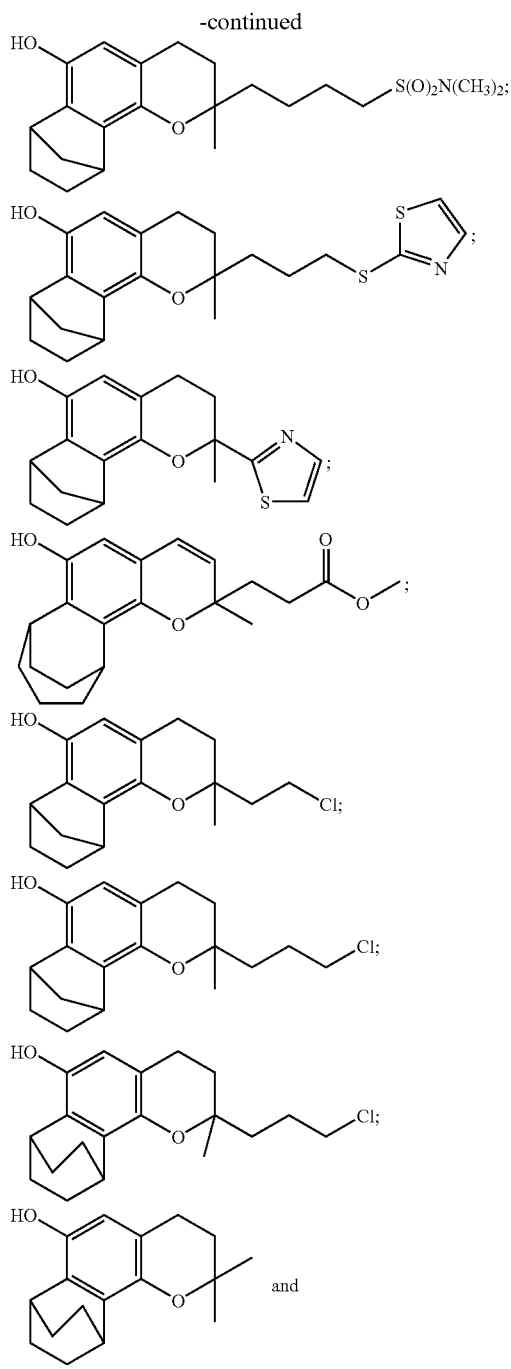

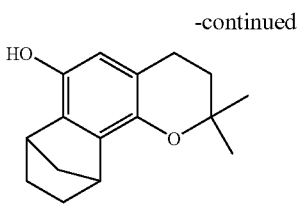

or single stereoisomers and mixtures of stereoisomers, or the pharmaceutically acceptable salts thereof.

27. A pharmaceutical composition comprising a compound of claim 1 or stereoisomers, mixtures of stereoisomers or pharmaceutically acceptable salts thereof, admixed with a pharmaceutically acceptable excipient.

28. The pharmaceutical composition of claim 27 comprising one or more compounds selected from the group represented by the structures:

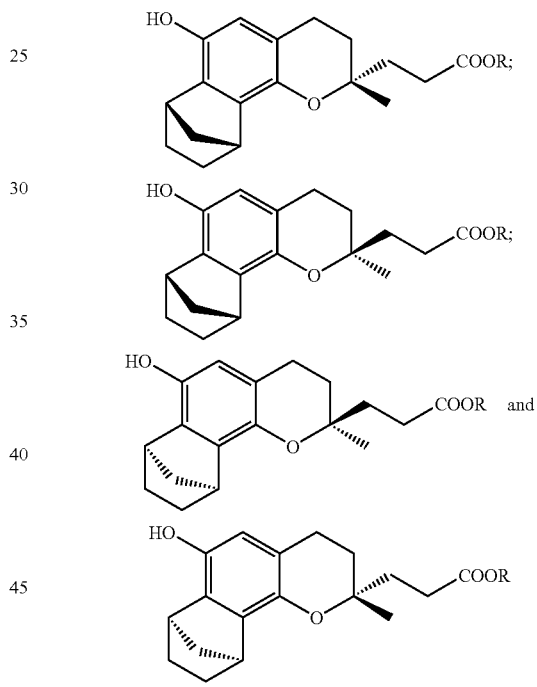

wherein R is hydrogen or $C_{1-4}$ alkyl.

* * * * *

UNITED STATES PATENT AND TRADEMARK OFFICE
CERTIFICATE OF CORRECTION

PATENT NO. : 7,470,798 B2
APPLICATION NO. : 10/941121
DATED : December 30, 2008
INVENTOR(S) : Bing Wang et al.

It is certified that error appears in the above-identified patent and that said Letters Patent is hereby corrected as shown below:

At Columns 29 and 30: please delete the line numbering appearing in the reaction scheme.

At Column 62, line 24, please replace "☐yridine" with --pyridine--.

At Column 62, line 43, please replace "ethano 2H" with --ethano-2H--.

At Column 62, line 47, please replace "ester." with --ester;--.

At Column 63, line 42, please replace "eyridine" with --pyridine--.

At Column 63, line 50, please replace "dro--" with --dro- --.

At Column 64, line 52, please replace "☐yridine" with --pyridine--.

At Column 64, line 67, please replace "ethano 2H" with --ethano-2H--.

At Column 79, line 23, please replace "$C_{1\neq}$alkyl" with --$C_{1-6}$alkyl--.

Signed and Sealed this

Twenty-second Day of September, 2009

David J. Kappos
*Director of the United States Patent and Trademark Office*